(12) United States Patent
Dankulich et al.

(10) Patent No.: US 8,299,048 B2
(45) Date of Patent: Oct. 30, 2012

(54) HEXAHYDROCYCLOPENTYL[F]INDAZOLE SULFONAMIDES AND DERIVATIVES THEREOF AS SELECTIVE GLUCOCORTICOID RECEPTOR MODULATORS

(75) Inventors: William P. Dankulich, Collegeville, PA (US); Mildred L. Kaufman, Schwenksville, PA (US); Danielle M. McMaster, Boothwyn, PA (US); Robert S. Meissner, Schwenksville, PA (US); Helen J. Mitchell, Richboro, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 100 days.

(21) Appl. No.: 12/921,243

(22) PCT Filed: Feb. 24, 2009

(86) PCT No.: PCT/US2009/034968
§ 371 (c)(1),
(2), (4) Date: Sep. 7, 2010

(87) PCT Pub. No.: WO2009/111214
PCT Pub. Date: Sep. 11, 2009

(65) Prior Publication Data
US 2011/0105440 A1    May 5, 2011

Related U.S. Application Data

(60) Provisional application No. 61/068,370, filed on Mar. 6, 2008.

(51) Int. Cl.
| | |
|---|---|
| A61K 31/635 | (2006.01) |
| A61K 31/416 | (2006.01) |
| A61K 31/444 | (2006.01) |
| A61K 31/4178 | (2006.01) |
| C07D 401/14 | (2006.01) |
| C07D 231/54 | (2006.01) |
| C07D 405/12 | (2006.01) |
| C07D 409/14 | (2006.01) |

(52) U.S. Cl. .................. 514/158; 514/230.5; 514/333; 514/338; 514/380; 514/406; 544/105; 546/256; 546/275.7; 548/235; 548/243; 548/311.7; 548/359.1

(58) Field of Classification Search .................. None
See application file for complete search history.

(56) References Cited

U.S. PATENT DOCUMENTS

| | | |
|---|---|---|
| 3,940,390 A | 2/1976 | Singer et al. |
| 2006/0069269 A1 | 3/2006 | Amrein et al. |

*Primary Examiner* — Kamal Saeed
(74) *Attorney, Agent, or Firm* — Patricia A. Shatynski; Valerie J. Camara

(57) ABSTRACT

The present invention is directed to hexahydrocyclopentylf] indazole carboxamides and derivatives thereof as selective glucocorticoid receptor ligands useful for treating a variety of autoimmune and inflammatory diseases or conditions. Pharmaceutical compositions and methods of use are also included.

14 Claims, No Drawings

HEXAHYDROCYCLOPENTYL[F]INDAZOLE SULFONAMIDES AND DERIVATIVES THEREOF AS SELECTIVE GLUCOCORTICOID RECEPTOR MODULATORS

CROSS REFERENCE TO RELATED APPLICATIONS

This application is a U.S. National Phase application under 35 U.S.C. §371 of PCT Application No. PCT/US2009/034968, filed Feb. 24, 2009, which claims priority under 35 U.S.C. §119(e) from U.S. Provisional Application Ser. Nos. 61/068,370, filed Mar. 6, 2008.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor has an essential role in regulating human physiology and immune response. Steroids that interact with the glucocorticoid receptor have been shown to be potent anti-inflammatory agents. The present invention is directed to a novel class of compounds that are selective glucocorticoid receptor modulators that have potent anti-inflammatory and immunosuppressive activity and possess advantages over steroidal glucocorticoid ligands with respect to side effects, efficacy, toxicity and/or metabolism.

SUMMARY OF THE INVENTION

The present invention is directed to hexahydrocyclopenty[f]indazole sulfonamides and derivatives thereof as selective glucocorticoid receptor ligands useful for treating a variety of autoimmune and inflammatory diseases or conditions. Pharmaceutical compositions and methods of use are also included.

DETAILED DESCRIPTION OF THE INVENTION

In one aspect the invention encompasses compounds of Formula I

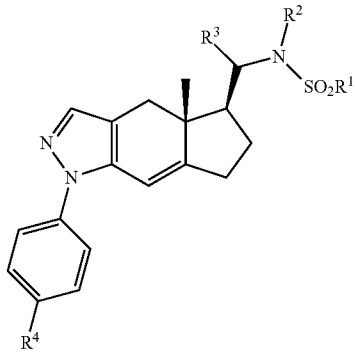

I or a pharmaceutically acceptable salt thereof, wherein $R^1$ is selected from the group consisting of:
  (a) $C_{1-6}$alkyl, optionally mono-, di- or tri substituted with substituents independently selected from
    (1) halo,
    (2) —$CF_3$,
    (3) hydroxyl,
    (4) oxo,
    (5) —CN, and
    (6) pyridine,
  (b) $C_{2-6}$alkenyl, optionally mono-, di- or tri substituted with fluoro,
  (c) —$C_{3-6}$cycloalkyl,
  (d) —$C_{1-2}$alkyl$C_{3-6}$cycloalkyl,
  (e) heterocycle,
  (f) —$C_{1-2}$alkylheterocycle,
  (g) aryl selected from phenyl or naphthyl,
  (h) —$C_{1-2}$alkylaryl,
  (i) —$C_{2-4}$alkenylaryl,
  (j) heteroaryl,
  (k) —$C_{1-2}$alkylheteroaryl,
  (l) —Oheteroaryl,
  (m) —$OC_{1-6}$alkyl optionally mono-, di- or tri substituted with fluoro,
  (n) —C1-4alkyl-O—C1-6alkyl, optionally substituted with hydroxy, or —O—S(O)$_2$—$C_{1-2}$alkyl-$CF_3$,
  (O) —$OC_{3-6}$cycloalkyl, and
  (p) —Oaryl,
wherein the heteroaryl, aryl and heterocycle of choices (e), (f), (g), (h), (i), (j), (k), (l), and (p) are optionally substituted with 1, 2 or 3 substituents independently selected from the group consisting of
  (1) hydroxyl,
  (2) halo,
  (3) —CN,
  (4) —$CF_3$,
  (5) —$C_{1-4}$alkyl,
  (6) —$OC_{1-4}$alkyl,
  (7) —O—$CH_2CF_3$,
  (8) heteroaryl selected from pyrazole, thiophene, imidazole, and oxazole, optionally substituted with 1, 2 or 3 substitutents independently selected from methyl, $CF_3$ and halo,
  (9) —NH—$OCH_3$,
  (10) phenyl,
  (11) —O-phenyl,
  (12) pyridine,
  (13) —O-pyridine,
  (14) —NH—C(O)—NH—$CH_3$,
  (15) —NH—C(O)—$C_{1-4}$alkyl,
  (16) —NH—C(O)—$C_{3-6}$cycloalkyl,
  (17) —$C_{1-3}$alkyl-C(O)—OH,
  (18) —$C_{1-3}$alkyl-C(O)—O—$CH_3$,
  (19) —C(O)—$NH_2$,
  (20) —C(O)—$C_{1-4}$alkyl-$NH_2$,
  (21) —C(O)—NH—$C_{3-6}$cycloalkyl,
  (22) —C(O)—OH,
  (23) —C(O)—O—$C_{1-4}$alkyl,
  (24) —$C_{1-2}$alkyl-heterocycle,
  (25) —$C_{2-4}$alkenyl-C(O)-phenyl, and
  (26) —O—S(O)$_2$—$C_{1-2}$alkyl-$CF_3$;
$R^2$ is selected from the group consisting of:
  (a) H,
  (b) OH,
  (c) $C_{1-8}$alkyl, optionally mono-, di- or tri substituted with substituents independently selected from
    (1) halo,
    (2) hydroxyl, (3) oxo,
(4) —CN,
(5) CHF$_2$,
(6) CF$_3$,
(7) pyridyl,
(8) —O—S(O)$_2$—CF$_3$, and
(9) —O—S(O)$_2$—C$_{1-2}$alkyl-CF$_3$,
(d) C$_{2-6}$alkenyl, optionally mono-, di- or tri substituted with fluoro,
(e) —C$_{1-2}$alkylC$_{3-6}$cycloalkyl,
(f) heterocycle,
(g) —C$_{1-2}$alkylheterocycle,
(h) aryl selected from phenyl or naphthyl,
(i) —C$_{1-3}$alkylaryl,
(j) —C$_{2-4}$alkenylaryl,
(k) heteroaryl,
(l) —C$_{1-2}$alkylheteroaryl,
(m) —CH$_2$pyridyl, and
(O) —C1-4alkyl-O—C1-6alkyl, optionally substituted with hydroxy, or —O—S(O)$_2$—C$_{1-2}$alkyl-CF$_3$,
wherein the cycloalkyl, heteroaryl, aryl and heterocycle of choices (e), (f), (g), (h), (i), (j), (k), (l) and (m) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OCH$_3$,
(7) —O—CH$_2$CF$_3$,
(8) heteroaryl selected from pyrazole, thiophene, imidazole, and oxazole, optionally substituted with 1, 2 or 3 substitutents independently selected from methyl, and halo,
(9) —NH—OCH$_3$,
(10) phenyl,
(11) —O-phenyl,
(12) pyridine,
(13) —O-pyridine,
(14) —NH—C(O)—NH—CH$_3$,
(15) —NH—C(O)—C$_{1-4}$alkyl,
(16) —NH—C(O)—C$_{3-6}$cycloalkyl,
(17) —C$_{1-3}$alkyl-C(O)—OH,
(18) —C$_{1-3}$ alkyl-C(O)—O—CH$_3$,
(19) —C(O)—NH$_2$,
(20) —C(O)—C$_{1-4}$alkyl-NH$_2$,
(21) —C(O)—NH—C$_{3-6}$cycloalkyl,
(22) —C(O)—OH,
(23) —C(O)—O—C$_{1-4}$alkyl,
(24) —C$_{1-2}$alkyl-heterocycle,
(25) —C$_{2-4}$alkenyl-C(O)-phenyl, and
(26) —O—S(O)$_2$—C$_{1-2}$alkyl-CF$_3$;
R$^3$ is selected from
(a) H,
(b) C$_{1-6}$alkyl,
(c) C$_{3-6}$cycloalkyl, and
(d) C$_{1-6}$-fluoroalkyl; and
R$^4$ is hydrogen or F.
Within this aspect is a genus of compounds wherein R$^1$ is selected from the group consisting of:
(a) C$_{1-6}$alkyl, optionally mono-, di- or tri substituted with substituents independently selected from
(1) halo selected from fluoro and chloro,
(2) —CF$_3$,
(3) hydroxyl, and
(4) pyridine,
(b) C$_{2-6}$alkenyl, optionally mono-, di- or tri substituted with fluoro,
(c) —C$_{3-6}$cycloalkyl,
(d) —C$_{1-2}$alkylC$_{3-6}$cycloalkyl,
(e) heterocycle,
(f) —C$_{1-2}$alkylheterocycle,
(g) aryl selected from phenyl or naphthyl,
(h) —C$_{1-2}$alkylaryl,
(i) —C$_{2-4}$alkenylaryl,
(j) heteroaryl,
(k) —C$_{1-2}$alkylheteroaryl,
(l) —Oheteroaryl,
(m) —OC$_{1-6}$alkyl optionally mono-, di- or tri substituted with fluoro,
(n) —C1-4alkyl-O—C1-6alkyl, optionally substituted with hydroxy, or —O—S(O)$_2$—C$_{1-2}$alkyl-CF$_3$,
(O) —OC$_{3-6}$cycloalkyl, and
(p) —Oaryl,
wherein the heteroaryl, aryl and heterocycle of choices (e), (f), (g), (h), (i), (j), (k), (l), and (p) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OC$_{1-4}$alkyl.
(7) —O—CH$_2$CF$_3$,
(8) —NH—OCH$_3$,
(9) —NH—C(O)—NH—CH$_3$,
(10) —NH—C(O)—C$_{1-4}$alkyl,
(11) —NH—C(O)—C$_{3-6}$cycloalkyl,
(12) —C$_{1-3}$alkyl-C(O)—OH,
(13) —C$_{1-3}$ alkyl-C(O)—O—CH$_3$,
(14) —C(O)—NH$_2$,
(15) —C(O)—C$_{1-4}$alkyl-NH$_2$,
(16) —C(O)—NH—C$_{3-6}$cycloalkyl,
(17) —C(O)—OH,
(18) —C(O)—O—C$_{1-4}$alkyl,
(19) —C$_{1-2}$alkyl-heterocycle,
(20) —C$_{2-4}$alkenyl-C(O)-phenyl, and
(21) —O—S(O)$_2$—C$_{1-2}$alkyl-CF$_3$.
Within this genus, there is a sub-genus of compounds wherein
R$^1$ is selected from the group consisting of
(a) C$_{1-6}$alkyl, optionally mono-, di- or tri substituted with substituents independently selected from
(1) halo selected from fluoro and chloro,
(2) —CF$_3$,
(3) hydroxyl, and
(4) pyridine,
(b) —C$_{3-6}$cycloalkyl,
(c) —C$_{1-2}$alkylC$_{3-6}$cycloalkyl,
(d) heterocycle,
(e) —C$_{1-2}$alkylheterocycle,
(f) aryl selected from phenyl or naphthyl,
(g) —C$_{1-2}$alkylaryl,
(h) heteroaryl,
(i) —C$_{1-2}$alkylheteroaryl,
wherein the heteroaryl, aryl and heterocycle of choices (d), (e), (f), (g), (h) and (i) are optionally substituted with 1, 2 or 3 substituents independently selected from the group consisting of
(1) halo,
(2) —CN,
(3) —CF$_3$, (4) —C$_{1-4}$alkyl,
(5) —OC$_{1-4}$alkyl,
(6) —O—CH$_2$CF$_3$,
(7) —C(O)—NH$_2$, and
(8) —C(O)—O—C$_{1-4}$alkyl.

Within this sub-genus there is a class of compounds wherein
R$^1$ is selected from the group consisting of:
(a) C$_{1-6}$alkyl, optionally mono-, di- or tri substituted with substituents independently selected from
  (1) halo selected from fluoro and chloro,
  (2) —CF$_3$,
  (3) hydroxyl, and
  (4) pyridine,
(b) aryl selected from phenyl or naphthyl,
(c) —C$_{1-2}$alkylaryl,
(d) heteroaryl, and
(e) —C$_{1-2}$alkylheteroaryl,
wherein the heteroaryl, aryl and heterocycle of choices (b), (c), (d) and (e) are optionally substituted with 1, 2 or 3 substituents independently selected from the group consisting of
  (1) halo, selected from Fluoro and Chloro
  (2) —CF$_3$,
  (3) —C$_{1-4}$alkyl,
  (4) —OC$_{1-4}$alkyl,
  (5) —C(O)—NH$_2$, and
  (6) —C(O)—O—C$_{1-4}$alkyl.

Within this aspect there is a genus wherein
R$^2$ is selected from the group consisting of:
(a) H,
(b) OH,
(c) C$_{1-8}$alkyl, optionally mono-, di- or tri substituted with substituents independently selected from
  (1) halo,
  (2) hydroxyl,
  (3) oxo,
  (4) —CN,
  (5) CHF$_2$,
  (6) CF$_3$,
  (7) pyridyl, and
  (8) —O—S(O)$_2$—C$_{1-2}$alkyl-CF$_3$;
(d) C$_{2-6}$alkenyl, optionally mono-, di- or tri substituted with fluoro,
(e) —C$_{1-2}$alkylC$_{3-6}$cycloalkyl,
(f) heterocycle,
(g) —C$_{1-2}$alkylheterocycle,
(h) aryl selected from phenyl or naphthyl,
(i) —C$_{1-2}$alkylaryl,
(j) —C$_{2-4}$alkenylaryl,
(k) heteroaryl,
(l) —C$_{1-2}$alkylheteroaryl,
(m) —CH$_2$pyridyl,
(o) —C1-4alkyl-O—C1-6alkyl, optionally substituted with hydroxy, or —O—S(O)$_2$—C$_{1-2}$alkyl-CF$_3$,
wherein the cycloalkyl, heteroaryl, aryl and heterocycle of choices (e), (f), (g), (h), (i), (j), (k), (l) and (m) are optionally substituted with 1, 2 or 3 substituents independently selected from the group consisting of
  (1) hydroxyl,
  (2) halo,
  (3) —CN,
  (4) —CF$_3$,
  (5) —C$_{1-4}$alkyl,
  (6) —OCH$_3$,
  (7) —O—CH$_2$CF$_3$,
  (8) —NH—C(O)—NH—CH$_3$,
  (9) —NH—C(O)—C$_{1-4}$alkyl,
  (10) —NH—C(O)—C$_{3-6}$cycloalkyl,
  (11) —C$_{1-3}$ alkyl-C(O)—OH,
  (12) —C$_{1-3}$alkyl-C(O)—O—CH$_3$,
  (13) —C(O)—NH$_2$,
  (14) —C(O)—C$_{1-4}$alkyl-N142,
  (15) —C(O)—NH—C$_{3-6}$cycloalkyl,
  (16) —C(O)—OH,
  (17) —C(O)—O—C$_{1-4}$alkyl,
  (18) —C$_{1-2}$alkyl-heterocycle,
  (19) —C$_{2-4}$alkenyl-C(O)-phenyl, and
  (20) —O—S(O)2-C$_{1-2}$alkyl-CF$_3$.

Within this genus there is a sub-genus wherein
R$^2$ is selected from the group consisting of
(a) H
(b) OH,
(c) C$_{1-8}$alkyl, optionally mono-, di- or tri substituted with substituents independently selected from
  (1) halo,
  (2) hydroxyl,
  (3) oxo,
  (4) —CN,
  (5) CHF$_2$,
  (6) CF$_3$, and
  (7) —O—S(O)$_2$—C$_{1-2}$alkyl-CF$_3$;
(d) —C$_{1-2}$alkylC$_{3-6}$cycloalkyl,
(e) —C$_{1-2}$alkylheterocycle,
(f) aryl selected from phenyl or naphthyl,
(g) —C$_{1-2}$alkylaryl,
(h) heteroaryl,
(i) —C$_{1-2}$alkylheteroaryl,
(j) —C$_{1-4}$alkyl-O—CH$_3$,
wherein the cycloalkyl, heteroaryl, aryl and heterocycle of choices (d), (e), (f), (g), (h) and (i) are optionally substituted with 1, 2 or 3 substituents independently selected from the group consisting of
  (1) hydroxyl,
  (2) halo,
  (3) —CN,
  (4) —CF$_3$,
  (5) —C$_{1-4}$alkyl,
  (6) —OCH$_3$,
  (7) —O—CH$_2$CF$_3$,
  (8) —NH—C(O)—NH—CH$_3$,
  (9) —NH—C(O)—C1.4alkyl,
  (10) —NH—C(O)—C$_{3-6}$cycloalkyl,
  (11) —C$_{1-3}$alkyl-C(O)—OH,
  (12) —C$_{1-3}$alkyl-C(O)—O—CH$_3$,
  (13) —C(O)—NH$_2$,
  (14) —C(O)—C$_{1-4}$alkyl-NH$_2$,
  (15) —C(O)—NH—C$_{3-6}$cycloalkyl,
  (16) —C(O)—OH,
  (17) —C(O)—O—C$_{1-4}$alkyl,
  (18) —C$_{1-2}$alkyl-heterocycle,
  (19) —C$_{2-4}$alkenyl-C(O)-phenyl, and
  (20) —O—S(O)$_2$—C$_{1-2}$alkyl-CF$_3$.

Within this sub-genus there is a class of compounds wherein
R$^2$ is selected from the group consisting of:
(a) H,
(b) OH,
(c) C$_{1-8}$alkyl, optionally mono-, di- or tri substituted with substituents independently selected from
  (1) halo,
  (2) hydroxyl,
  (3) CHF$_2$,
  (4) CF$_3$, and
  (5) —O—S(O)$_2$—C$_{1-2}$alkyl-CF$_3$;

(d) —C$_{1-2}$alkylC$_{3-6}$cycloalkyl,
(e) aryl selected from phenyl or naphthyl,
(f) —C$_{1-2}$alkylaryl,
(g) —C$_{1-2}$alkylheteroaryl,
(h) —C$_{1-4}$alkyl-O—CH$_3$, wherein the cycloalkyl, heteroaryl, aryl and heterocycle of choices (d), (e), (f), (g), (h) and (i) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OCH$_3$,
(7) —O—CH$_2$CF$_3$, and
(8) —O—S(O)$_2$—C$_{1-2}$alkyl-CF$_3$.

Within this aspect there is a genus of compounds wherein R$^3$ is selected from
(a) H, and
(b) C$_{1-6}$alkyl.

Within this genus there is a sub-genus wherein R$^3$ is hydrogen.

Within this aspect there is a genus of compounds wherein: R$^4$ is F.

Within this aspect there is a genus of compounds of Formula II

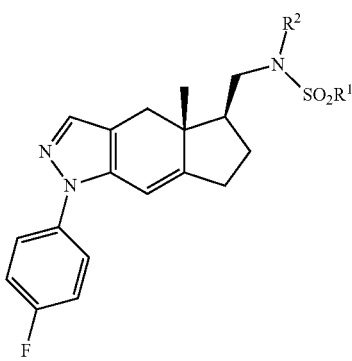

or a pharmaceutically acceptable salt thereof wherein
R$^1$ is selected from the group consisting of:
(a) C$_{1-6}$alkyl, optionally mono-, di- or tri substituted with substituents independently selected from
(1) halo selected from fluoro and chloro,
(2) —CF$_3$,
(3) hydroxyl, and
(4) pyridine,
(b) aryl selected from phenyl or naphthyl,
(c) —C$_{1-2}$alkylaryl,
(d) heteroaryl,
(e) —C$_{1-2}$alkylheteroaryl, wherein the heteroaryl, aryl and heterocycle of choices (b), (c), (d) and (e) are optionally substituted with 1, 2 or 3 substituents independently selected from the group consisting of
(1) halo, selected from fluoro and chloro,
(2) —CF$_3$,
(3) —C$_{1-4}$alkyl,
(4) —OC$_{1-4}$alkyl,
(5) —C(O)—NH$_2$, and
(6) —C(O)—O—C$_{1-4}$alkyl; and R$^2$ is selected from the group consisting of:
(a) H,
(b) OH,
(c) C$_{1-8}$alkyl, optionally mono-, di- or tri substituted with substituents independently selected from
(1) halo,
(2) hydroxyl,
(3) CHF$_2$,
(4) CF$_3$, and
(5) —O—S(O)$_2$—C$_{1-2}$alkyl-CF$_3$;
(d) —C$_{1-2}$alkylC$_{3-6}$cycloalkyl,
(e) aryl selected from phenyl or naphthyl,
(f) —C$_{1-2}$alkylaryl,
(g) —C$_{1-2}$alkylheteroaryl,
(h) —C$_{1-4}$alkyl-O—CH$_3$, wherein the cycloalkyl, heteroaryl, aryl and heterocycle of choices (d), (e), (f), (g), (h) and (i) are optionally substituted with 1, 2 or 3 substituents independently selected from the group consisting of
(1) hydroxyl,
(2) halo,
(3) —CN,
(4) —CF$_3$,
(5) —C$_{1-4}$-alkyl, and
(6) —OCH$_3$.

Within this genus there is a sub-genus of compounds wherein
R$^1$ is selected from the group consisting of:
(a) C$_{1-6}$alkyl, optionally mono-, di- or tri substituted with substituents independently selected from
(1) halo selected from fluoro and chloro,
(2) —CF$_3$,
(3) hydroxyl, and
(4) pyridine,
(b) aryl selected from phenyl or naphthyl,
(c) —C$_{1-2}$alkylaryl,
(d) heteroaryl, and
(e) —C$_{1-2}$alkylheteroaryl, wherein the heteroaryl, aryl and heterocycle of choices (h), (c), (d) and (e) are optionally substituted with 1, 2 or 3 substituents independently selected from the group consisting of
(1) halo, selected from Fluoro and Chloro
(2) —CF$_3$,
(3) —C$_{1-4}$alkyl,
(4) —OC$_{1-4}$alkyl,
(5) —C(O)—NH$_2$, and
(6) —C(O)—O—C$_{1-4}$alkyl; and R$^2$ is selected from the group consisting of:
(a) H,
(b) OH,
(c) C$_{1-8}$alkyl, optionally mono-, di- or tri substituted with substituents independently selected from
(1) halo,
(2) hydroxyl,
(3) CHF$_2$,
(4) CF$_3$, and
(5) —O—S(O)$_2$—C$_{1-2}$alkyl-CF$_3$,
(d) —C$_{1-2}$alkylC$_{3-6}$cycloalkyl,
(e) aryl selected from phenyl or naphthyl,
(f) —C$_{1-2}$alkylaryl,
(g) —C$_{1-2}$alkylheteroaryl,
(h) —C$_{1-4}$alkyl-O—CH$_3$, wherein the cycloalkyl, heteroaryl, aryl and heterocycle of choices (d), (e), (f), (g), (h) and (i) are optionally substituted with 1, 2 or 3 substituents independently selected from the group consisting of
(1) halo,
(2) —CF$_3$,
(3) —C$_{1-4}$alkyl, and
(4) —OCH$_3$.
or a pharmaceutically acceptable salt thereof.

Another embodiment of the invention encompasses a pharmaceutical composition comprising a compound of Formula I in combination with a pharmaceutically acceptable carrier.

Another embodiment of the invention encompasses a method for treating a glucocorticoid receptor mediated disease or condition in a mammalian patient in need of such treatment comprising administering the patient a compound of Formula I in an amount that is effective for treating the glucocorticoid receptor mediated disease or condition.

Within this embodiment is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitus, erythema nodosum, acne, hirsutism, toxic epidenual necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another embodiment of the invention encompasses a method of selectively modulating the activation, repression, agonism and antagonism effects of the glucocorticoid receptor in a mammal comprising administering to the mammal a compound of Formula I in an amount that is effective to modulate the glucocorticoid receptor.

Exemplifying the invention are the compounds of the Examples disclosed hereunder.

Definitions

The invention is described using the following definitions unless otherwise indicated.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Fluoroalkyl" means alkyl as defined above wherein one or more of the hydrogen atoms are replaced with a fluoro atom, up to the maximum number of substitutable positions.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic saturated carbocyclic rings having the indicated number of carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, adamantanyl and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b) pyridyl, quinolyl, indolyl, isoquinolyl, and the like.

"Heterocyclyl" or "heterocycle" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

Abbreviations

The following abbreviations have the indicated meanings:

| | |
|---|---|
| AIBN = | 2.2'-azobisisobutyronitrile |
| B.P. = | benzoyl peroxide |
| Bn = | benzyl |
| CCl$_4$ = | carbon tetrachloride |
| D = | —O(CH$_2$)$_3$O— |
| DAST = | diethylamine sulfur trifluoride |
| DCC = | dicyclohexyl carbodiimide |
| DCI = | 1-(3-dimethylaminopropyl)-3-ethyl carbodiimide |

-continued

| | |
|---|---|
| DEAD = | diethyl azodicarboxylate |
| DIBAL = | diisobutyl aluminum hydride |
| DME = | ethylene glycol dimethylether |
| DMAP = | 4-(dimethylamino)pyridine |
| DMF = | N,N-dimethylformamide |
| DMSO = | dimethyl sulfoxide |
| $Et_3N$ = | triethylamine |
| LDA = | lithium diisopropylamide |
| m-CPBA = | metachloroperbenzoic acid |
| NBS = | N-bromosuccinimide |
| NSAID = | non-steroidal anti-inflammatory drug |
| PCC = | pyridinium chlorochromate |
| PDC = | pyridinium dichromate |
| Ph = | phenyl |
| 1,2-Ph = | 1,2-benzenediyl |
| Pyr = | pyridinediyl |
| Qn = | 7-chloroquinolin-2-yl |
| $R^s$ = | —$CH_2SCH_2CH_2Ph$ |
| r.t. = | room temperature |
| rac. = | racemic |
| THF = | tetrahydrofuran |
| THP = | tetrahydropyran-2-yl |

Alkyl group abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amities including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Dose Ranges

It will be understood that, as used herein, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of glucocorticoid receptor mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Utilities

The ability of the compounds of Formula I to selectively modulate glucocorticoid receptors makes them useful for treating, preventing or reversing the progression of a variety of inflammatory and autoimmune diseases and conditions. Thus, the compounds of the present invention are useful to treat, prevent or ameliorate the following diseases or conditions: inflammation, tissue rejection, auto-immunity, various malianancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity and metabolic syndrome.

The compounds of the present invention are also useful for treating, preventing or reversing the progression of disease states involving systemic inflammation such as inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma.

The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IL-1 expression, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

Preferably, the compounds of the invention are useful for treating the diseases or conditions set for the below.

1. Allergic States

Control of severe or incapacitating allergic conditions not responsive to adequate trials of conventional treatment; seasonal or perennial allergic rhinitis; bronchial asthma; contact dermatitis; atopic dermatitis; serum sickness; and drug hypersensitivity reactions.

2. Rheumatic Disorders

As adjunctive therapy for short-term administration during an acute episode or exacerbation of: psoriatic arthritis; rheumatoid arthritis including juvenile rheumatoid arthritis (selected cases may require low-dosemaintenance therapy); ankylosing spondylitis; acute and subacute bursitis; acute nonspecific tenosynovitis; acute gouty arthritis; post-traumatic osteoarthritis; synovitis of osteoarthritis; and epicondylitis 3. Dermatologic Diseases Pemphigus; bullous dermatitis herpetiformis; severe erythema multiforme (Stevens-Johnson syndrome); exfoliative dermatitis; mycosis fungoïdes; severe psoriasis; and severe seborrheic dermatitis.

4. Ophthalmic Diseases

Severe acute and chronic allergic and inflammatory processes involving the eye and its adnexa such as: allergic conjunctivitis; keratitis; allergic corneal marginal ulcers; herpes zoster ophthalmicus; iritis and iridocyclitis; chorioretinitis; anterior segment inflammation; diffuse posterior uveitis and choroiditis; optic neuritis; and sympathetic ophthalmia.

5. Endocrine Disorders

Primary or secondary adrenocortical insufficiency; congenital adrenal hyperplasia; nonsuppurative thyroiditis; and hypercalcemia associated with cancer.

6. Respiratory Diseases

Symptomatic sarcoidosis; Löffler's syndrome not manageable by other means; berylliosis; fulminating or disseminated pulmonary tuberculosis when concurrently accompanied by appropriate antituberculous chemotherapy; and aspiration pneumonitis.

7. Hematologic Disorders

Idiopathic thrombocytopenic purpura in adults; secondary thrombocytopenia in adults; acquired (autoimmune) hemolytic anemia; erythroblastopenia (RBC anemia); and congenital (erythroid) hypoplastic anemia.

8. Neoplastic Diseases

For palliative management of: leukemias and lymphomas in adults; and acute leukemia of childhood.

9. Edematous States

To induce a diuresis or remission of proteinuria in the nephrotic syndrome without uremia, of the idiopathic type or that due to lupus erythematosus. Compounds of Formula I may be used to treat patients with cerebral edema from various causes. It may be used also in the preoperative preparation of patients with increased intracranial pressure secondary to brain tumors, and also for palliation of patients with inoperable or recurrent brain neoplasms, and in the management of cerebral edema associated with neurosurgery. Some patients with cerebral edema due to head injury or pseudotumor cerebri also may benefit from therapy with compounds of Formula I.

10. Gastrointestinal Diseases

During a critical period of the disease in: ulcerative colitis and regional enteritis.

11. Miscellaneous

Tuberculous meningitis with subarachnoid block or impending block when concurrently accompanied by appropriate antituberculous chemotherapy; Trichinosis with neurologic or myocardial involvement; During an exacerbation or as maintenance therapy in selected cases of: Systemic lupus erythematosus and acute rheumatic carditis; in combination with ondansetron for the management of nausea and vomiting associated with cisplatin and non-cisplatin emetogenic chemotherapy.

Combination Therapy

The invention also encompasses a method for treating a glucocorticoid receptor mediated disease comprising concomitantly administering to a patient in need of such treatment a compound of Formula I and one or additional more agents. For treating or preventing asthma or chronic obstructive pulmonary disease, the compounds of Formula I may be combined with one or more agents selected from the group consisting of: θ-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formula I may be combined with one or the following: a salicylate, including acetylsalicylic acid, a non-steroidal antiinflammatory drug, including indomethacin, sulindac, mefenamic, meclofenamic, tolfenamic, tolmetin, ketorolac, dicofenac, ibuprofen, naproxen, fenoprofen, ketoprofen, flurbiprofin and oxaprozin, a TNF inhibitor, including etanercept and infliximab, an IL-1 receptor antagonist, a cytotoxic or immunosuppressive drug, including methotrexate, leflunomide, azathioprine and cyclosporine, a gold compound, hydroxychloroquine or sulfasalazine, penicillamine, darbufelone, and a p38 kinase inhibitor. The compound of Formula I may also be used in combination with bisphonates such as alendronate to treat a glucocorticoid mediated disease and simultaneously inhibit osteoclast-mediated bone resorption.

Methods of Synthesis and Examples

The invention will now be illustrated by the following non-limiting examples in which, unless stated otherwise:

(i) all operations were carried out at room or ambient temperature, that is, at a temperature in the range 18-25° C., (ii) evaporation of solvent was carried out using a rotary evaporator under reduced pressure (600-4000 pascals: 4.5-30 mm. Hg) with a bath temperature of up to 60° C., (iii) the course of reactions was followed by thin layer chromatography (TLC) and reaction times are given for illustration only;

(iv) melting points are uncorrected and indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis and Examples

Compounds of the invention can be synthesized by following the following general synthetic scheme.

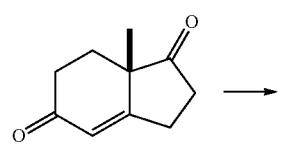

Organic Syntheses
Coll. Vol. 7,
p. 363; Vol 63, p. 26

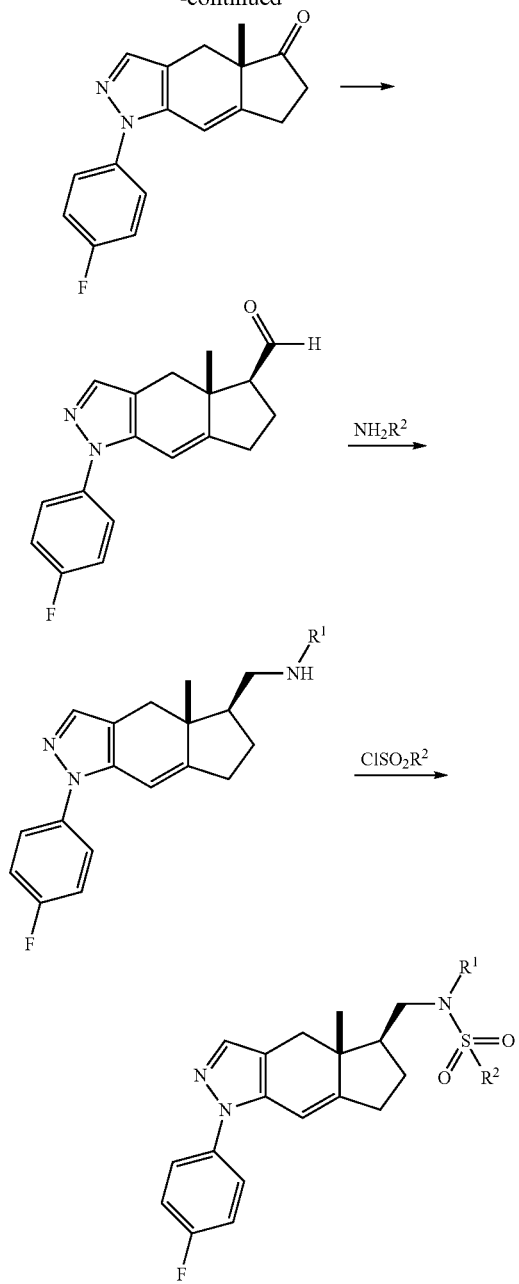

The invention will now be illustrated by the following non-limiting examples in which, unless stated otherwise:

(i) all operations were carried out at room or ambient temperature, that is, at a temperature in the range 18-25° C., (ii) evaporation of solvent was carried out using a rotary evaporator under reduced pressure (600-4000 pascals: 4.5-30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), imp, (melting point), L (liter(s)), L (milliliters), g (gram(s)), mg (milligrams(s)), mol (moles), mmol (millimoles), eq (equivalent(s)).

EXAMPLE 1

N-{[(4αR,5S)-1-(4-Fluorophenyl)-4α-methyl-1,4,4α,5,6,7-hexahydrocyclopenta[f]indazol-5-yl]methyl}-1-pyridin-3-yl-N-(2-pyridin-2-ylethyl)methanesulfonamide(1-8)

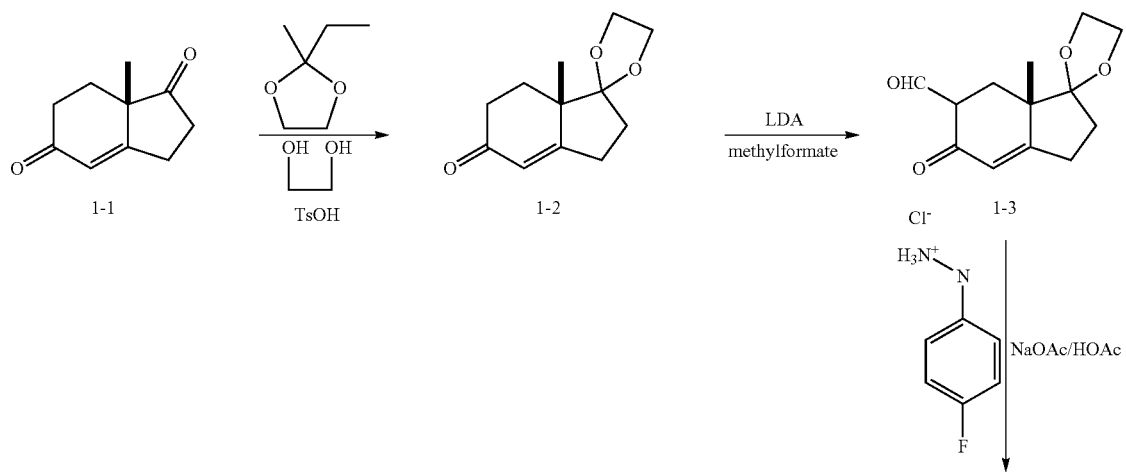

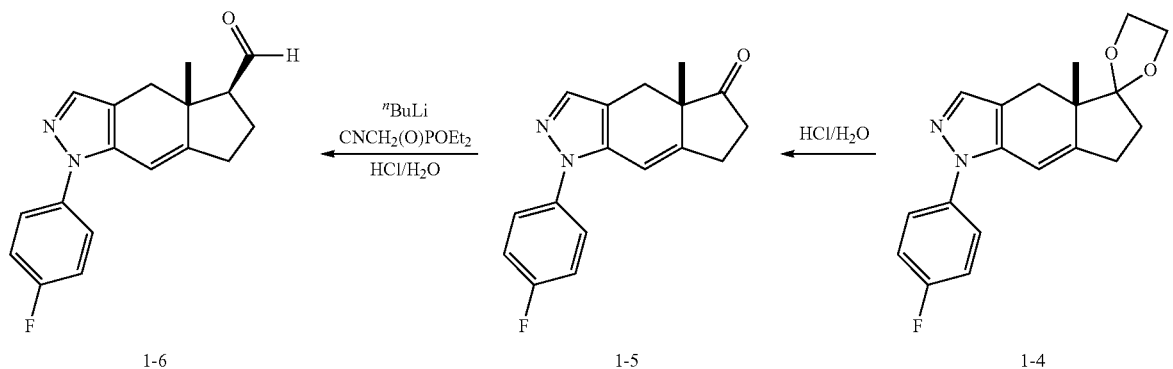

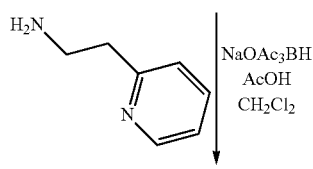

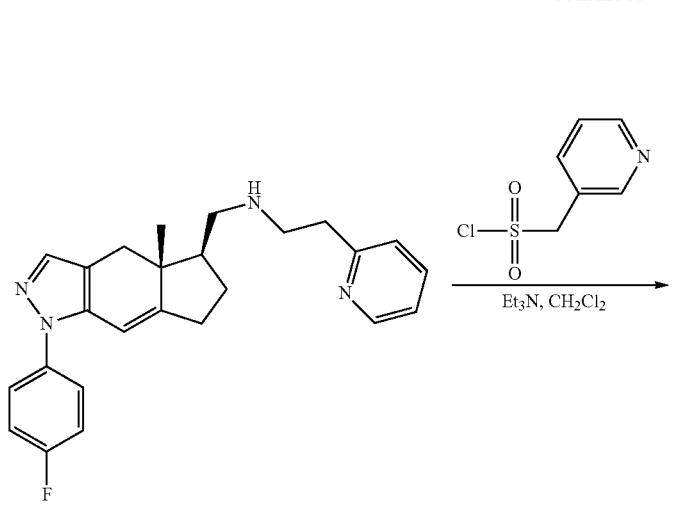

1-7

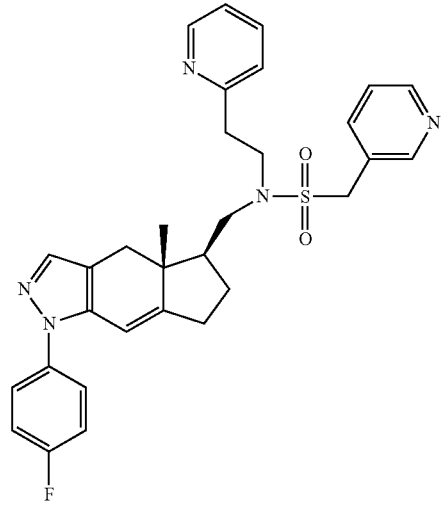

1-8

(7α'S)-7α'-Methyl-2',3',7',7α'-tetrahydrospiro[1,3-dioxolane-2,1'-inden]-5'(6'H)-one (1-2) Ethylene glycol (12.2 mL, 219 mmol) and p-toluenesulfonic acid monohydrate (4.40 g, 25.6 mmol) were added to a solution of Hajos-Parrish Ketone (See *Organic Syntheses*, Coll. Vol. 7, p. 363; Vol 63, p. 26) (1-1, 60.0 g, 365 mmol) in 2-ethyl-2-methyl-1,3-dioxolan (46 mL) and the resulting solution stirred at ambient temperature for 24 hours. The reaction was poured into saturated aqueous $NaHCO_3$ solution (1 L) and the crude product extracted with EtOAc (x3). The combined organic extracts were dried over anhydrous $MgSO_4$ and the solvent removed in vacuo. Purification by flash chromatography on 1.5 kg of silica, eluting with a gradient of 0-70% EtOAc in hexanes afforded 48.5 g, 64% of 1-2 as a clear viscous oil.

MS (ESI): m/z=209.3 ($MH^+$).

(7α'S)-7α'-Methyl-5'-oxo-2',3',5',6',7',7α'-hexahydrospiro[1,3-dioxolane-2,1'-indene]-6'-carbaldehyde (1-3)

A 1.5 M solution of lithium diisopropylamide mono(tetrahydrofuran) in cyclohexane (465 mL, 0.698 mol) was added to a solution of 1-2 (48.5 g, 0.233 mol) in diethyl ether (930 mL) at −78° C. and the resulting solution stirred at this temperature for 1 hour to afford a thick suspension. Methyl formate (86.6 mL, 1.40 mol) was added dropwise over about 30 min and the resulting suspension stirred at −78° C. for 5 hours. The reaction was quenched at −78° C. with 1 M aqueous HCl solution (3 L) and the aqueous layer checked to ensure it was acidic. The crude product was extracted with EtOAc (x3) and the combined organic extracts were dried over anhydrous $MgSO_4$ and the solvent removed in vacuo to afforded 60 g of crude 1-3 (74% pure) as a tan viscous oil that was used directly in the next step without purification.

MS (ESI): m/z=237.3 ($MH^+$).

(4αS)-1-(4-Fluorophenyl)-4α-methyl-4,4α,6,7-tetrahydrocyclopenta[f]indazol-5(1H)-one (1-5)

Sodium acetate (38.2 g, 0.465 mol) was added to a solution of crude 1-3 (60 g), p-fluorophenylhydrazine hydrochloride (47.3 g, 0.291 mol) and acetic acid (66.6 mL, 1.16 mol) in toluene (465 mL) and the resulting suspension heated at 100° C. for 1 hour. The reaction was cooled to ambient temperature, diluted with EtOAc, and washed carefully ($CO_2$ evolution!) with aqueous 5% w/v $NaHCO_3$ solution (2×μL), then dried over anhydrous $MgSO_4$ and concentrated to afford a viscous brown oil. The crude oil was dissolved in THF (1 L) and aqueous 6M HCl (155 mL) was added and the resulting solution was heated to 65° C. for 3.5 hours. The resulting solution was cooled to ambient temperature, and poured slowly into aqueous 5% w/v $NaHCO_3$ solution ($CO_2$ evolution!), and the crude product was extracted with EtOAc (x3). The combined organic extracts were dried over anhydrous $MgSO_4$ and the solvent removed in vacuo. Purification by flash chromatography on 1.5 kg of silica, eluting with a gradient of 0-50% EtOAc in hexanes afforded 48.3 g of 1-5, 74% from 1-3, as a viscous brown oil that solidified on standing for several days.

MS (ESI): m/z=2833 ($MH^+$).

(4αR,5S)-1-(4-Fluorophenyl)-4α-methyl-1,4,4α,5,6,7-hexahydrocyclopenta[f]indazole-5-carbaldehyde (1-6)

A 1.6 M solution of nBuLi in hexanes (6.4 mL, 16.0 mmol) was added to a solution of diethyl isocyanomethylphosphonate (2.6 mL, 16.0 mmol) in anhydrous THF (30 mL) at −78° C. and the resulting solution stirred at this temperature for 30 min. A solution of 1-5 (3.0 g, 10.6 mmol) in anhydrous THF (10 mL) was added dropwise over about 20 min and the resulting solution was stirred at −78° C. for 1 hour, then warmed directly to ambient temperature and stirred for a further 1 hour. The reaction was quenched with saturated aqueous ammonium chloride solution, and the crude product was extracted with EtOAc (3×). The combined organic extracts were dried over anhydrous $MgSO_4$ and the solvent removed in vacuo. The vinyl isocyanate intermediate was dissolved in diethyl ether (50 mL) and 4M aqueous HCl (30 mL) was then added and the biphasic mixture was stirred at ambient temperature for 12 hours. The reaction was quenched with 1M aqueous HCl, and the crude product was extracted with EtOAc (3×). The combined organic extracts were dried over anhydrous $MgSO_4$ and the solvent removed in vacuo. This afforded 2.95 g, 94% of the product 1-6 as a thick, red oil.

MS (ESI): m/z=297.2 ($MH^+$).

N-{[(4αR,5S)-1-(4-fluorophenyl)-4α-methyl-1,4,4α,5,6,7-hexahydrocyclopenta[f]indazol-5-yl]methyl}-2-pyridin-2-ylethanamine) (1-7)

Sodium triacetoxyborohydride (7.15 g, 33.7 mmol) was added to a solution of 1-6 (5.0 g, 16.87 mmol), 2-(2-aminoethyl)pyridine (2.019 ml, 16.87 mmol) and acetic acid (0.966 ml, 16.87 mmol) in dichloromethane (15 mL) at room temperature. The reaction mixture was stirred at room temperature for 2 hours and until LC/MS showed the reaction is complete. The reaction was quenched by the addition of a saturated solution of sodium bicarbonate (25 mL) and extracted with dichloromethane (100 mL). The organic layer was washed with a 1N aqueous solution of sodium hydroxide, dried over anhydrous $MgSO_4$ and the solvent removed in vacuo. This afforded 5.8 g, 85% of the product 1-7 as a brown oil which was used without further purification.

MS (ESI): m/z=403.3 ($MH^+$).

N-{[(4αR,5S)-1-(4-fluorophenyl)-4α-methyl-1,4,4α,5,6,7-hexahydrocyclopenta[f]indazol-5-yl]methyl}-1-pyridin-3-yl-N-(2-pyridin-2-ylethyl)methanesulfonamide(1-8)

Pyridin-3-ylmethanesulfonyl chloride (2.148 g, 6.29 mmol) was added to a solution of 1-7 (2.53 g, 6.29 mmol) and triethylamine (0.876 ml, 6.29 mmol) at room temperature in dichloromethane (15 mL). The reaction mixture was stirred at room temperature for one hour and until LC/MS showed the reaction is complete. The solvent was removed in vacuo and the crude product was purified by reverse phase HPLC(C-18, 5-50% acetonitrile in water) which afforded 1.5 g, 42% of the product as a yellow solid.

HRMS (APCI): m/z=558.2311 ($MH^+$).

The following examples were prepared following the general synthetic scheme and procedures analogous to the examples described above.

| Ex. | STRUCTURE | NAME | M + 1 |
| --- | --- | --- | --- |
| 2 | 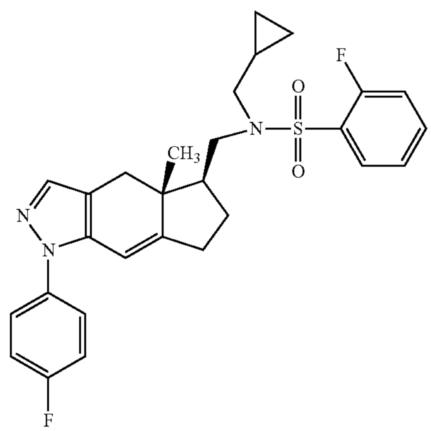 | N-(cyclopropylmethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 492.2429 |
| 3 | 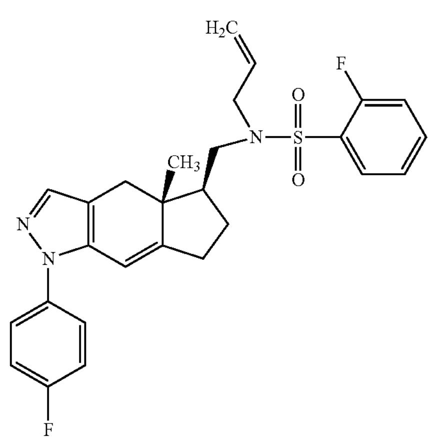 | N-allyl-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 470.1839 |

| Ex. | STRUCTURE | NAME | M + 1 |
|---|---|---|---|
| 4 | 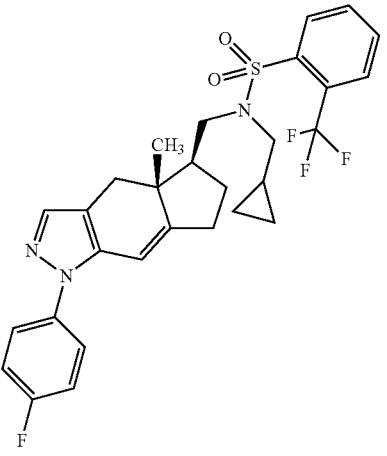 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide | 560.1991 |
| 5 | 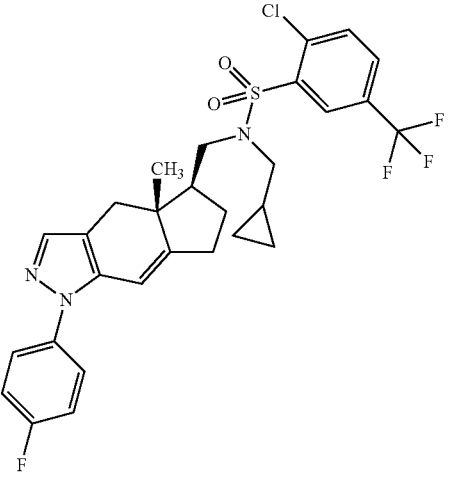 | 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-5-(trifluoromethyl)benzenesulfonamide | 594.1595 |
| 6 | 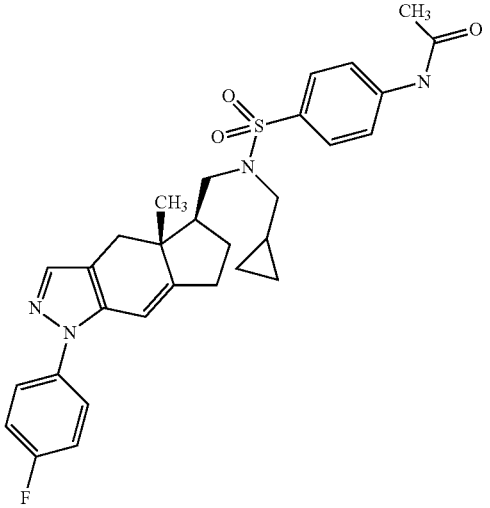 | N-{4-[((cyclopropylmethyl){[(4αR,5S)-1-(4-fluorophenyl)-4α-methyl-1,4,4α,5,6,7-hexahydrocyclopenta[f]indazol-5-yl]methyl}amino)sulfonyl]phenyl}acetamide | 549.2338 |

| Ex. | STRUCTURE | NAME | M + 1 |
|---|---|---|---|
| 7 | 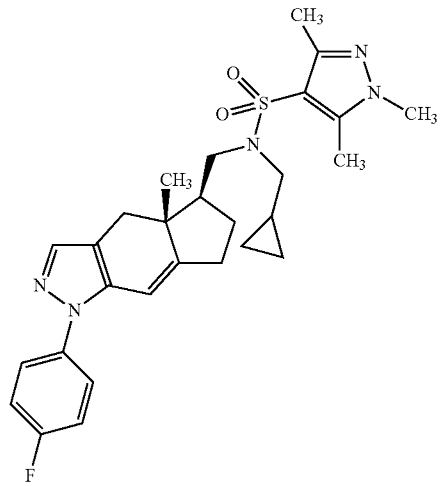 | (5-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-1,3-dimethyl-1H-pyrazole-4-sulfonamide | 544.195 |
| 8 | 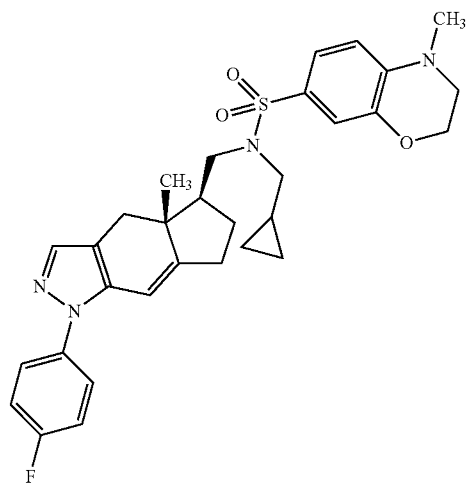 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-4-methyl-3,4-dihydro-2H-1,4-benzoxazine-7-sulfonamide | 563.2486 |
| 9 | 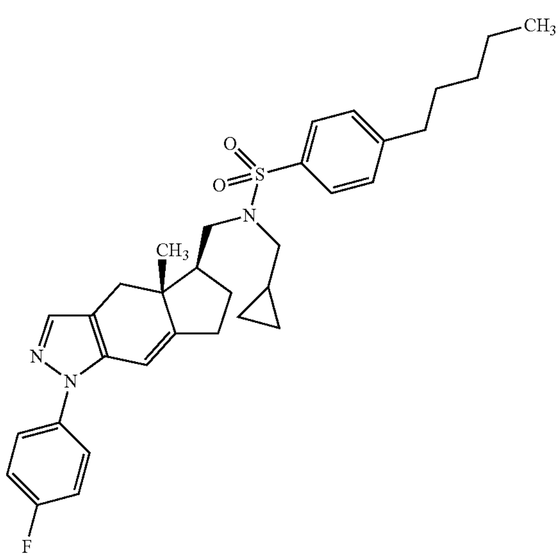 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-4-pentylbenzenesulfonamide | 562.291 |

| Ex. | STRUCTURE | NAME | M + 1 |
|---|---|---|---|
| 10 | 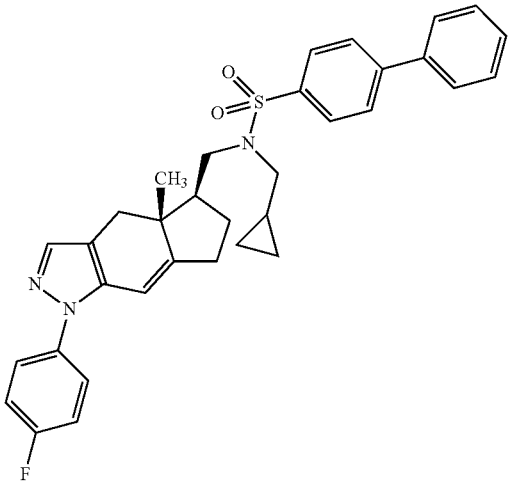 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}biphenyl-4-sulfonamide | 568.2433 |
| 11 | 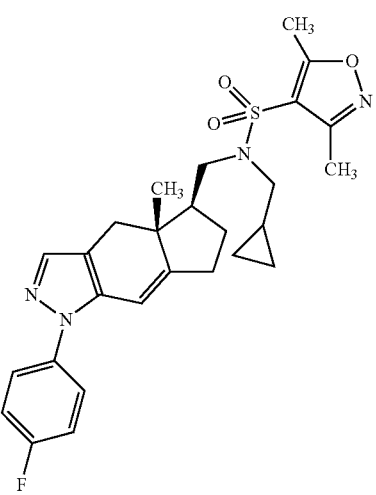 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide | 511.2178 |
| 12 | 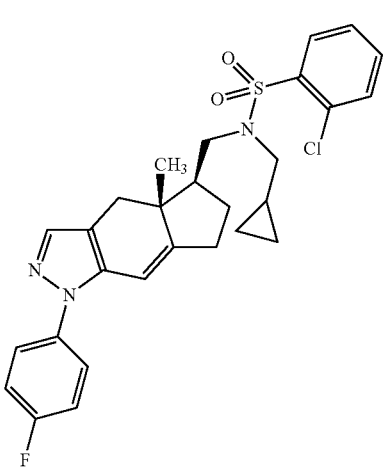 | 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 526.1737 |

-continued

| Ex. | STRUCTURE | NAME | M + 1 |
|---|---|---|---|
| 13 | 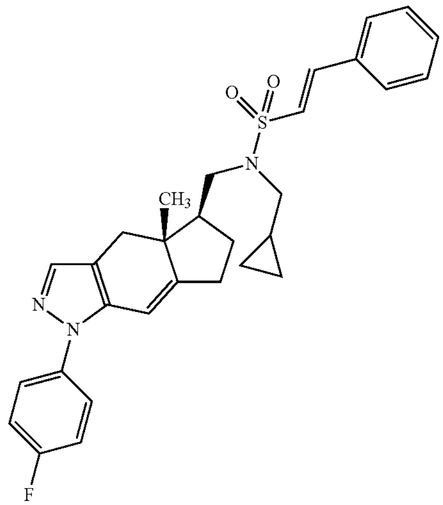 | (E)-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-2-phenylethylenesulfonamide | 518.2279 |
| 14 | 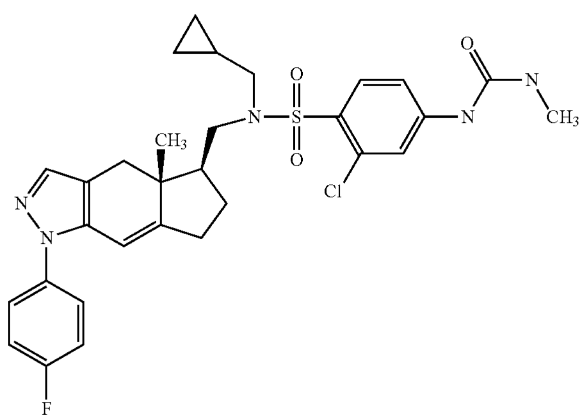 | 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-4-{[(methylamino)carbonyl]amino}-benzenesulfonamide | 598.2054 |
| 15 | 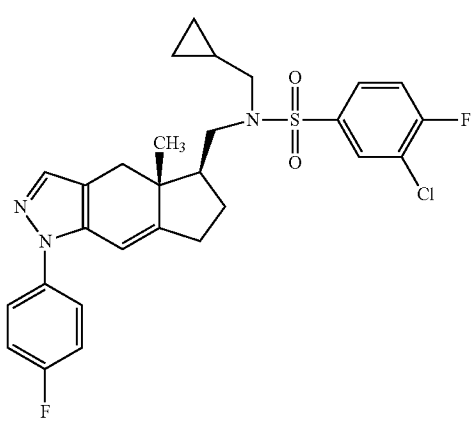 | 3-chloro-N-(cyclopropylmethyl)-4-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 544.164 |

| Ex. | STRUCTURE | NAME | M + 1 |
|---|---|---|---|
| 16 | 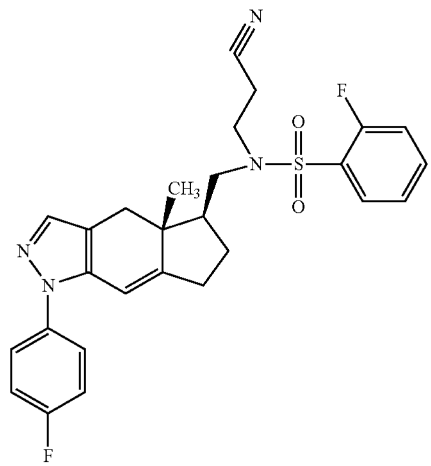 | N-(2-cyanoethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 508.595 |
| 17 | 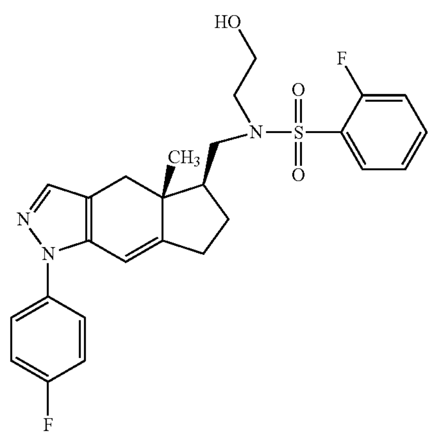 | 2-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 499.584 |
| 18 | 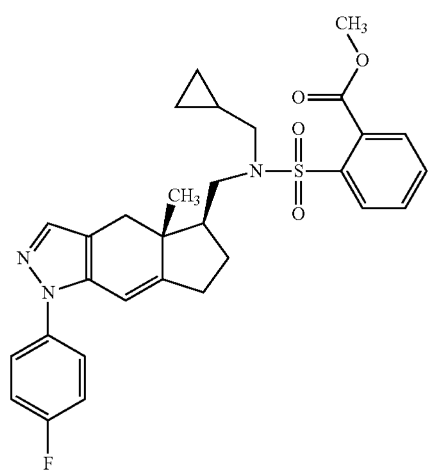 | methyl 2-[((cyclopropylmethyl){[(4αR,5S)-1-(4-fluorophenyl)-4α-methyl-1,4,4α,5,6,7-hexahydrocyclopenta[f]indazol-5-yl]methyl}amino)sulfonyl]benzoate | 549.67 |

-continued

| Ex. | STRUCTURE | NAME | M + 1 |
|---|---|---|---|
| 19 | 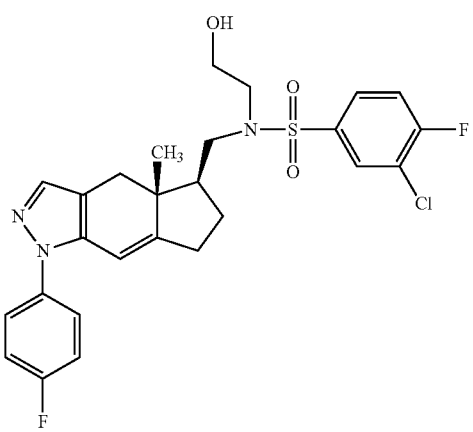 | 3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 534.029 |
| 20 | 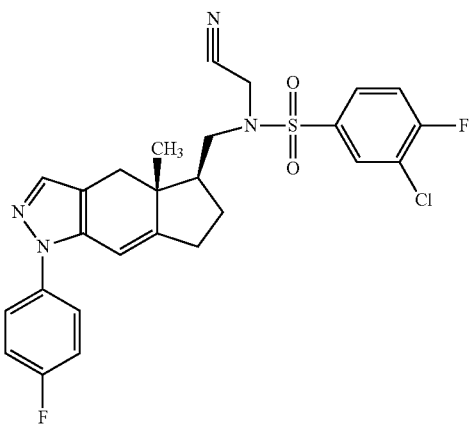 | 3-chloro-N-(cyanomethyl)-4-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 529.013 |
| 21 | 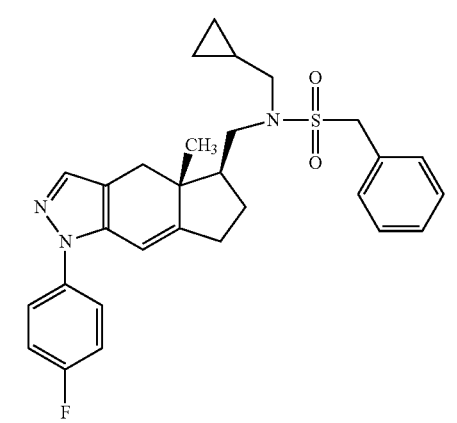 | N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-1-phenylmethanesulfonamide | 505.66 |

| Ex. | STRUCTURE | NAME | M + 1 |
|---|---|---|---|
| 22 | 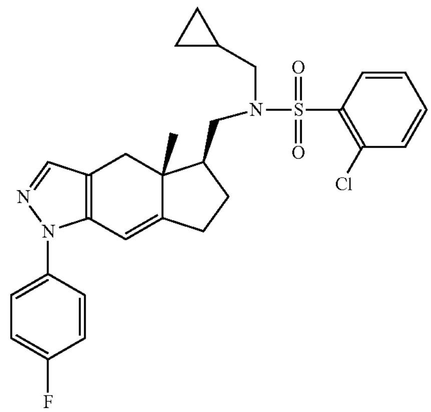 | 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 526.08 |
| 23 | 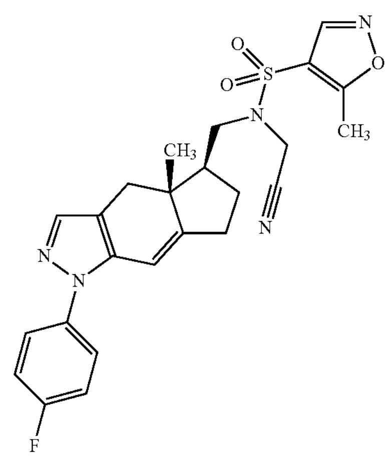 | N-(cyanomethyl)-N-{[(4αR,5S)-1-(4-fluorophenyl)-4α-methyl-1,4,4α,5,6,7-hexahydrocyclopenta[f]indazol-5-yl]methyl}-5-methylisoxazole-4-sulfonamide | 482.1626 |
| 24 | 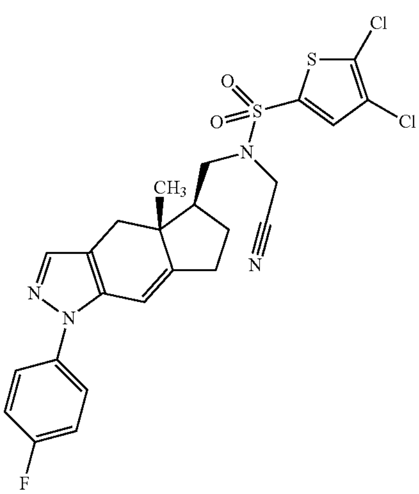 | 4,5-dichloro-N-(cyanomethyl)-N-{[(4αR,5S)-1-(4-fluorophenyl)-4α-methyl-1,4,4α,5,6,7-hexahydrocyclopenta[f]indazol-5-yl]methyl}thiophene-2-sulfonamide | 551.0498 |

-continued

| Ex. | STRUCTURE | NAME | M + 1 |
|---|---|---|---|
| 25 | 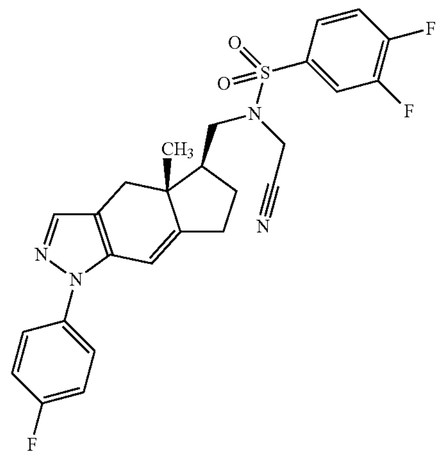 | N-(cyanomethyl)-3,4-difluoro-N-{[(4αR,5S)-1-(4-fluorophenyl)-4α-methyl-1,4,4α,5,6,7-hexahydrocyclopenta[f]indazol-5-yl]methyl}benzenesulfonamide | 513.1529 |
| 26 | 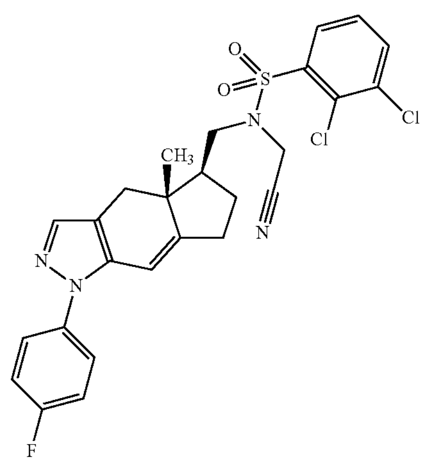 | 2,3-dichloro-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 545.0942 |
| 27 | 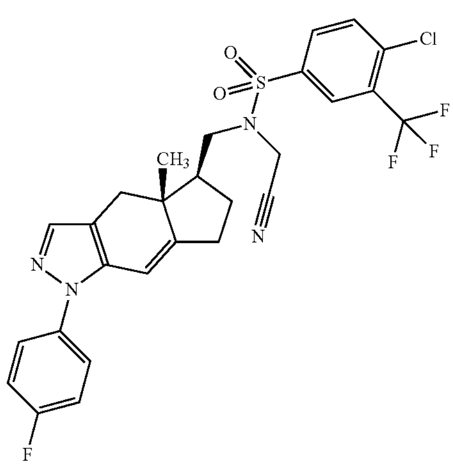 | 4-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}-3-(trifluoromethyl)benzenesulfonamide | 579.12 |

| Ex. | STRUCTURE | NAME | M + 1 |
|---|---|---|---|
| 28 | 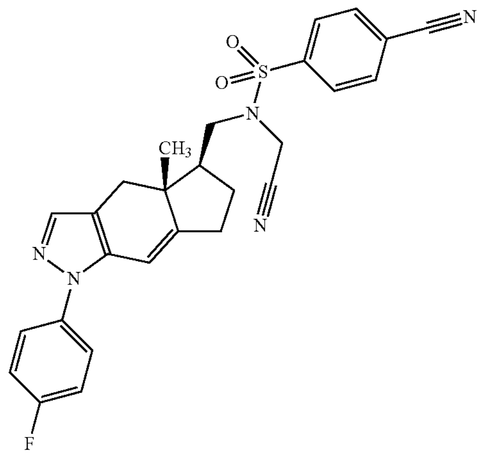 | 4-cyano-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 502.1674 |
| 29 | 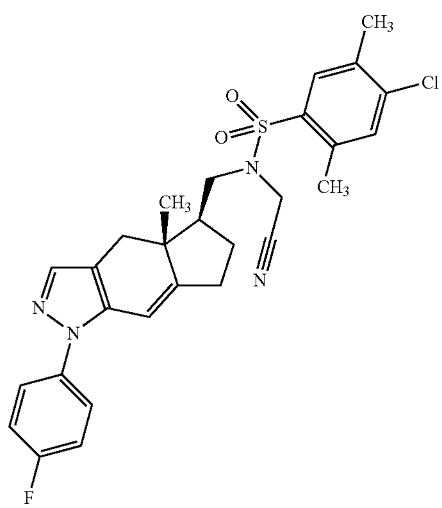 | 4-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}-2,5-dimethylbenzenesulfonamide | 539.1655 |
| 30 | 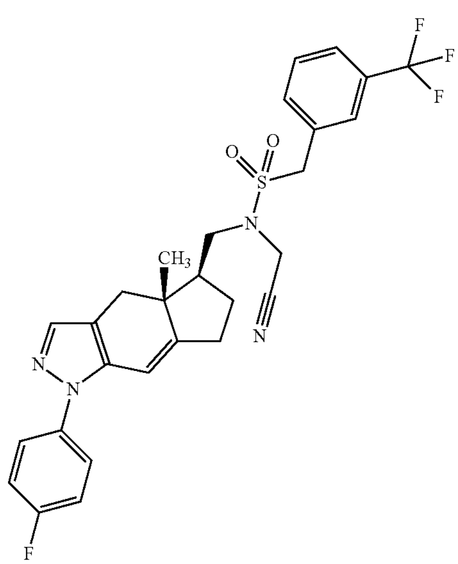 | N-(cyanomethyl)-N-{[(4αR,5S)-1-(4-fluorophenyl)-4α-methyl-1,4,4α,5,6,7-hexahydrocyclopenta[f]indazol-5-yl]methyl}-1-[3-(trifluoromethyl)phenyl]methanesulfonamide | 559.1739 |

| Ex. | STRUCTURE | NAME | M + 1 |
|---|---|---|---|
| 31 | 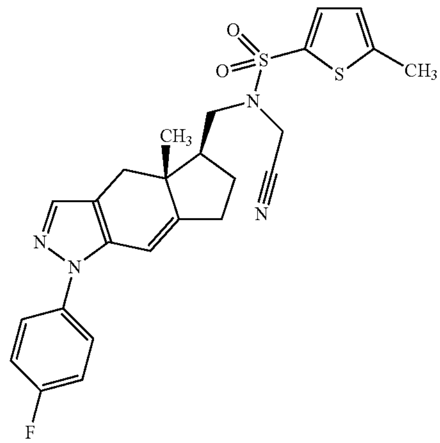 | N-(cyanomethyl)-N-{[(4αR,5S)-1-(4-fluorophenyl)-4α-methyl-1,4,4α,5,6,7-hexahydrocyclopenta[f]indazol-5-yl]methyl}-5-methylthiophene-2-sulfonamide | 497.1439 |
| 32 | 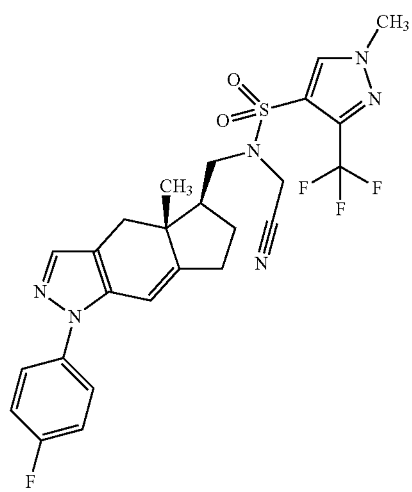 | N-(cyanomethyl)-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonamide | 549.1646 |
| 33 | 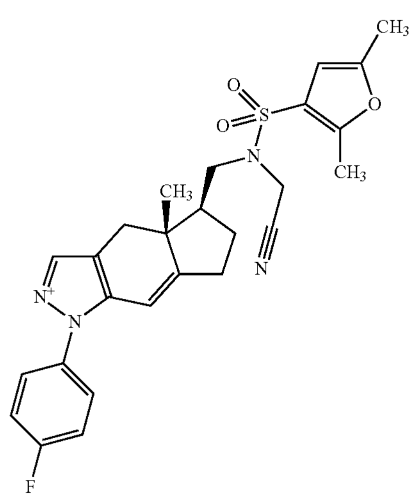 | (4αR,5S)-5-({(cyanomethyl)[(2,5-dimethyl-3-furyl)sulfonyl]amino}methyl)-1-(4-fluorophenyl)-4α-methyl-1,4,4α,5,6,7-hexahydrocyclopenta[f]indazol-2-ium | 495.1826 |

| Ex. | STRUCTURE | NAME | M + 1 |
|---|---|---|---|
| 34 | 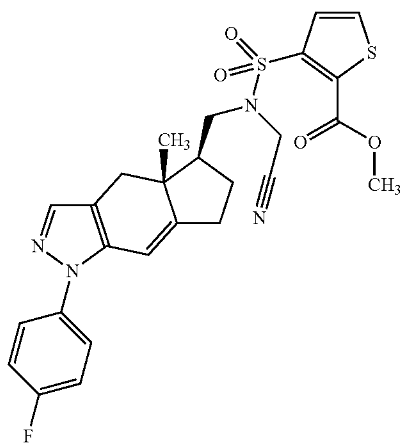 | methyl 3-[((cyanomethyl){[(4αR,5S)-1-(4-fluorophenyl)-4α-methyl-1,4,4α,5,6,7-hexahydrocyclopenta[f]indazol-5-yl]methyl}amino)sulfonyl]thiophene-2-carboxylate | 541.1336 |
| 35 | 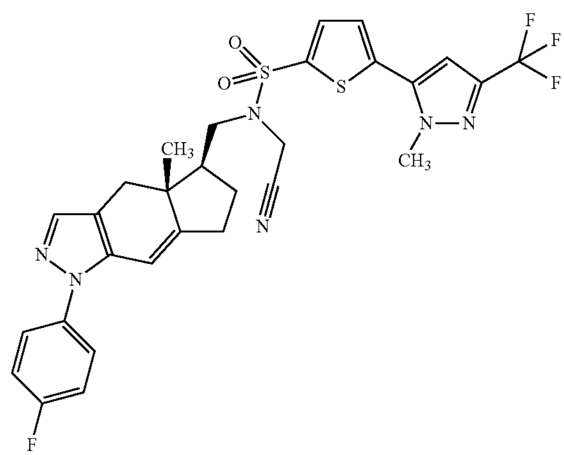 | (N-(cyanomethyl)-N-{[(4αR,5S)-1-(4-fluorophenyl)-4α-methyl-1,4,4α,5,6,7-hexahydrocyclopenta[f]indazol-5-yl]methyl}-5-[1-methyl-3-(trifluoromethyl)-1H-pyrazol-5-yl]thiophene-2-sulfonamide | 631.1535 |
| 36 | 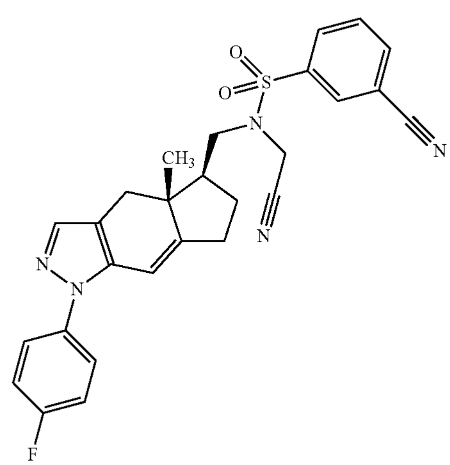 | 3-cyano-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 502.1674 |

-continued

| Ex. | STRUCTURE | NAME | M + 1 |
|---|---|---|---|
| 37 | 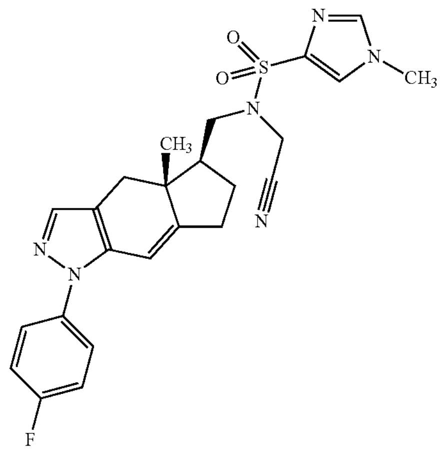 | N-(cyanomethyl)-N-{[(4αR,5S)-1-(4-fluorophenyl)-4α-methyl-1,4,4α,5,6,7-hexahydrocyclopenta[f]indazol-5-yl]methyl}-1-methyl-1H-imidazole-4-sulfonamide | 481.179 |
| 38 | 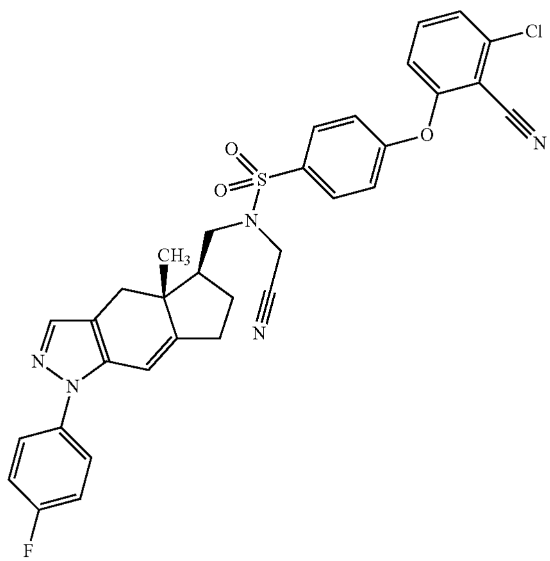 | 4-(3-chloro-2-cyanophenoxy)-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 628.1536 |
| 39 | 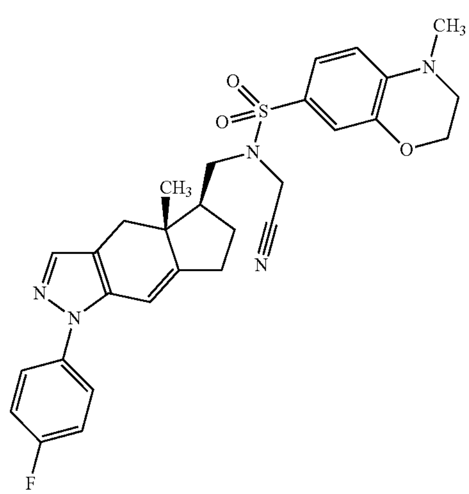 | N-(cyanomethyl)-N-{[(4αR,5S)-1-(4-fluorophenyl)-4α-methyl-1,4,4α,5,6,7-hexahydrocyclopenta[f]indazol-5-yl]methyl}-4-methyl-3,4-dihydro-2H-1,4-benzoxazine-7-sulfonamide | 548.2088 |

| Ex. | STRUCTURE | NAME | M + 1 |
|---|---|---|---|
| 40 | 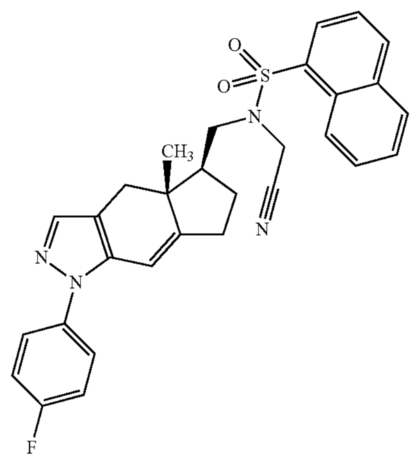 | N-(cyanomethyl)-N-{[(4αR,5S)-1-(4-fluorophenyl)-4α-methyl-1,4,4α,5,6,7-hexahydrocyclopenta[f]indazol-5-yl]methyl}naphthalene-1-sulfonamide | 527.1877 |
| 41 | 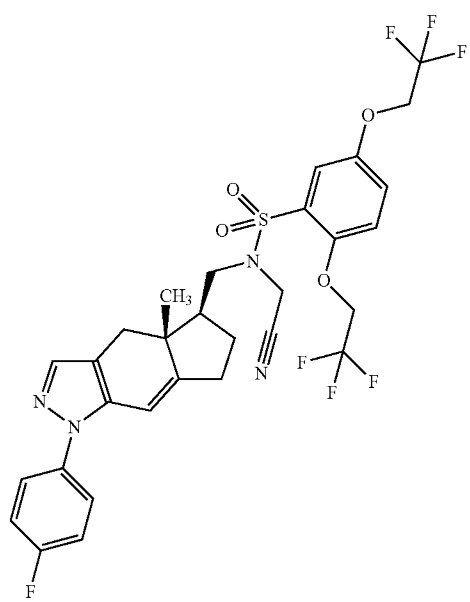 | N-(cyanomethyl)-N-{[(4αR,5S)-1-(4-fluorophenyl)-4α-methyl-1,4,4α,5,6,7-hexahydrocyclopenta[f]indazol-5-yl]methyl}-2,5-bis(2,2,2-trifluoroethoxy)benzenesulfonamide | 673.1648 |
| 42 | 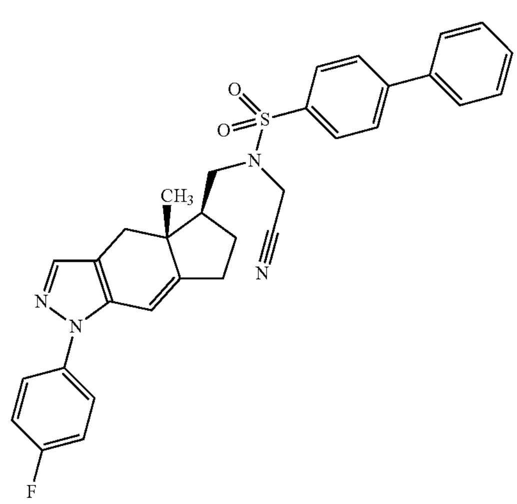 | N-(cyanomethyl)-N-{[(4αR,5S)-1-(4-fluorophenyl)-4α-methyl-1,4,4α,5,6,7-hexahydrocyclopenta[f]indazol-5-yl]methyl}biphenyl-4-sulfonamide | 553.2036 |

-continued

| Ex. | STRUCTURE | NAME | M + 1 |
|---|---|---|---|
| 43 | 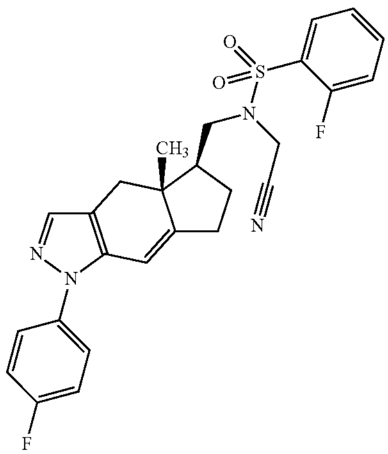 | N-(cyanomethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 495.1627 |
| 44 | 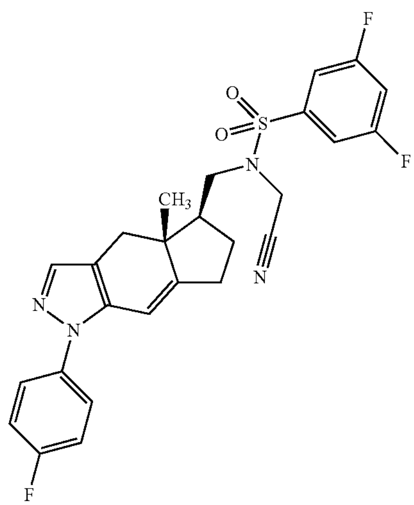 | N-(cyanomethyl)-3,5-difluoro-N-{[(4αR,5S)-1-(4-fluorophenyl)-4α-methyl-1,4,4α,5,6,7-hexahydrocyclopenta[f]indazol-5-yl]methyl}benzenesulfonamide | 513.1532 |
| 45 | 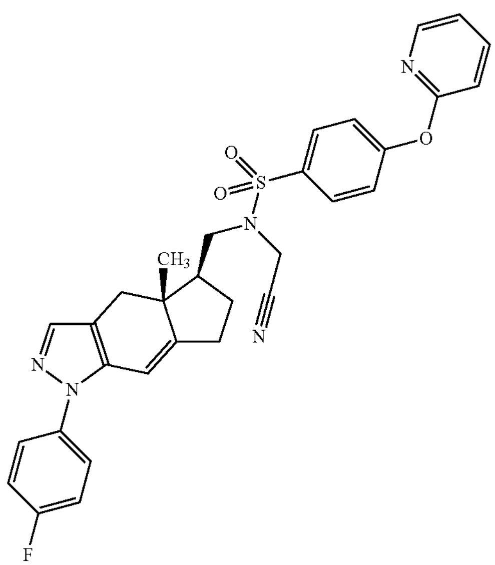 | N-(cyanomethyl)-N-{[(4αR,5S)-1-(4-fluorophenyl)-4α-methyl-1,4,4α,5,6,7-hexahydrocyclopenta[f]indazol-5-yl]methyl}-4-(pyridin-2-yloxy)benzenesulfonamide | 570.1924 |

-continued

| Ex. | STRUCTURE | NAME | M + 1 |
|---|---|---|---|
| 46 | 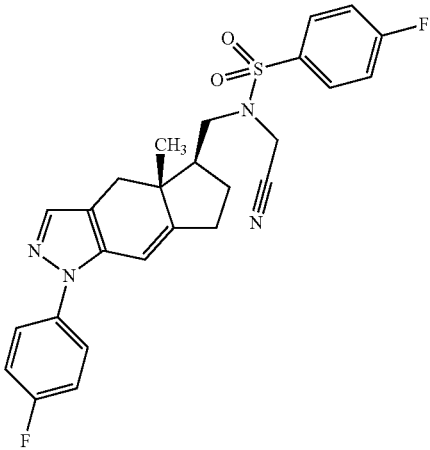 | N-(cyanomethyl)-4-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 495.1627 |
| 47 | 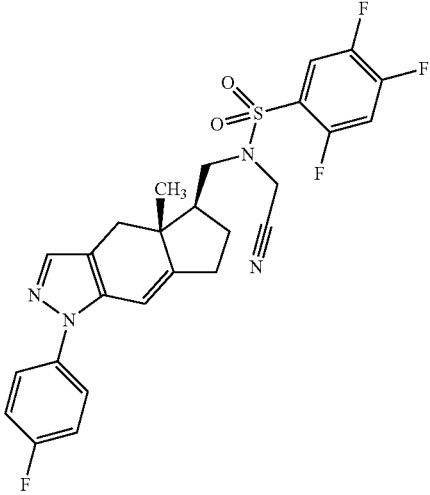 | N-(cyanomethyl)-2,4,5-trifluoro-N-{[(4αR,5S)-1-(4-fluorophenyl)-4α-methyl-1,4,4α,5,6,7-hexahydrocyclopenta[f]indazol-5-yl]methyl}benzenesulfonamide | 531.1435 |
| 48 | 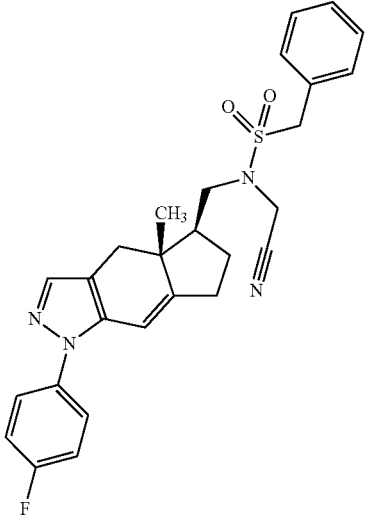 | N-(cyanomethyl)-N-{[(4αR,5S)-1-(4-fluorophenyl)-4α-methyl-1,4,4α,5,6,7-hexahydrocyclopenta[f]indazol-5-yl]methyl}-1-phenylmethanesulfonamide | 491.188 |

| Ex. | STRUCTURE | NAME | M + 1 |
|---|---|---|---|
| 49 | 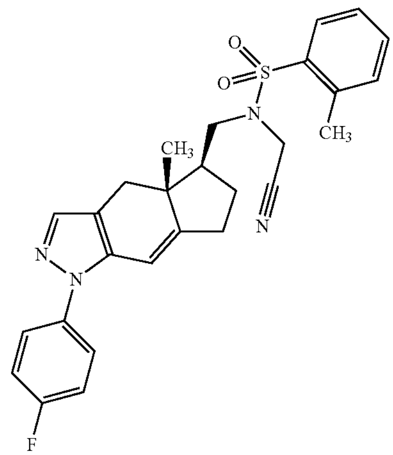 | N-(cyanomethyl)-N-{[(4αR,5S)-1-(4-fluorophenyl)-4α-methyl-1,4,4α,5,6,7-hexahydrocyclopenta[f]indazol-5-yl]methyl}-2-methylbenzenesulfonamide | 491.1882 |
| 50 | 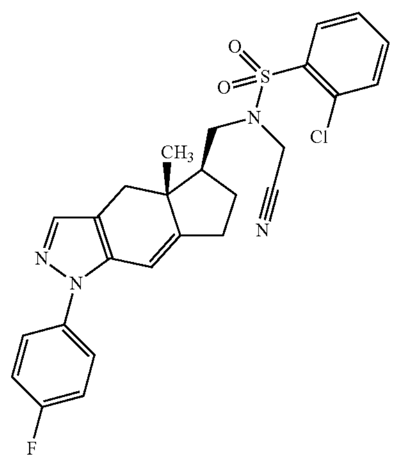 | 2-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide | 511.1332 |
| 51 | 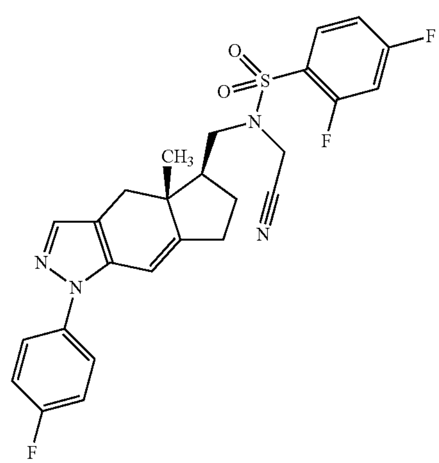 | N-(cyanomethyl)-2,4-difluoro-N-{[(4αR,5S)-1-(4-fluorophenyl)-4α-methyl-1,4,4α,5,6,7-hexahydrocyclopenta[f]indazol-5-yl]methyl}benzenesulfonamide | 513.1533 |

| Ex. | STRUCTURE | NAME | M + 1 |
|---|---|---|---|
| 52 | 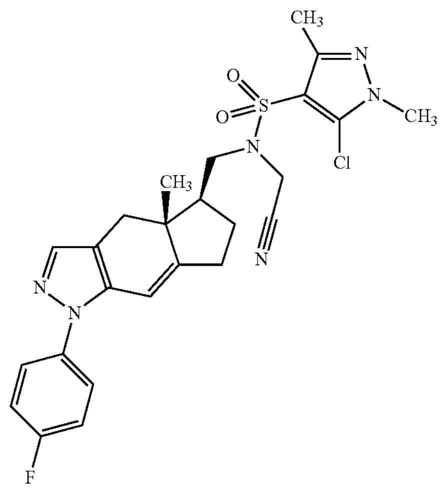 | 5-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}-1,3-dimethyl-1H-pyrazole-4-sulfonamide | 529.1551 |
| 53 | 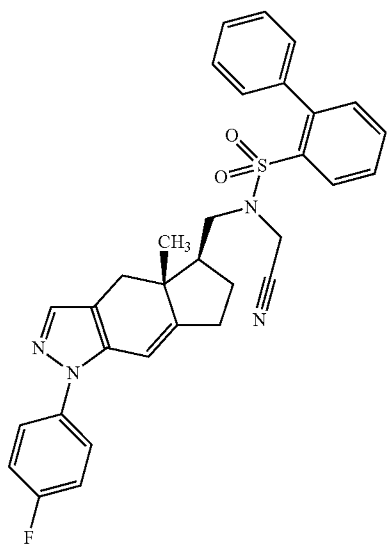 | N-(cyanomethyl)-N-{[(4αR,5S)-1-(4-fluorophenyl)-4α-methyl-1,4,4α,5,6,7-hexahydrocyclopenta[f]indazol-5-yl]methyl}biphenyl-2-sulfonamide | 553.2022 |
| 54 | 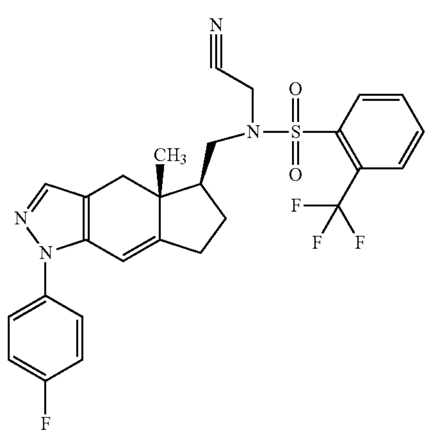 | N-(cyanomethyl)-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide | 545.1587 |

| Ex. | STRUCTURE | NAME | M + 1 |
|---|---|---|---|
| 55 | 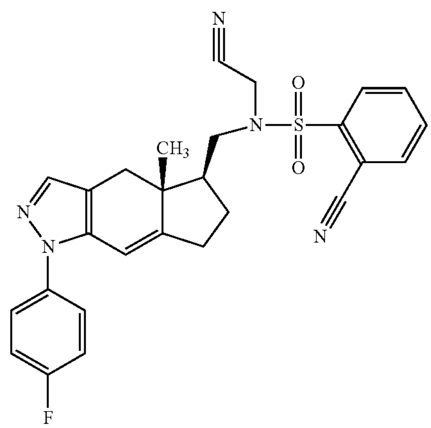 | 2-cyano-N-(cyanomethyl)-N-{[4αR,5S)-1-(4-fluorophenyl)-4α-methyl-1,4,4α,5,6,7-hexahydrocyclopenta[f]indazol-5-yl]methyl}benzenesulfonamide | 502.1672 |
| 56 | 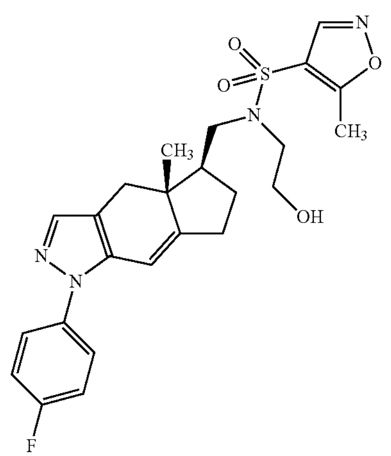 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-methylisoxazole-4-sulfonamide | 487.1798 |
| 57 | 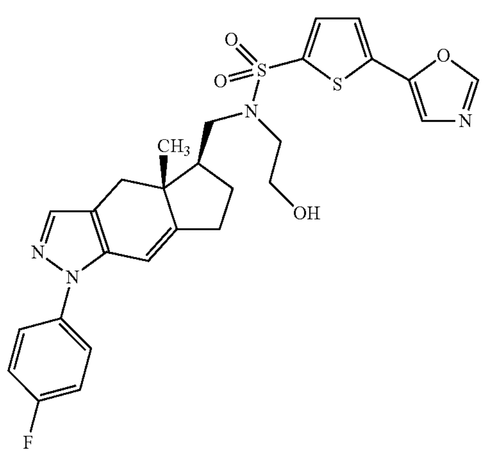 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-(1,3-oxazol-5-yl)thiophene-2-sulfonamide | 555.1515 |

| Ex. | STRUCTURE | NAME | M + 1 |
|---|---|---|---|
| 58 | 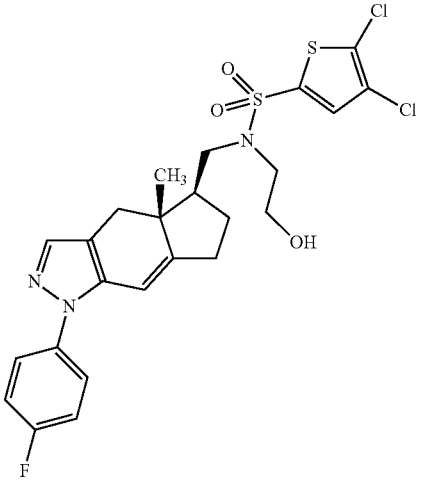 | 4,5-dichloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)thiophene-2-sulfonamide | 556.0681 |
| 59 | 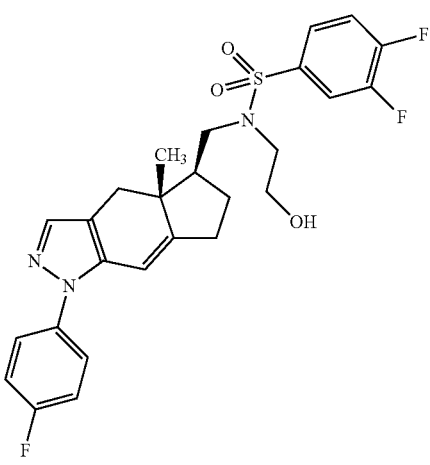 | 3,4-dichloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 518.1709 |
| 60 | 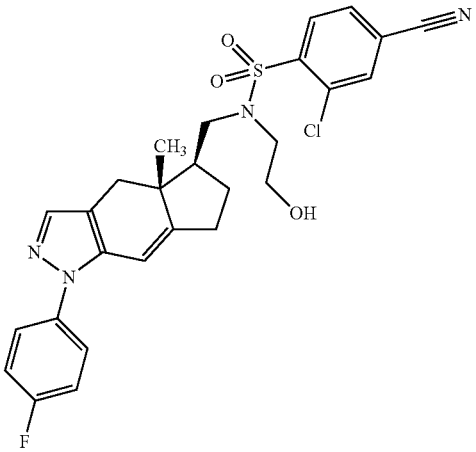 | 2-chloro-4-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 541.1457 |

-continued

| Ex. | STRUCTURE | NAME | M + 1 |
|---|---|---|---|
| 61 | 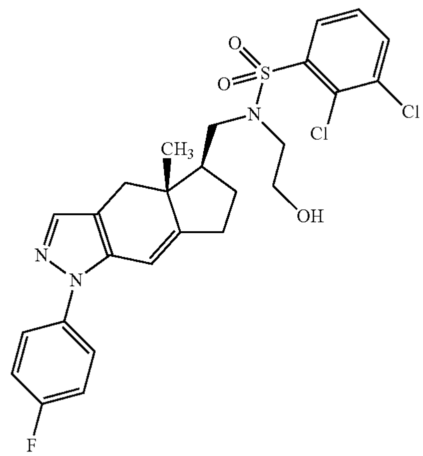 | 2,3-dichloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 550.1123 |
| 62 | 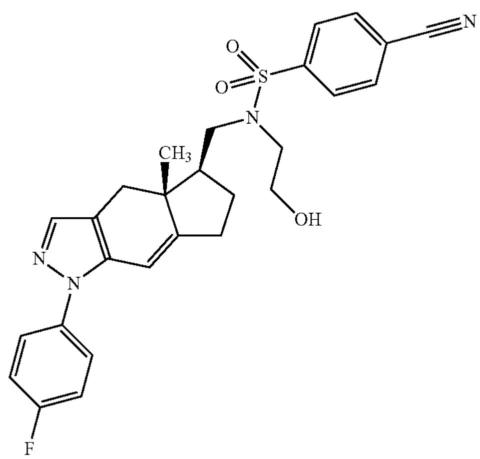 | 4-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 507.1839 |
| 63 | 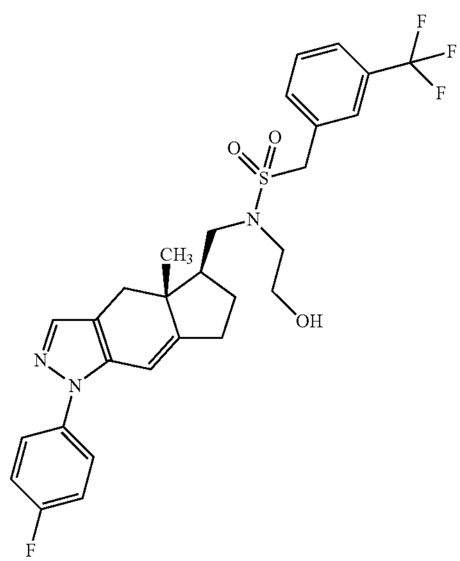 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-[3-(trifluoromethyl)phenyl]methanesulfonamide | 564.1907 |

-continued

| Ex. | STRUCTURE | NAME | M + 1 |
|---|---|---|---|
| 64 | 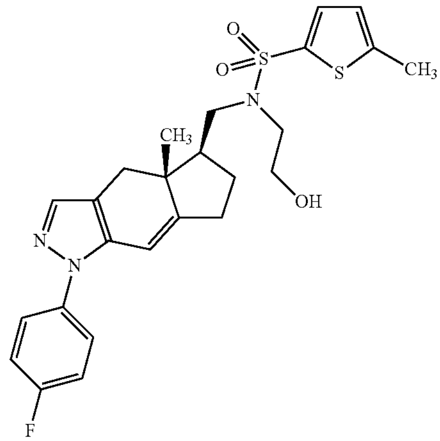 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-methylthiophene-2-sulfonamide | 502.1621 |
| 65 | 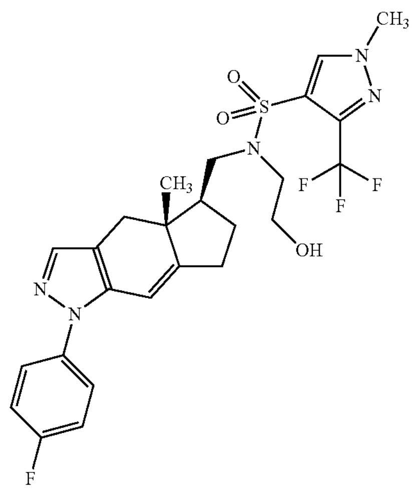 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-methyl-3-(trifluoromethyl)-1H-pyrazole-4-sulfonamide | 554.1837 |
| 66 | 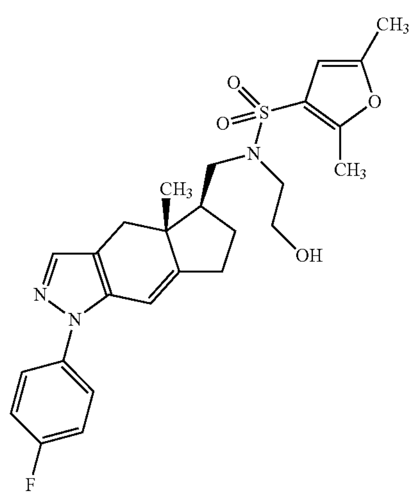 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-2,5-dimethylfuran-3-sulfonamide | 500.2027 |

| Ex. | STRUCTURE | NAME | M + 1 |
|---|---|---|---|
| 67 | 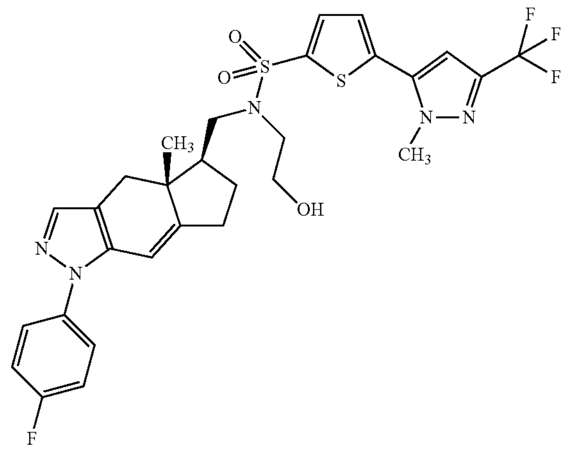 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-[1-methyl-3-(trifluoromethyl)-1H-pyrazole-5-yl]thiophene-2-sulfonamide | 636.1738 |
| 68 | 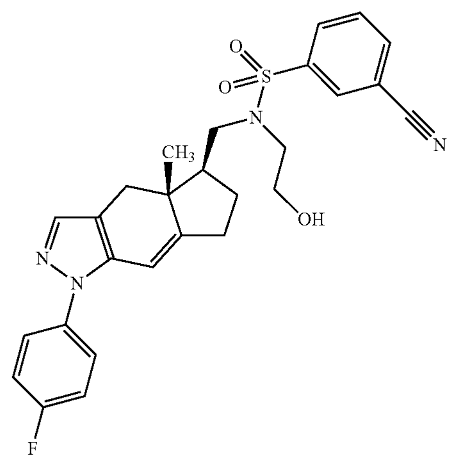 | 3-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 507.1851 |
| 69 | 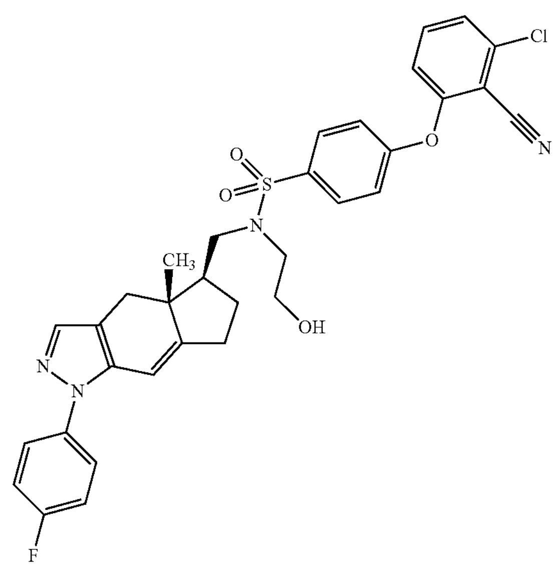 | 4-(3-chloro-2-cyanophenoxy)-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 633.173 |

| Ex. | STRUCTURE | NAME | M + 1 |
|---|---|---|---|
| 70 | 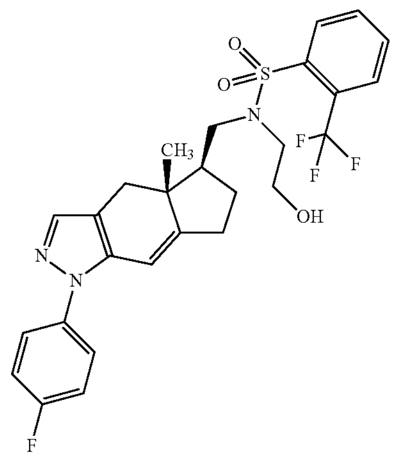 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-2-(trifluoromethyl)benzenesulfonamide | 550.1763 |
| 71 | 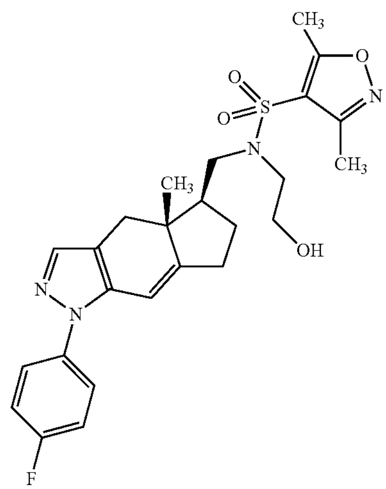 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-3,5-dimethylisoxazole-4-sulfonamide | 501.1948 |
| 72 | 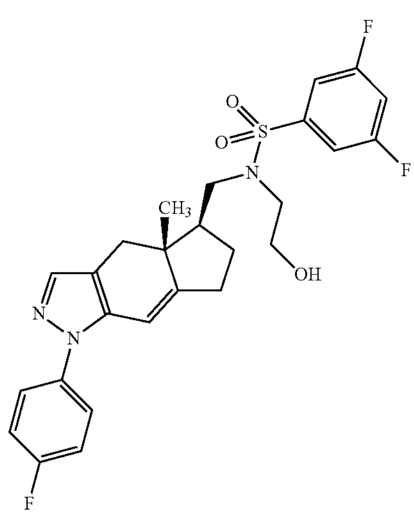 | 3,5-dichloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benezenesulfonamide | 518.1747 |

| Ex. | STRUCTURE | NAME | M + 1 |
|---|---|---|---|
| 73 | 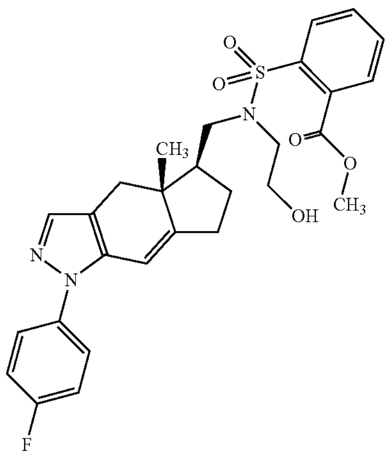 | methyl 2-{[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}benzoate | 540.1952 |
| 74 | 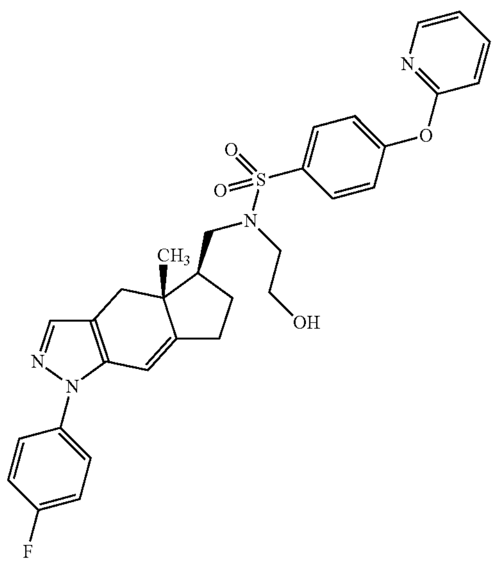 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-4-(pyridin-2-yloxy)benzenesulfonamide | 575.2119 |
| 75 | 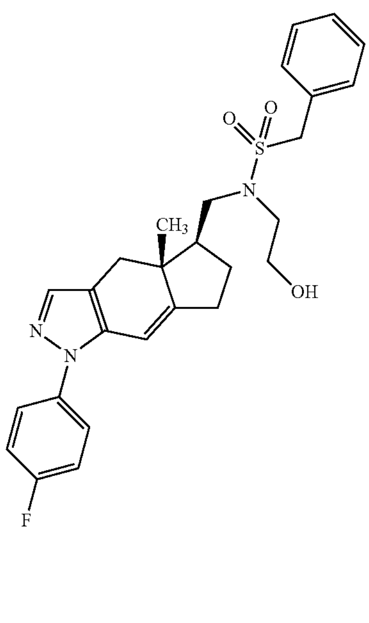 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-phenylmethanesulfonamide | 496.2065 |

| Ex. | STRUCTURE | NAME | M + 1 |
|---|---|---|---|
| 76 | 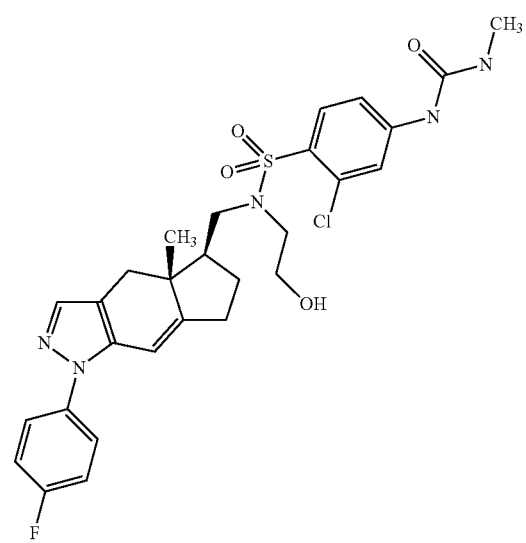 | 2-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-4-{[(methylamino)carbonyl]amino}-benzenesulfonamide | 588.1819 |
| 77 | 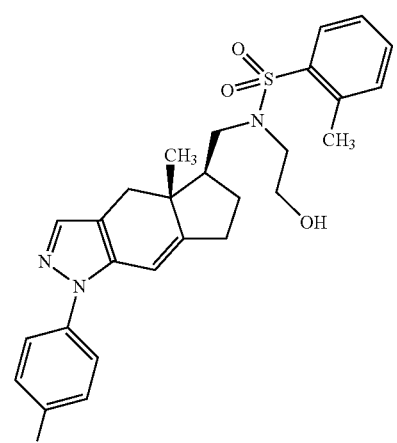 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-2-methylbenzenesulfonamide | 496.2049 |
| 78 | 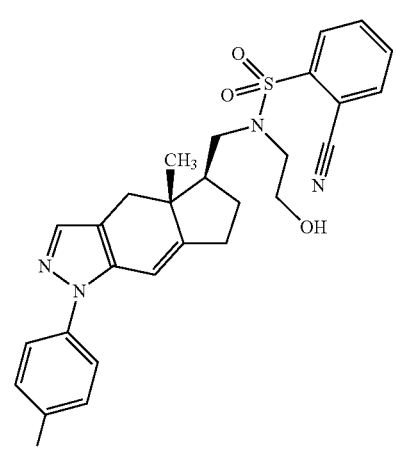 | 2-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 507.1856 |

-continued

| Ex. | STRUCTURE | NAME | M + 1 |
| --- | --- | --- | --- |
| 79 | 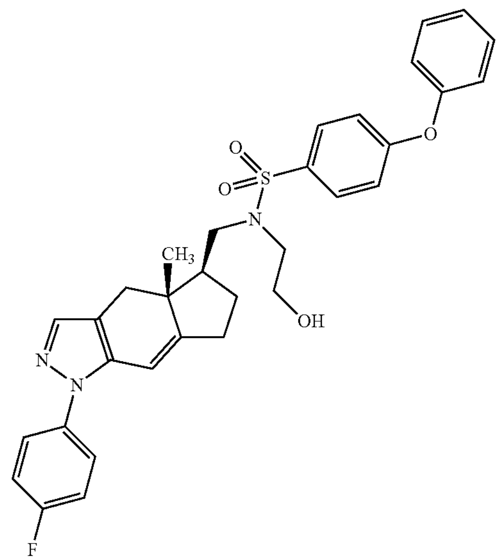 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-4-phenoxybenzenesulfonamide | 574.2178 |
| 80 | 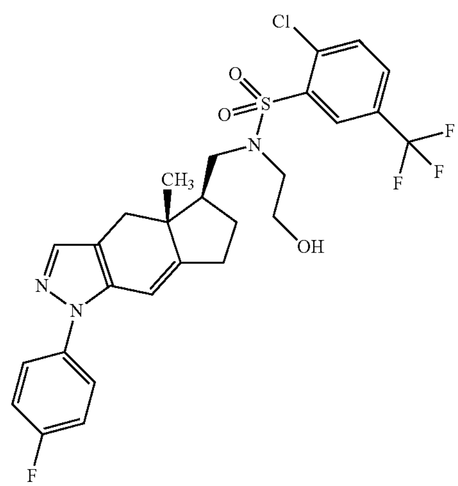 | 2-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-(trifluoromethyl)benzenesulfonamide | 584.1395 |
| 81 | 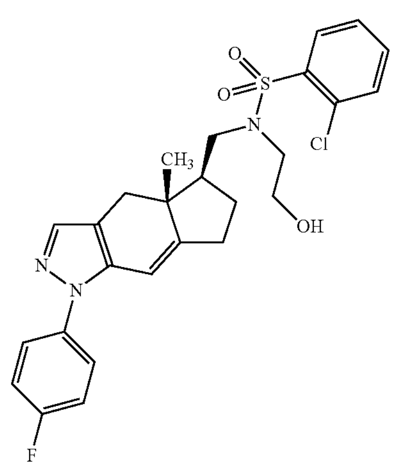 | 2-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 516.1502 |

| Ex. | STRUCTURE | NAME | M + 1 |
|---|---|---|---|
| 82 | 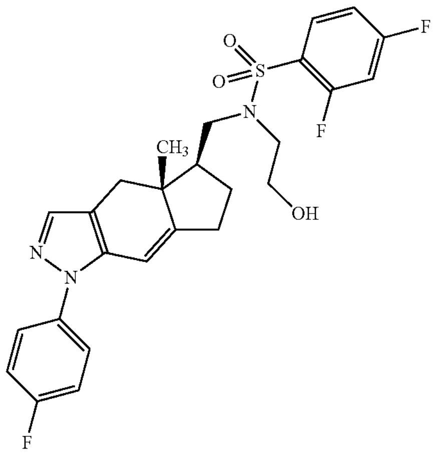 | 2,4-difluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide | 518.1703 |
| 83 | 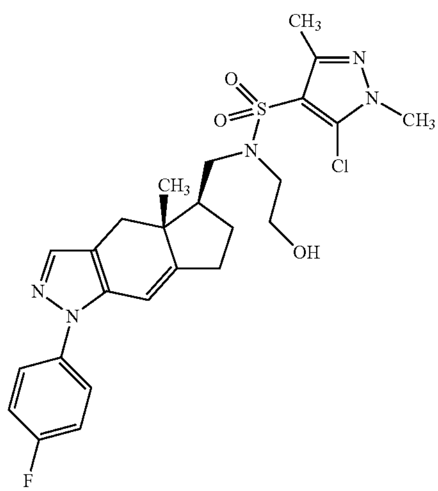 | 5-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1,3-dimethyl-1H-pyrazole-4-sulfonamide | 534.1721 |
| 84 | 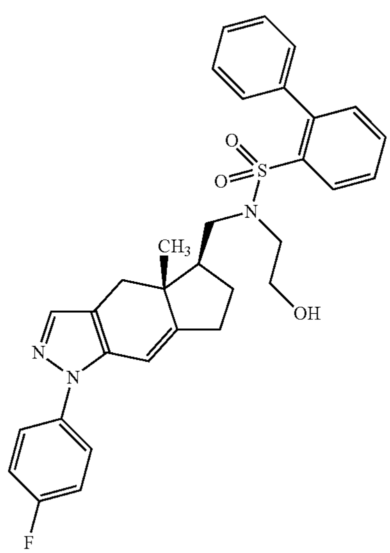 | N-{[(4αR,5S)-1-(4-fluorophenyl)-4α-methyl-1,4,4α,5,6,7-hexahydrocyclopenta[f]indazol-5-yl]methyl}-N-(2-hydroxyethyl)biphenyl-2-sulfonamide | 558.2223 |

-continued

| Ex. | STRUCTURE | NAME | M + 1 |
|---|---|---|---|
| 85 | 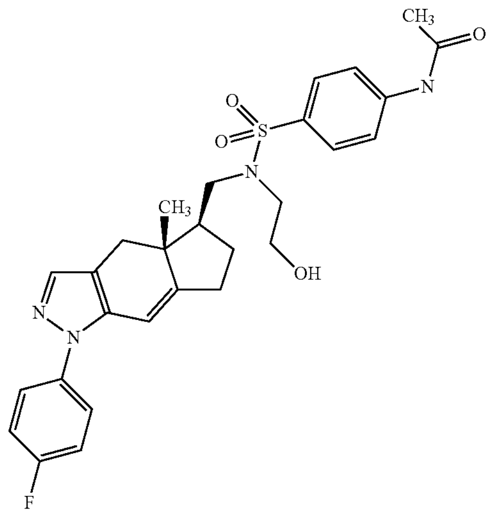 | N-(4-{[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}phenyl)acetamide | 539.2108 |
| 86 | 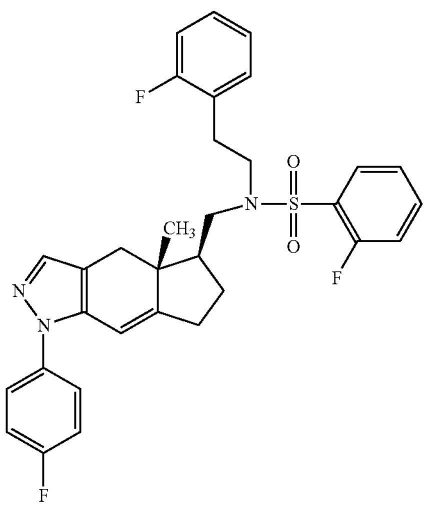 | 2-fluoro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}benzenesulfonamide | 578.2068 |
| 87 | 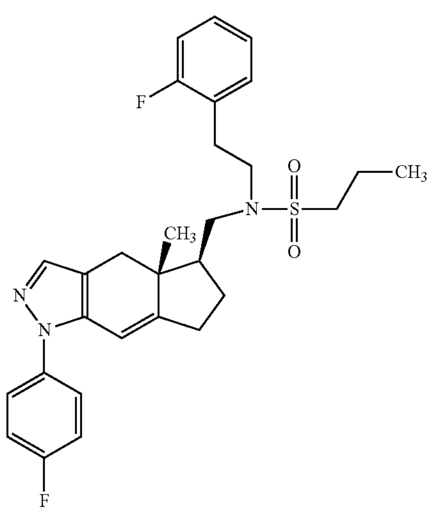 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}propane-1-sulfonamide | 526.2322 |

| Ex. | STRUCTURE | NAME | M + 1 |
|---|---|---|---|
| 88 | 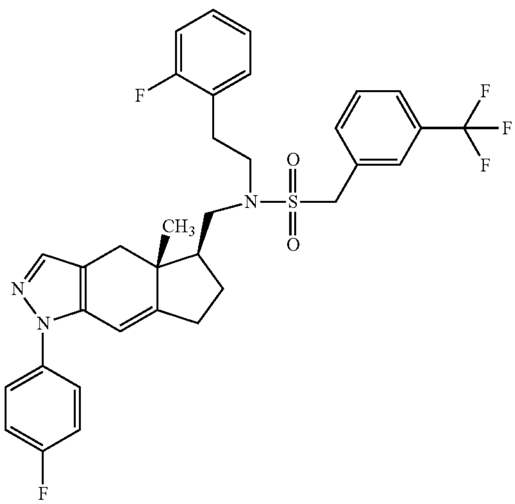 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-[3-(trifluoromethyl)phenyl]methanesulfonamide | 642.2192 |
| 89 | 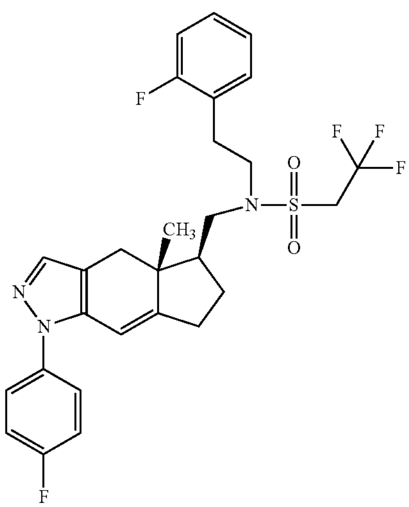 | 2,2,2-trifluoro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}ethanesulfonamide | 566.1881 |
| 90 | 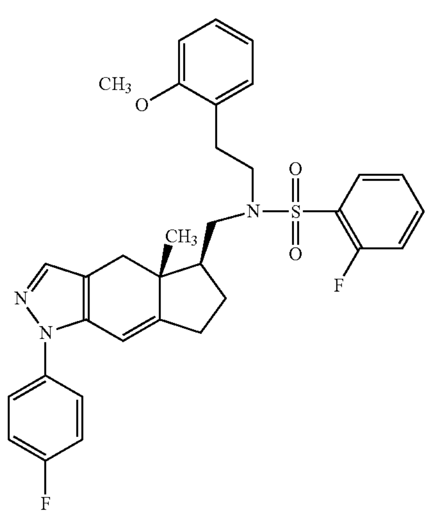 | 2-fluoro-N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]benzenesulfonamide | 590.2265 |

| Ex. | STRUCTURE | NAME | M + 1 |
|---|---|---|---|
| 91 | 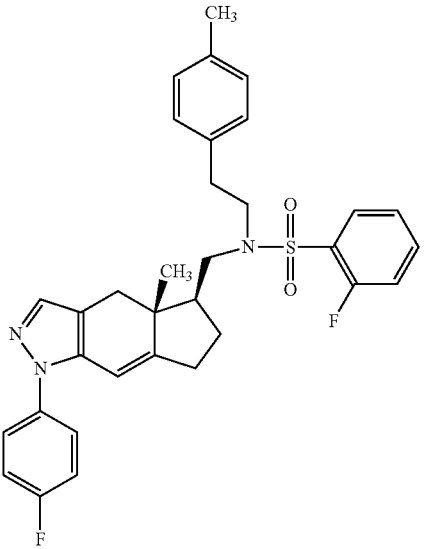 | 2-fluoro-N-{[(4αR,5S)-1-(4-fluorophenyl)-4α-methyl-1,4,4α,5,6,7-hexahydrocyclopenta[f]indazol-5-yl]methyl}-N-[2-(4-methylphenyl)ethyl]benzenesulfonamide | 574.2318 |
| 92 | 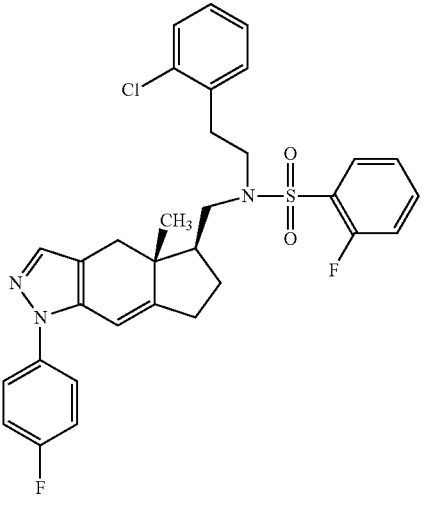 | N-[2-(2-chlorophenyl)ethyl]-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide | 594.1773 |
| 93 | 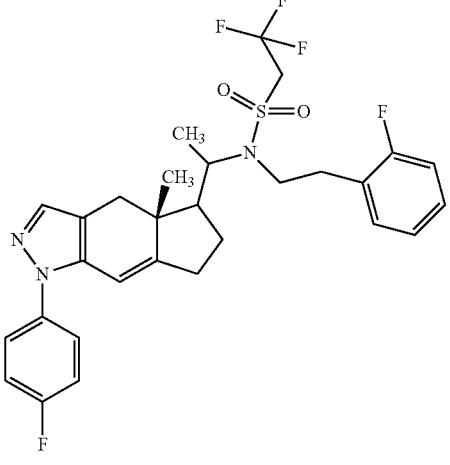 | 2,2,2-trifluoro-N-[2-(2-fluorophenyl)ethyl]-N-{1-[(4αR)-1-(4-fluorophenyl)-4α-methyl-1,4,4α,5,6,7-hexahydrocyclopenta[f]indazol-5-yl]ethyl}ethanesulfonamide | 580.2 |

-continued

| Ex. | STRUCTURE | NAME | M + 1 |
|---|---|---|---|
| 94 | 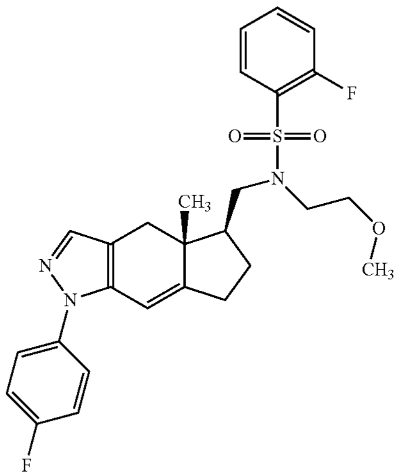 | 2-fluoro-N-{[(4αR,5S)-1-(4-fluorophenyl)-4α-methyl-1,4,4α,5,6,7-hexahydrocyclopenta[f]indazol-5-yl]methyl}-N-(2-methoxyethyl)benzenesulfonamide | 514.1972 |
| 95 | 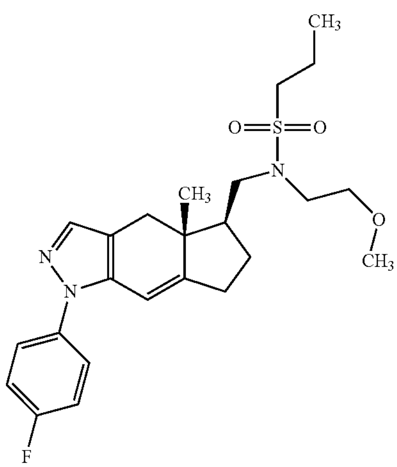 | N-{[(4αR,5S)-1-(4-fluorophenyl)-4α-methyl-1,4,4α,5,6,7-hexahydrocyclopenta[f]indazol-5-yl]methyl}-N-(2-methoxyethyl)propane-1-sulfonamide | 462.2221 |
| 96 | 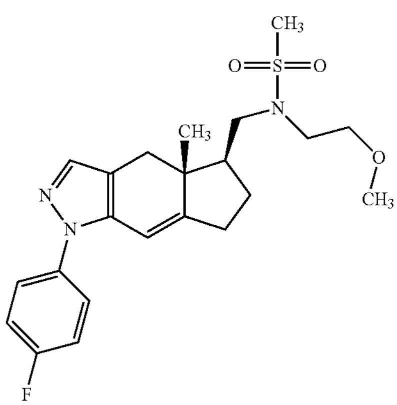 | N-{[(4αR,5S)-1-(4-fluorophenyl)-4α-methyl-1,4,4α,5,6,7-hexahydrocyclopenta[f]indazol-5-yl]methyl}-N-(2-methoxyethyl)methanesulfonamide | 434.1908 |

| Ex. | STRUCTURE | NAME | M + 1 |
|---|---|---|---|
| 97 | 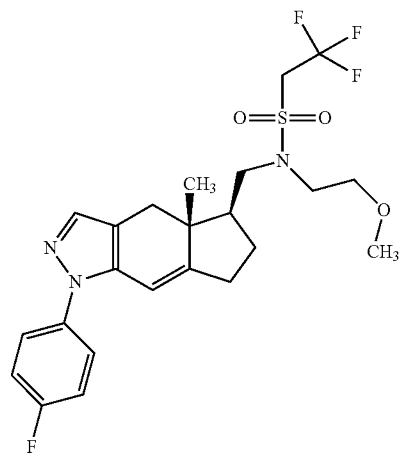 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide | 502.1782 |
| 98 | 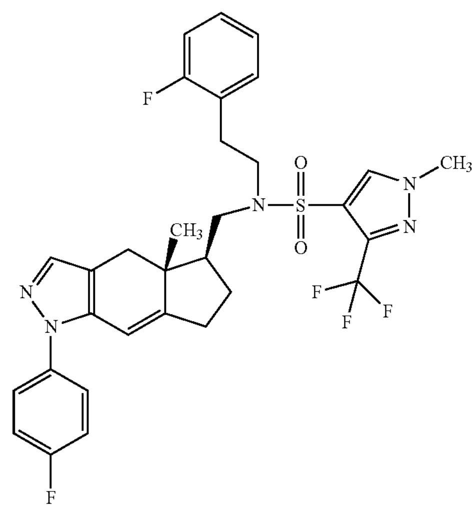 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonamide | 632.2077 |
| 99 | 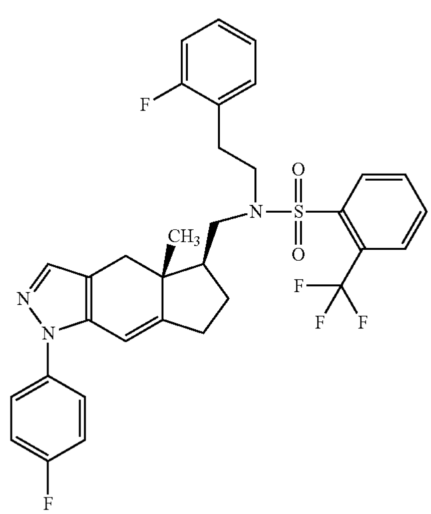 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide | 628.2016 |

| Ex. | STRUCTURE | NAME | M + 1 |
|---|---|---|---|
| 100 | 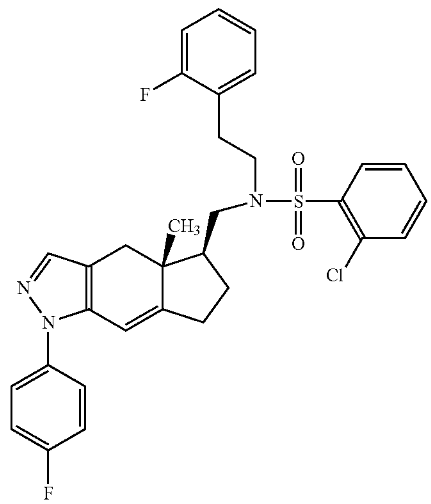 | 2-chloro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}benzenesulfonamide | 594.1754 |
| 101 | 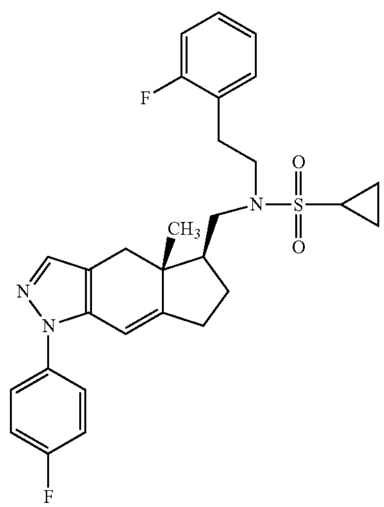 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}cyclopropanesulfonamide | 524.2152 |
| 102 | 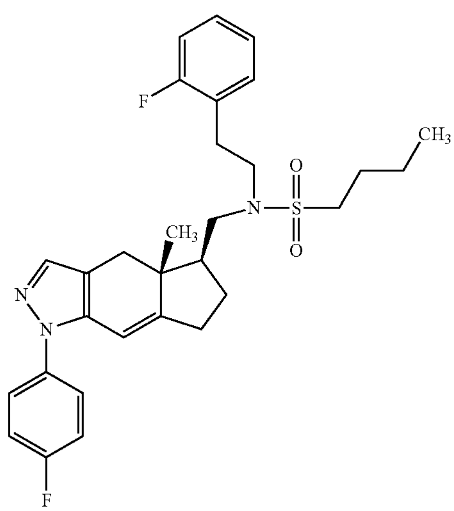 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}butane-1-sulfonamide | 540.2466 |

-continued

| Ex. | STRUCTURE | NAME | M + 1 |
|---|---|---|---|
| 103 | 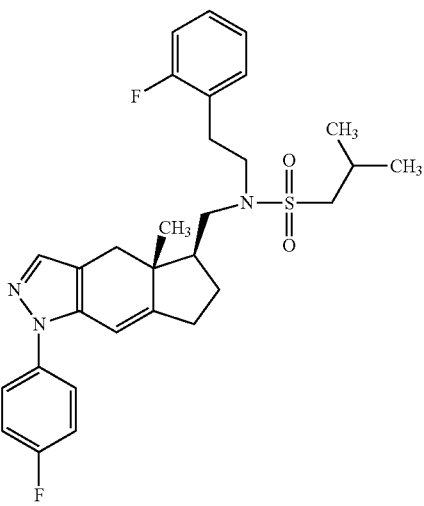 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-2-methylpropane-1-sulfonamide | 540.2468 |
| 104 | 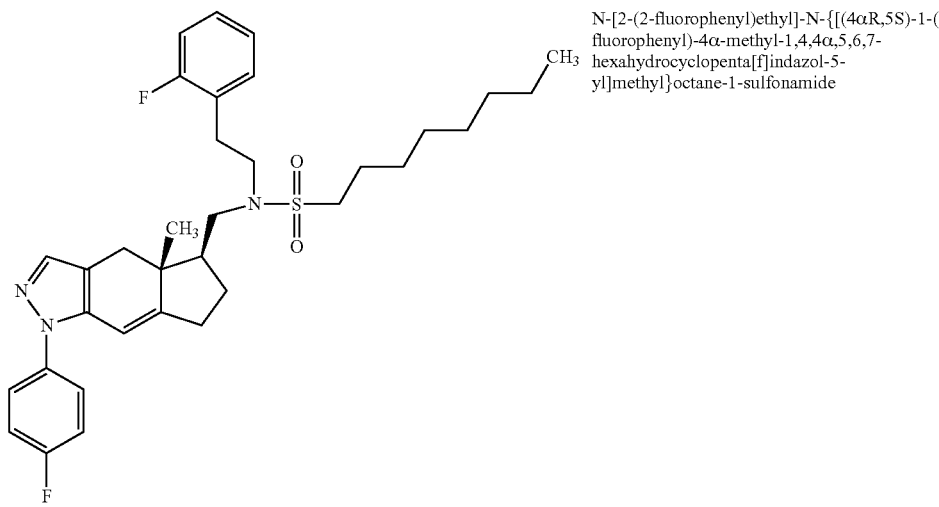 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}octane-1-sulfonamide | 596.3093 |
| 105 | 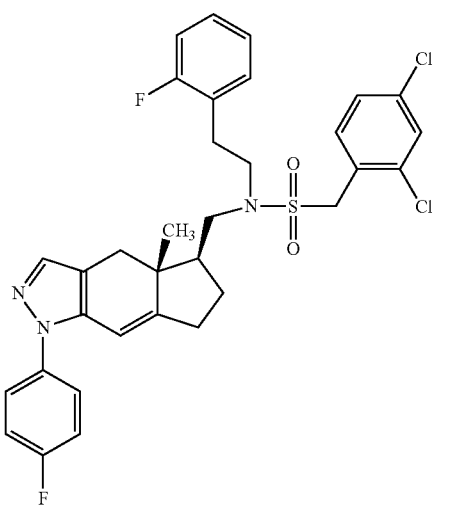 | 1-(2,4-dichlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide | 642.1514 |

-continued

| Ex. | STRUCTURE | NAME | M + 1 |
|---|---|---|---|
| 106 | 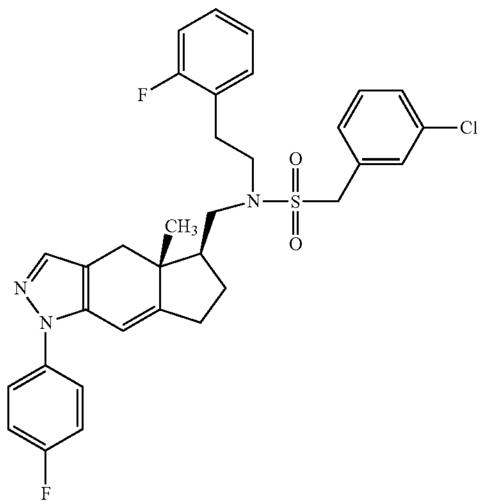 | 1-(3-chlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide | 608.1905 |
| 107 | 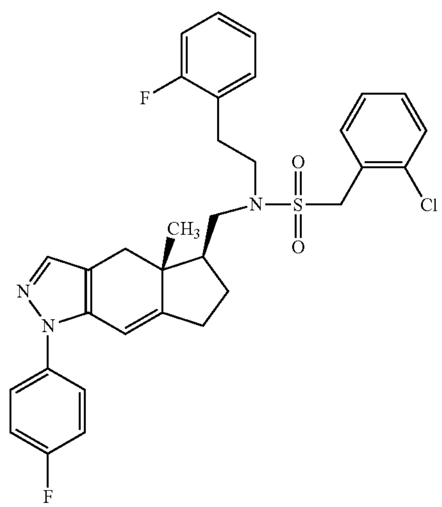 | 1-(2-chlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide | 608.1908 |
| 108 | 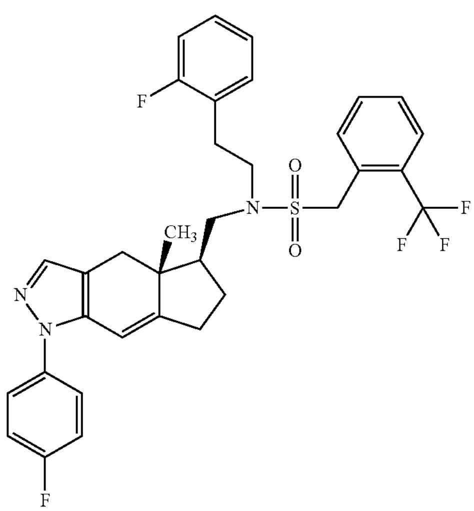 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-[2-(trifluoromethyl)phenyl]methanesulfonamide | 642.2171 |

| Ex. | STRUCTURE | NAME | M + 1 |
|---|---|---|---|
| 109 | 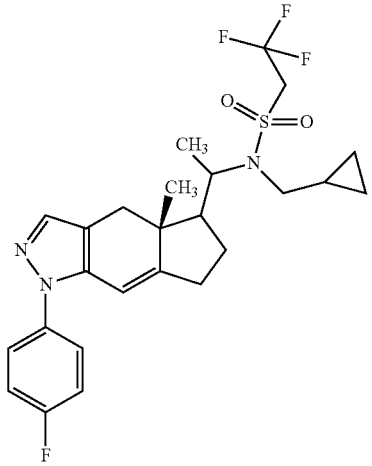 | N-(cyclopropylmethyl)-2,2,2-trifluoro-N-{1-[(4αR)-1-(4-fluorophenyl)-4α-methyl-1,4,4α,5,6,7-hexahydrocyclopenta[f]indazol-5-yl]ethyl}ethanesulfonamide | 512.6 |
| 110 | 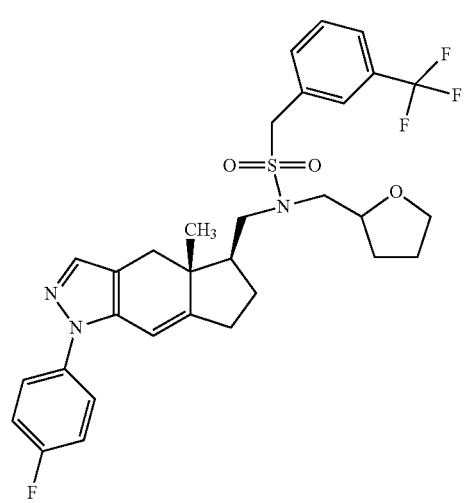 | N-{[(4αR,5S)-1-(4-fluorophenyl)-4α-methyl-1,4,4α,5,6,7-hexahydrocyclopenta[f]indazol-5-yl]methyl}-N-(tetrahydrofuran-2-ylmethyl)-1-[3-(trifluoromethyl)phenyl]methanesulfonamide | 604.7 |
| 111 | 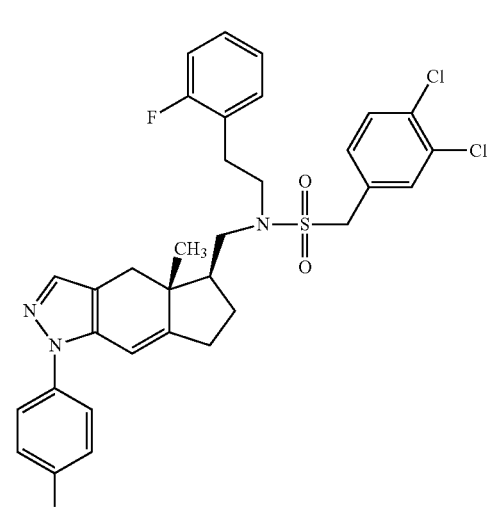 | 1-(3,4-dichlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide | 642.1581 |

| Ex. | STRUCTURE | NAME | M + 1 |
|---|---|---|---|
| 112 | 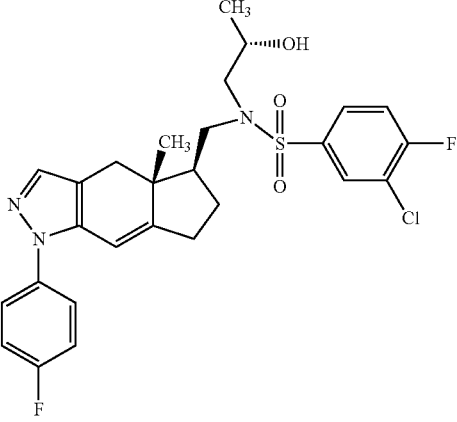 | 3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-[(2S)-2-hydroxypropyl]benzenesulfonamide | 548.1557 |
| 113 | 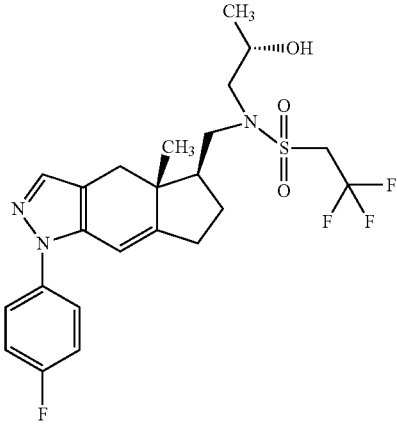 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[(2S)-2-hydroxypropyl]benzenesulfonamide | 502.1763 |
| 114 | 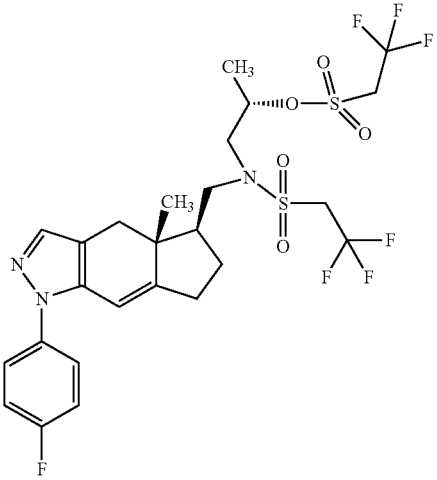 | (1S)-2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}-1-methylethyl 2,2,2-trifluoroethanesulfonate | 648.1412 |

| Ex. | STRUCTURE | NAME | M + 1 |
|---|---|---|---|
| 115 | 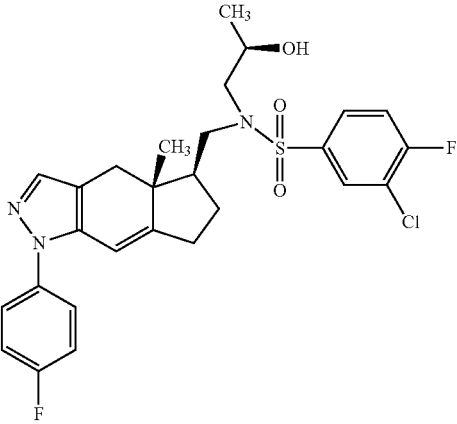 | 3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-[(2R)-2-hydroxypropyl]benzenesulfonamide | 548.1581 |
| 116 | 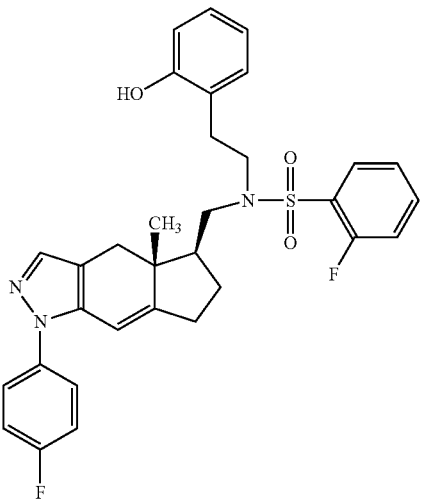 | 2-fluoro-N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]benzenesulfonamide | 576.2094 |
| 117 | 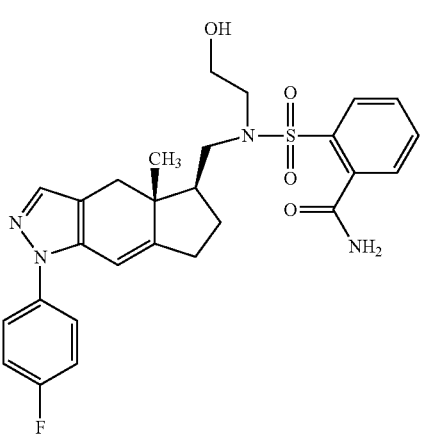 | 2-{[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}benzamide | 525.1951 |

-continued

| Ex. | STRUCTURE | NAME | M + 1 |
|---|---|---|---|
| 118 | 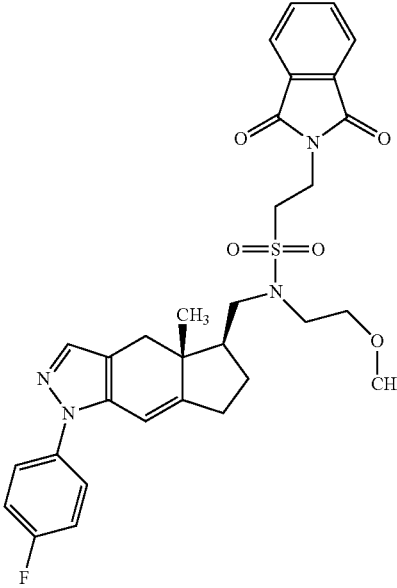 | 2-(1,3-dioxo-1,3-dihydro-2H-isoindol-2-yl)-N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide | 593 |
| 119 | 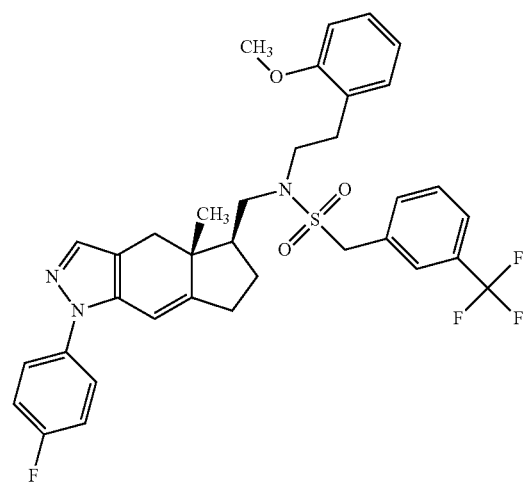 | N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]-1-[3-(trifluoromethyl)phenyl]methanesulfonamide | 654.2390 |
| 120 | 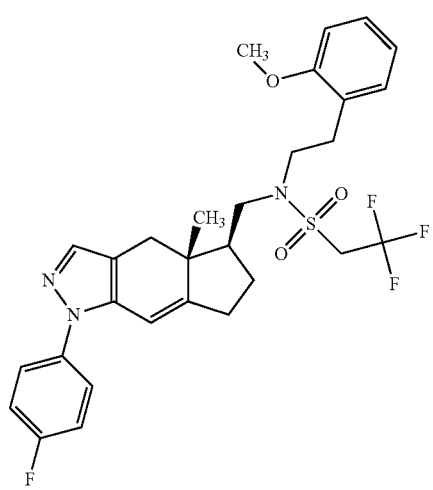 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]ethanesulfonamide | 578.2097 |

| Ex. | STRUCTURE | NAME | M + 1 |
|---|---|---|---|
| 121 | 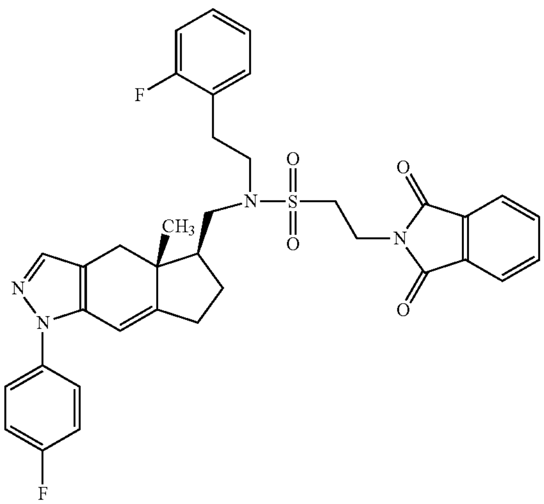 | 2-(1,3-dioxo-1,3-dihydro-2H-isoindol-2-yl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}ethanesulfonamide | 657.2340 |
| 122 | 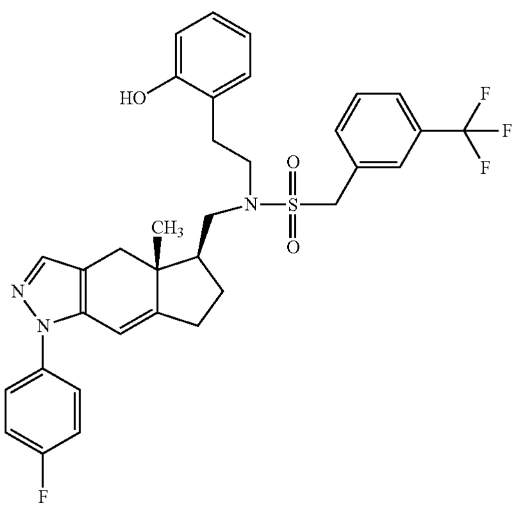 | N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-1-[3-(trifluoromethyl)phenyl]methanesulfonamide | 640.2240 |
| 123 | 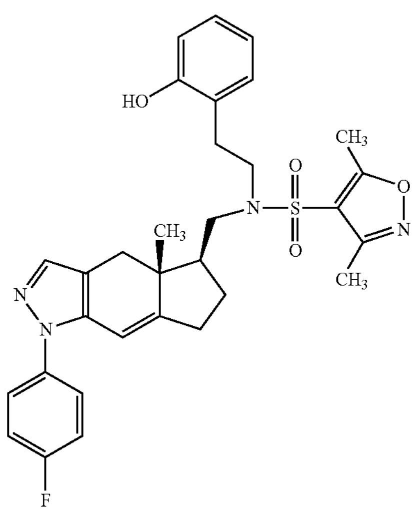 | N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-3,5-dimethylisoxazole-4-sulfonamide | 577.2259 |

| Ex. | STRUCTURE | NAME | M + 1 |
|---|---|---|---|
| 124 | 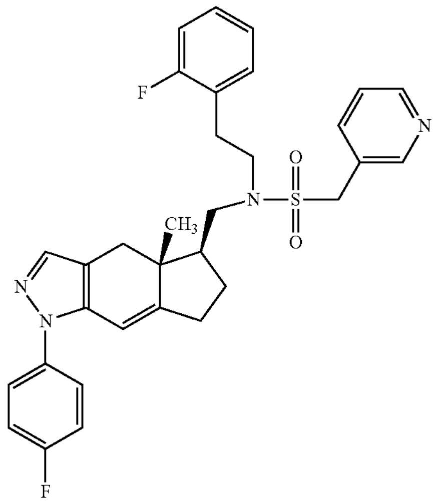 | N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide | 575.2262 |
| 125 | 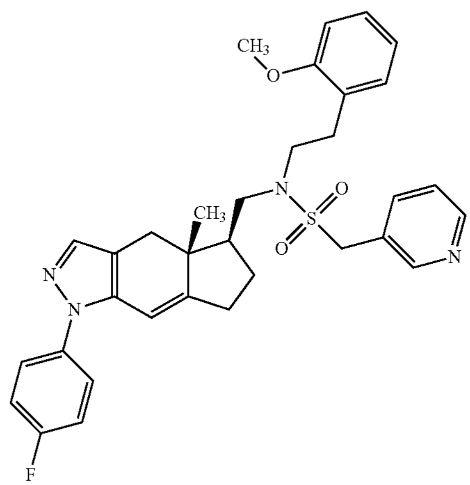 | N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]-1-pyridin-3-ylmethanesulfonamide | 587.2464 |
| 126 | 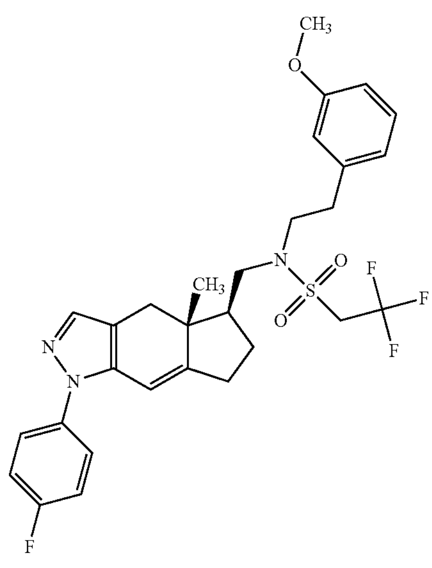 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(3-methoxyphenyl)ethyl]ethanesulfonamide | 578.2070 |

| Ex. | STRUCTURE | NAME | M + 1 |
|---|---|---|---|
| 127 | 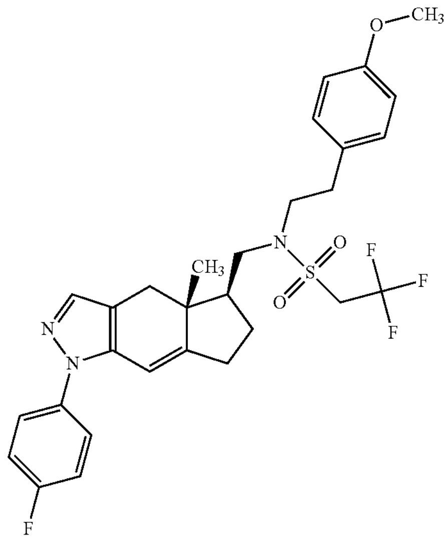 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(4-methoxyphenyl)ethyl]ethanesulfonamide | 578.2079 |
| 128 | 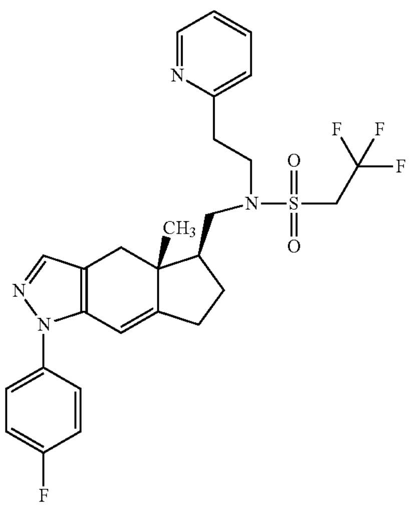 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)ethanesulfonamide | 549.1918 |
| 129 | 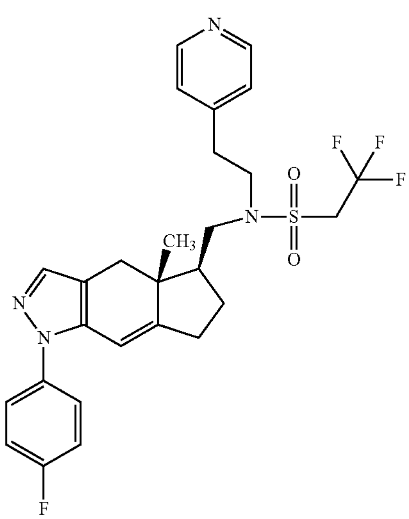 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-4-ylethyl)ethanesulfonamide | 549.1914 |

-continued

| Ex. | STRUCTURE | NAME | M + 1 |
|---|---|---|---|
| 130 | 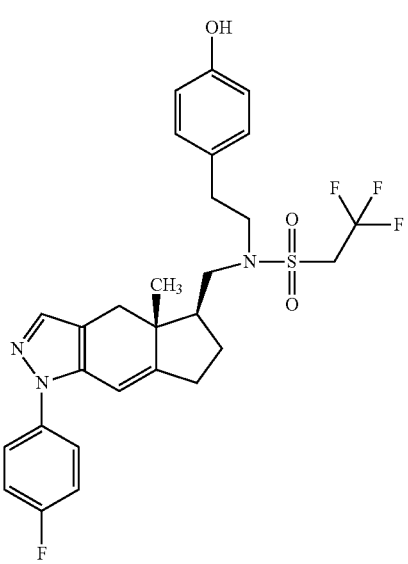 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(4-hydroxyphenyl)ethyl]ethanesulfonamide | 564.1927 |
| 131 | 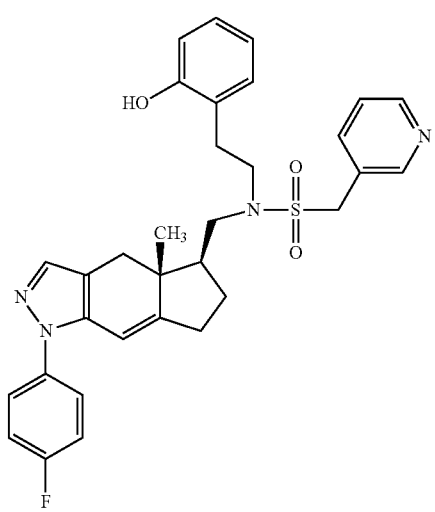 | N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-1-pyridin-3-ylmethanesulfonamide | 573.2316 |
| 132 | 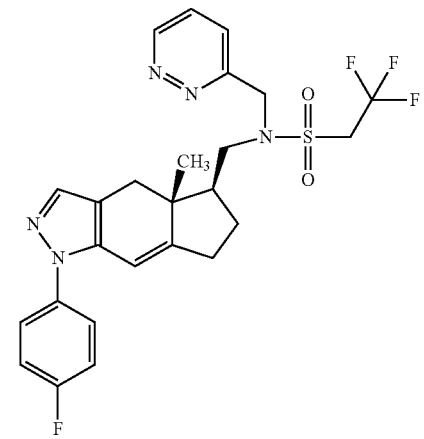 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(pyridazin-3-ylmethyl)ethanesulfonamide | 536.1744 |

| Ex. | STRUCTURE | NAME | M + 1 |
|---|---|---|---|
| 133 | 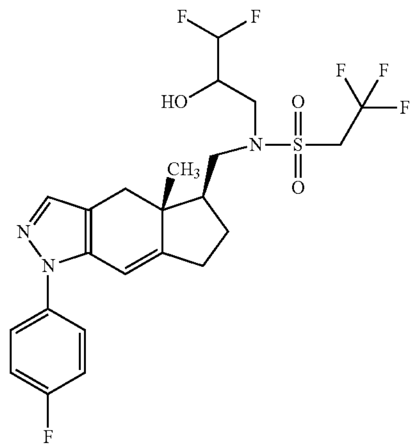 | N-(3,3-difluoro-2-hydroxypropyl)-2,2,2-trifluoro-N-{[(4αR,5S)-1-(4-fluorophenyl)-4α-methyl-1,4,4α,5,6,7-hexahydrocyclopenta[f]indazol-5-yl]methyl}ethanesulfonamide | 538.1585 |
| 134 | 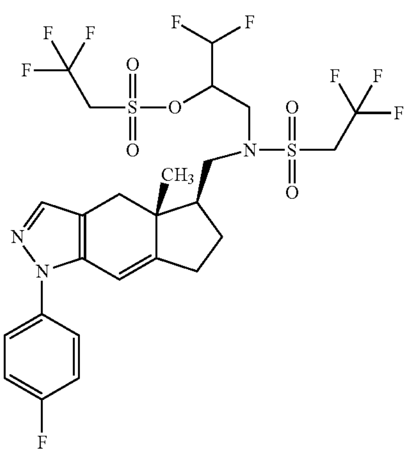 | 2,2-difluoro-1-({{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}methyl)ethyl 2,2,2-trifluoroethanesulfonate | 684.1219 |
| 135 | 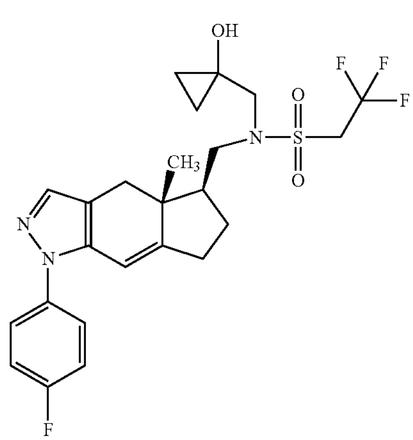 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[(1-hydroxycyclopropyl)methyl]ethanesulfonamide | 514.1782 |

-continued

| Ex. | STRUCTURE | NAME | M + 1 |
|---|---|---|---|
| 136 | 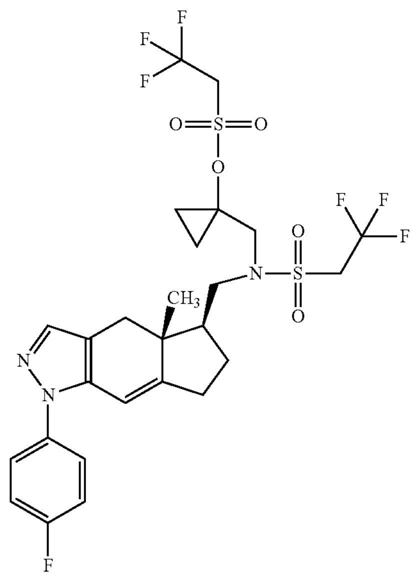 | 1-({{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}methyl)cyclopropyl 2,2,2-trifluoroethanesulfonate | 660.1408 |
| 137 | 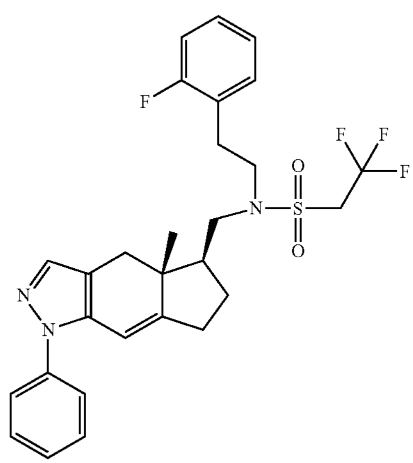 | 2,2,2-trifluoro-N-[2-(2-fluorophenyl)ethyl]-N-{[(4αR,5S)-4α-methyl-1-phenyl-1,4,4α,5,6,7-hexahydrocyclopenta[f]indazol-5-yl]methyl}ethanesulfonamide | 548.5 |
| 138 | 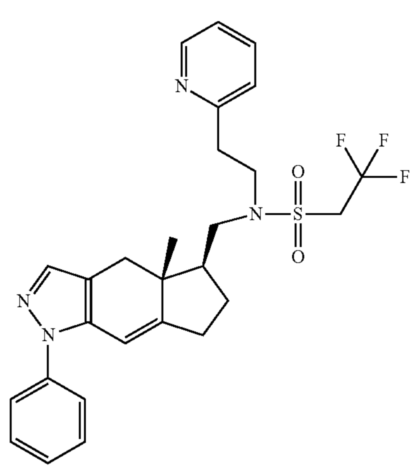 | 2,2,2-trifluoro-N-{[(4αR,5S)-4α-methyl-1-phenyl-1,4,4α,5,6,7-hexahydrocyclopenta[f]indazol-5-yl]methyl}-N-(2-pyridin-2-ylethyl)ethanesulfonamide | 531.6 |

-continued

| Ex. | STRUCTURE | NAME | M + 1 |
|---|---|---|---|
| 139 | 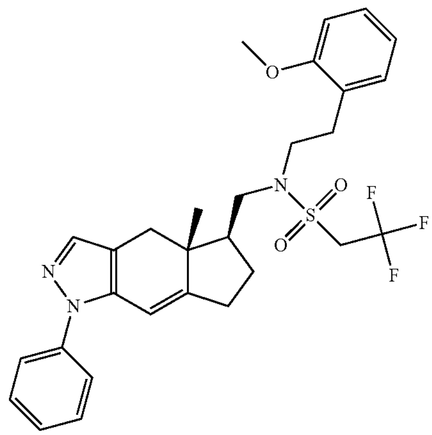 | 2,2,2-trifluoro-N-[2-(2-methoxyphenyl)ethyl]-N-{[(4αR,5S)-4α-methyl-1-phenyl-1,4,4α,5,6,7-hexahydrocyclopenta[f]indazol-5-yl]methyl}ethanesulfonamide | 560.6 |
| 140 | 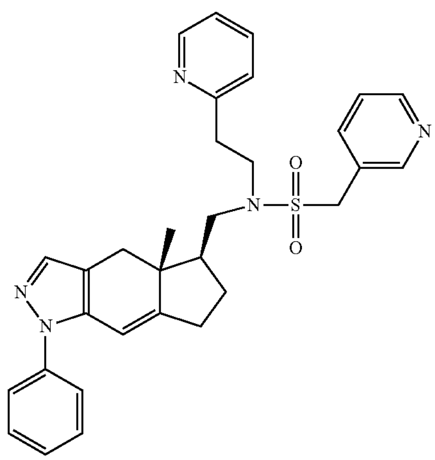 | N-{[(4αR,5S)-4α-methyl-1-phenyl-1,4,4α,5,6,7-hexahydrocyclopenta[f]indazol-5-yl]methyl}-1-pyridin-3-yl-N-(2-pyridin-2-ylethyl)methanesulfonamide | 539.6 |
| 141 | 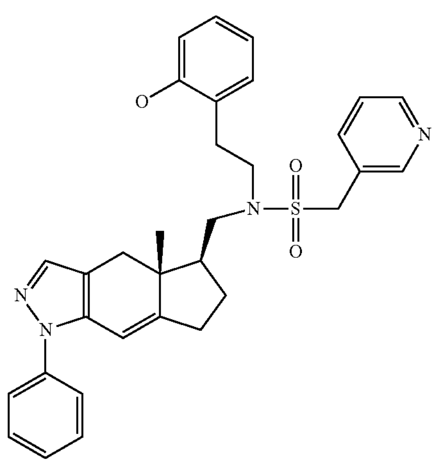 | N-[2-(2-hydroxyphenyl)ethyl]-N-{[(4αR,5S)-4α-methyl-1-phenyl-1,4,4α,5,6,7-hexahydrocyclopenta[f]indazol-5-yl]methyl}-1-pyridin-3-ylmethanesulfonamide | 555.7 |

-continued

| Ex. | STRUCTURE | NAME | M + 1 |
|---|---|---|---|
| 142 | 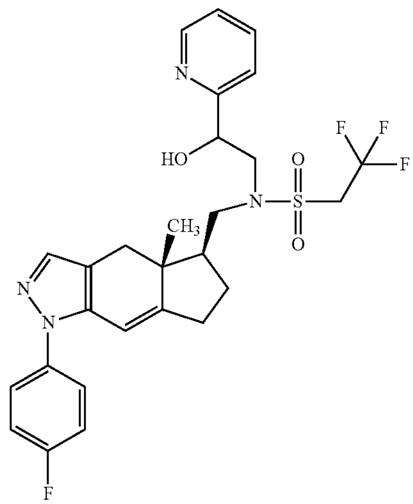 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-2-ylethyl)ethanesulfonamide | 565.1900 |
| 143 | 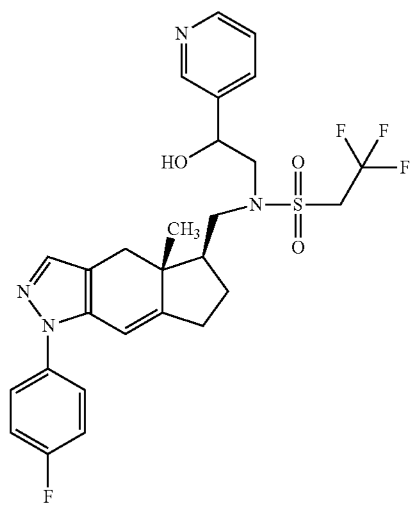 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-3-ylethyl)ethanesulfonamide | 565.1889 |
| 144 | 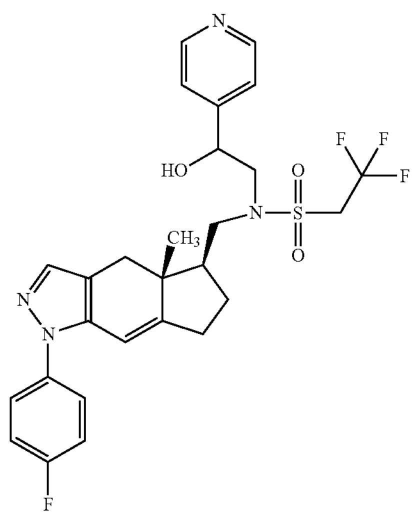 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-4-ylethyl)ethanesulfonamide | 565.1891 |

| Ex. | STRUCTURE | NAME | M + 1 |
|---|---|---|---|
| 145 | 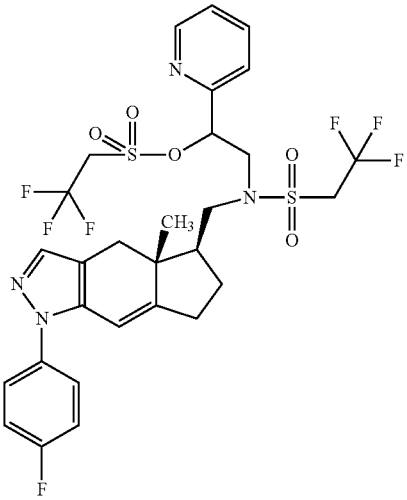 | 2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}-1-pyridin-2-ylethyl 2,2,2-trifluoroethanesulfonate | 711.1517 |
| 146 | 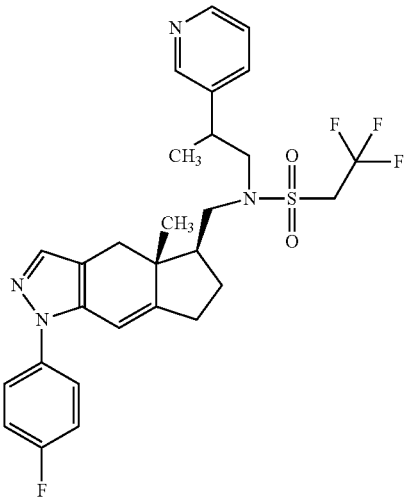 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-3-ylpropyl)ethanesulfonamide | 563.2102 |
| 147 | 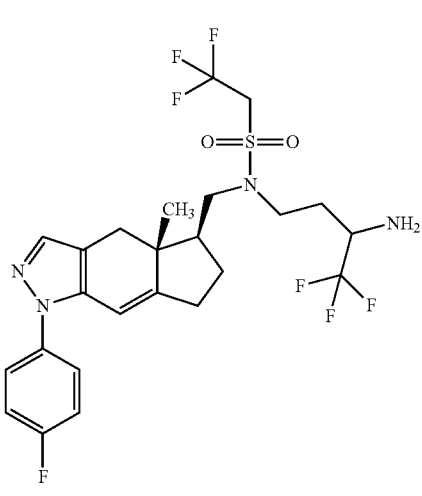 | N-(3-amino-4,4,4-trifluorobutyl)-2,2,2-trifluoro-N-{[(4aR,5S)-1-(4-fluorophenyl)-4α-methyl-1,4,4α,5,6,7-hexahydrocyclopenta[f]indazol-5-yl]methyl}ethanesulfonamide | 569.1797 |

| Ex. | STRUCTURE | NAME | M + 1 |
|---|---|---|---|
| 148 | 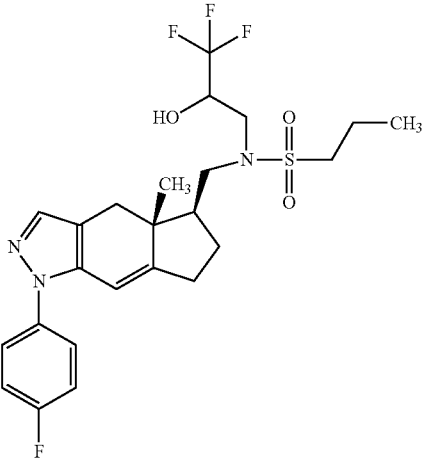 | N-{[(4αR,5S)-1-(4-fluorophenyl)-4α-methyl-1,4,4α,5,6,7-hexahydrocyclopenta[f]indazol-5-yl]methyl}-N-(3,3,3-trifluoro-2-hydroxypropyl)propane-1-sulfonamide | 516.1924 |
| 149 | 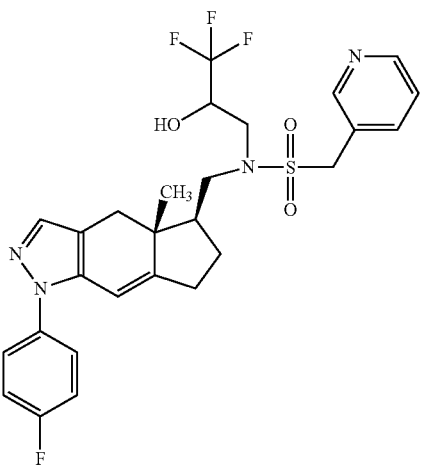 | N-{[(4αR,5S)-1-(4-fluorophenyl)-4α-methyl-1,4,4α,5,6,7-hexahydrocyclopenta[f]indazol-5-yl]methyl}-1-pyridin-3-yl-N-(3,3,3-trifluoro-2-hydroxypropyl)methanesulfonamide | 565.1896 |
| 150 | 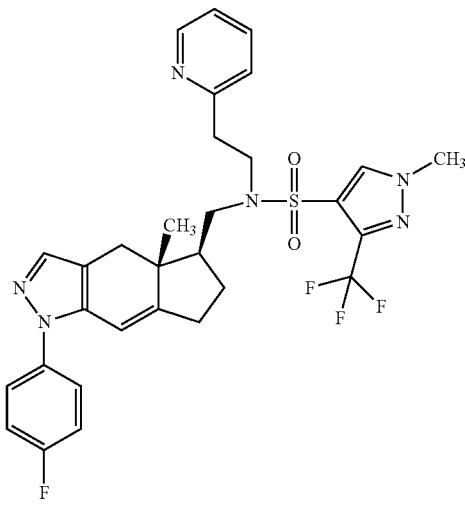 | N-{[(4αR,5S)-1-(4-fluorophenyl)-4α-methyl-1,4,4α,5,6,7-hexahydrocyclopenta[f]indazol-5-yl]methyl}-1-methyl-N-(2-pyridin-2-ylethyl)-3-(trifluoromethyl)-1H-pyrazole-4-sulfonamide | 615.2149 |

-continued

| Ex. | STRUCTURE | NAME | M + 1 |
|---|---|---|---|
| 151 | 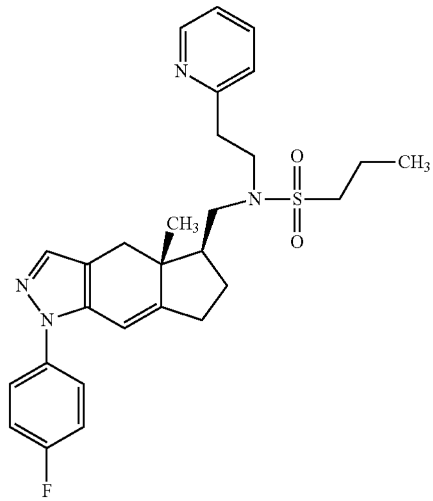 | N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)propane-1-sulfonamide | 509.2363 |
| 152 | 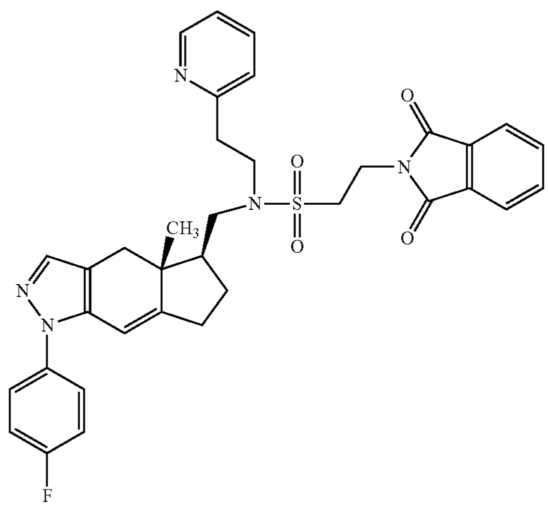 | 2-(1,3-dioxo-1,3-dihydro-2H-isoindol-2-yl)-N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)ethanesulfonamide | 640.2373 |
| 153 | 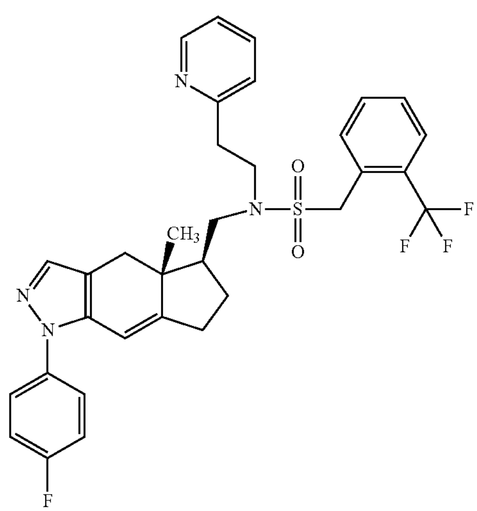 | N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)-1-[2-(trifluoromethyl)phenyl]methanesulfonamide | 625.2239 |

| Ex. | STRUCTURE | NAME | M + 1 |
|---|---|---|---|
| 154 | 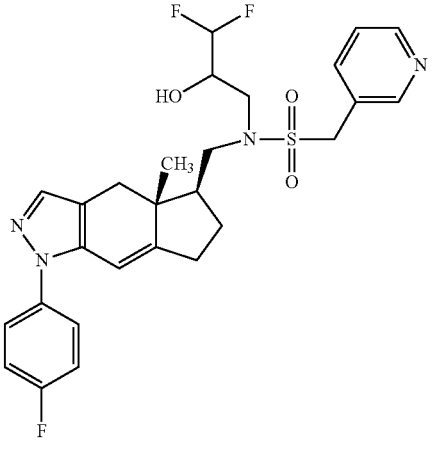 | N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide | 547.1971 |
| 155 | 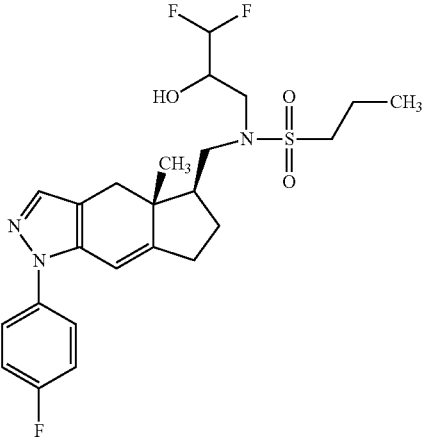 | N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}propane-1-sulfonamide | 498.2020 |
| 156 | 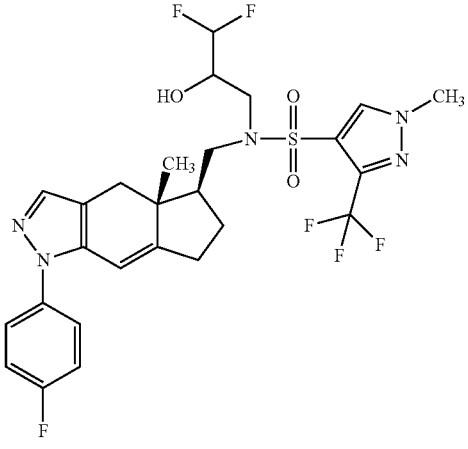 | N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonamide | 604.1808 |

US 8,299,048 B2

| Ex. | STRUCTURE | NAME | M + 1 |
|---|---|---|---|
| 157 | 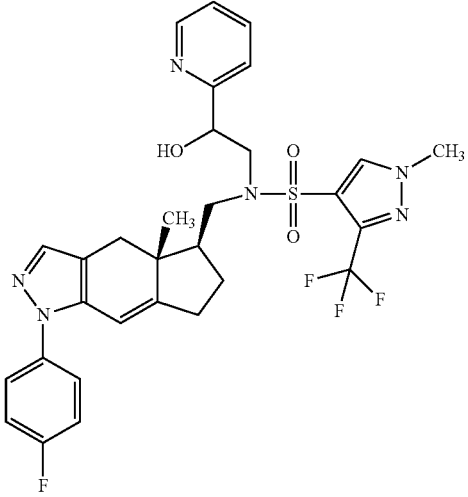 | N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-2-ylethyl)-1-methyl-3-(trifluoromethyl)-1H-pyrazole-4-sulfonamide | 631.2103 |
| 158 | 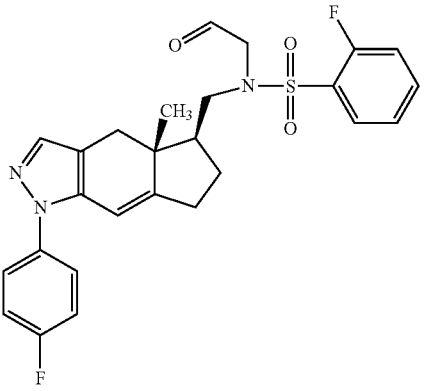 | 2-fluoro-N-{[(4αR,5S)-1-(4-fluorophenyl)-4α-methyl-1,4,4α,5,6,7-hexahydrocyclopenta[f]indazol-5-yl]methyl}-N-(2-oxoethyl)benzenesulfonamide | 498.1644 |
| 159 | 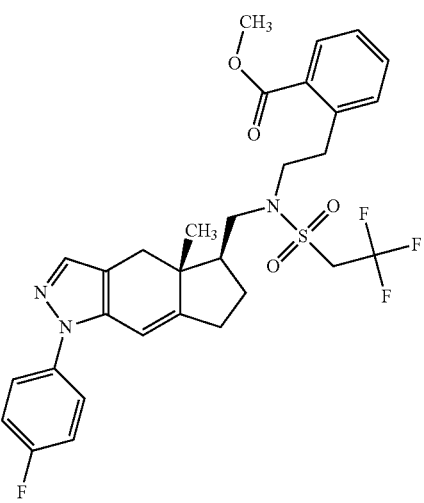 | methyl 2-(2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}ethyl)benzoate | 606.2037 |

-continued

| Ex. | STRUCTURE | NAME | M + 1 |
|---|---|---|---|
| 160 | 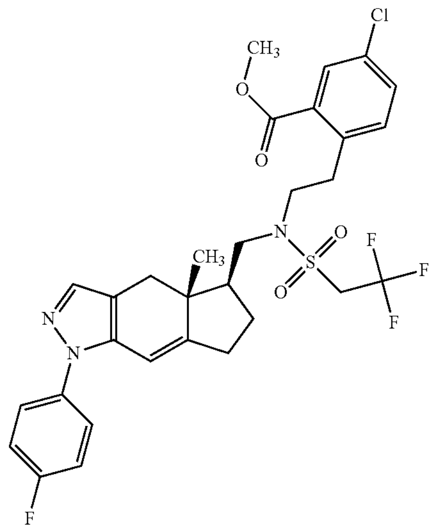 | methyl 5-chloro-2-(2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}ethyl)benzoate | 640.1646 |
| 161 | 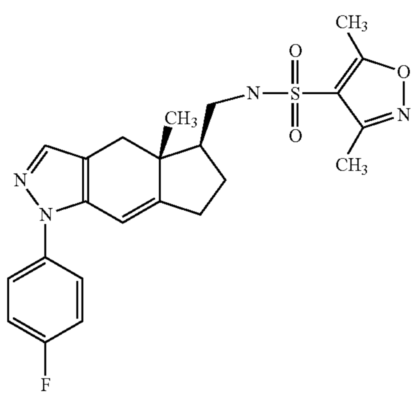 | N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide | 457.1698 |
| 162 | 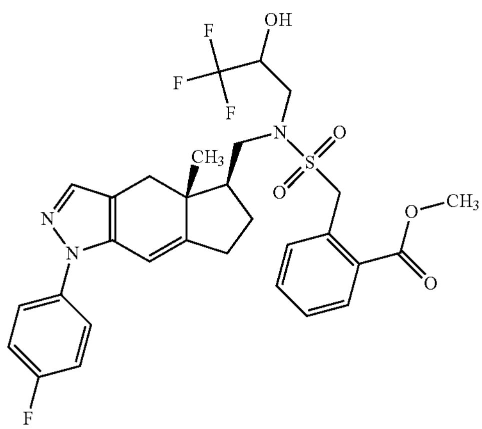 | methyl 2-({[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzoate | 622.1984 |

-continued

| Ex. | STRUCTURE | NAME | M + 1 |
|---|---|---|---|
| 163 | 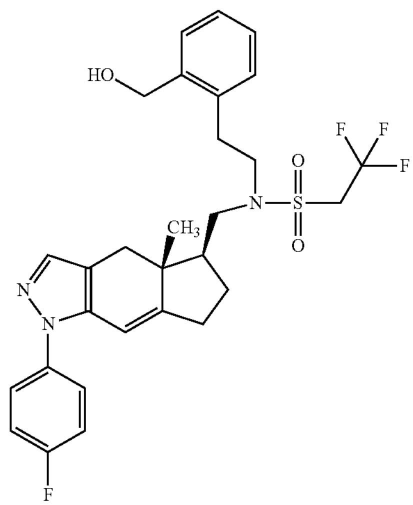 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-{2-[2-(hydroxymethyl)phenyl]ethyl}ethanesulfonamide | 578.2086 |
| 164 | 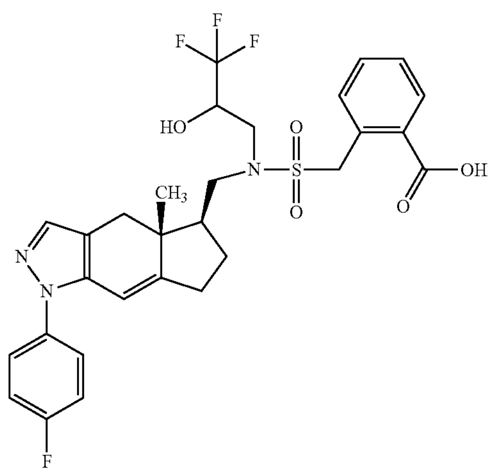 | 2-(({[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzoic acid | 608.1842 |
| 165 | 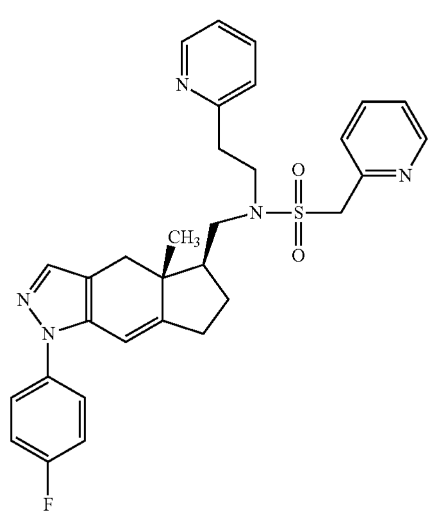 | N-{[(4αR,5S)-1-(4-fluorophenyl)-4α-methyl-1,4,4α,5,6,7-hexahydrocyclopenta[f]indazol-5-yl]methyl}-1-pyridin-2-yl-N-(2-pyridin-2-ylethyl)methanesulfonamide | 558.2339 |

-continued

| Ex. | STRUCTURE | NAME | M + 1 |
|---|---|---|---|
| 166 | 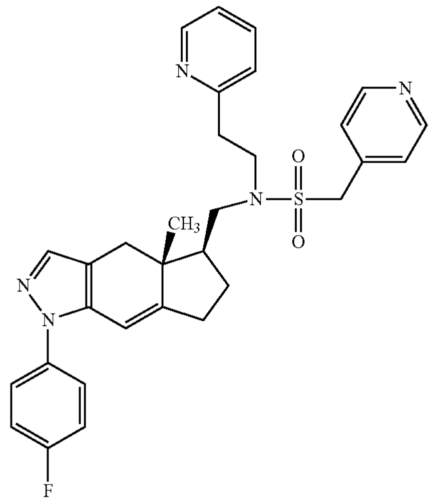 | N-{[(4αR,5S)-1-(4-fluorophenyl)-4α-methyl-1,4,4α,5,6,7-hexahydrocyclopenta[f]indazol-5-yl]methyl}-1-pyridin-4-yl-N-(2-pyridin-2-ylethyl)methanesulfonamide | 558.2344 |
| 167 | 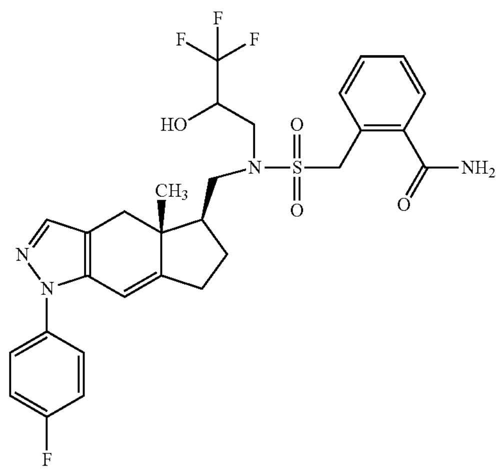 | 2-({[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzamide | 607.2606 |
| 168 | 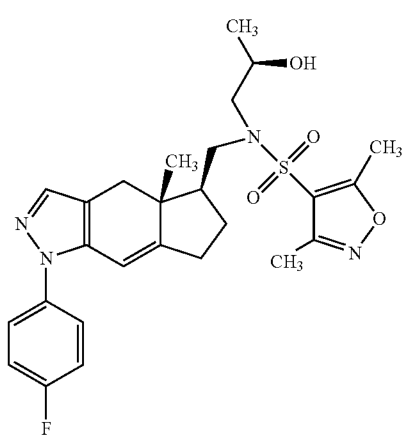 | N-{[(4αR,5S)-1-(4-fluorophenyl)-4α-methyl-1,4,4α,5,6,7-hexahydrocyclopenta[f]indazol-5-yl]methyl}-N-[(2R)-2-hydroxypropyl]-3,5-dimethylisoxazole-4-sulfonamide | 515.2157 |

-continued

| Ex. | STRUCTURE | NAME | M + 1 |
|---|---|---|---|
| 169 | 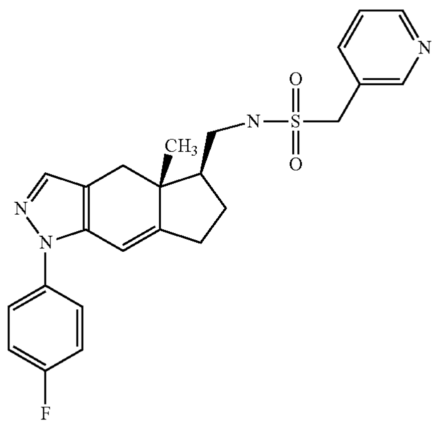 | N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide | 453.1765 |
| 170 | 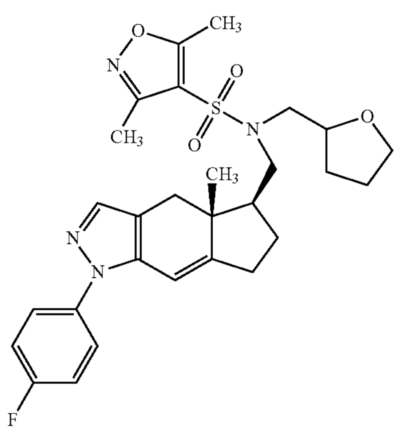 | N-{[(4αR,5S)-1-(4-fluorophenyl)-4α-methyl-1,4,4α,5,6,7-hexahydrocyclopenta[f]indazol-5-yl]methyl}-3,5-dimethyl-N-(tetrahydrofuran-2-ylmethyl)isoxazole-4-sulfonamide | 541.2284 |
| 171 | 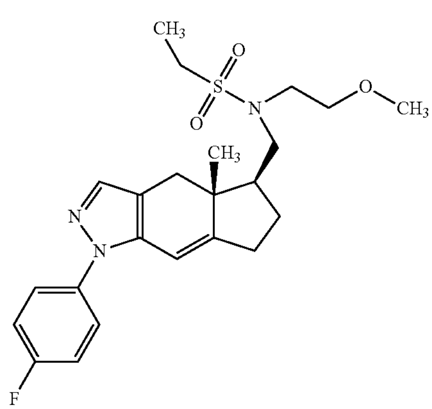 | N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide | 448.2 |

| Ex. | STRUCTURE | NAME | M + 1 |
|---|---|---|---|
| 172 | 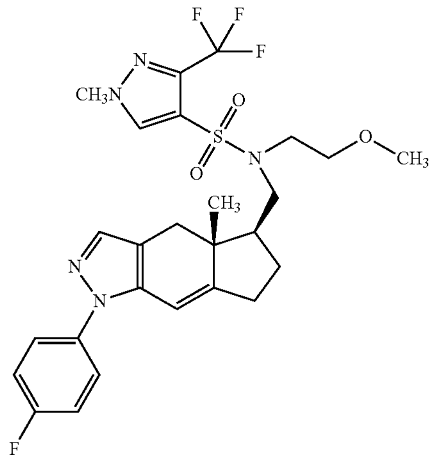 | N-{[(4αR,5S)-1-(4-fluorophenyl)-4α-methyl-1,4,4α,5,6,7-hexahydrocyclopenta[f]indazol-5-yl]methyl}-N-(2-methoxyethyl)-1-methyl-3-(trifluoromethyl)-1H-pyrazole-4-sulfonamide | 568.1987 |
| 173 | 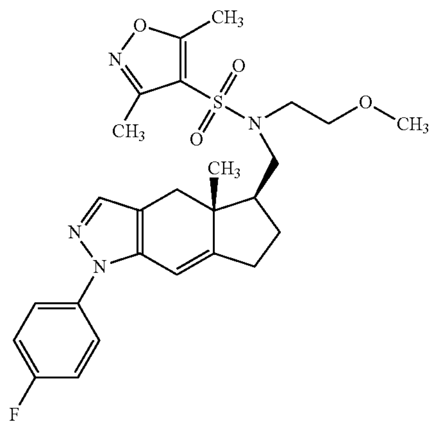 | N-{[(4αR,5S)-1-(4-fluorophenyl)-4α-methyl-1,4,4α,5,6,7-hexahydrocyclopenta[f]indazol-5-yl]methyl}-N-(2-methoxyethyl)-3,5-dimethylisoxazole-4-sulfonamide | 515.1522 |
| 174 | 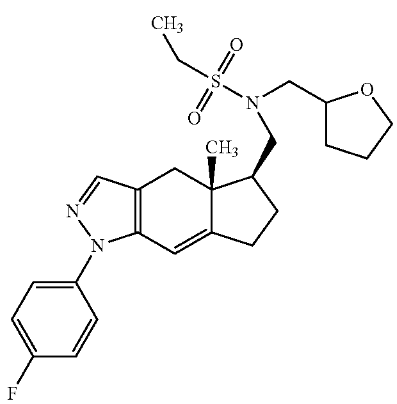 | N-{[(4αR,5S)-1-(4-fluorophenyl)-4α-methyl-1,4,4α,5,6,7-hexahydrocyclopenta[f]indazol-5-yl]methyl}-N-(tetrahydrofuran-2-ylmethyl)ethanesulfonamide | 474.2237 |

| Ex. | STRUCTURE | NAME | M + 1 |
|---|---|---|---|
| 175 | 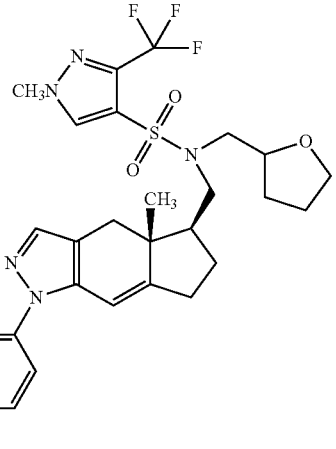 | N-{[(4αR,5S)-1-(4-fluorophenyl)-4α-methyl-1,4,4α,5,6,7-hexahydrocyclopenta[f]indazol-5-yl]methyl}-1-methyl-N-(tetrahydrofuran-2-ylmethyl)-3-(trifluoromethyl)-1H-pyrazole-4-sulfonamide | 592.1982 |
| 176 | 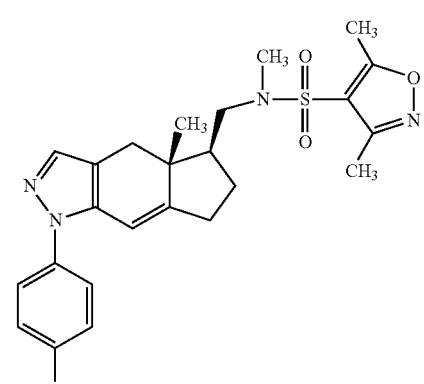 | N-{[(4αR,5S)-1-(4-fluorophenyl)-4α-methyl-1,4,4α,5,6,7-hexahydrocyclopenta[f]indazol-5-yl]methyl}-N,3,5-trimethylisoxazole-4-sulfonamide | 471.1882 |
| 177 | 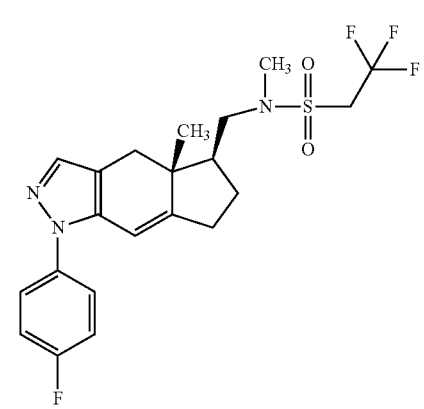 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-methylethanesulfonamide | 458.1537 |

-continued

| Ex. | STRUCTURE | NAME | M + 1 |
|---|---|---|---|
| 178 | 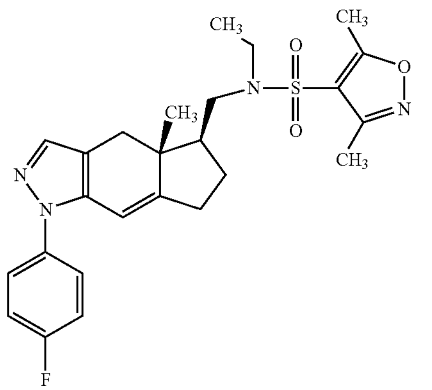 | N-ethyl-N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide | 485.2043 |
| 179 | 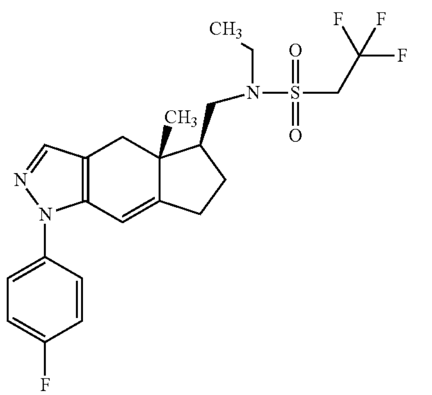 | N-ethyl-2,2,2-trifluoro-N-{[(4αR,5S)-1-(4-fluorophenyl)-4α-methyl-1,4,4α,5,6,7-hexahydrocyclopenta[f]indazol-5-yl]methyl}ethanesulfonamide | 472.1697 |
| 180 | 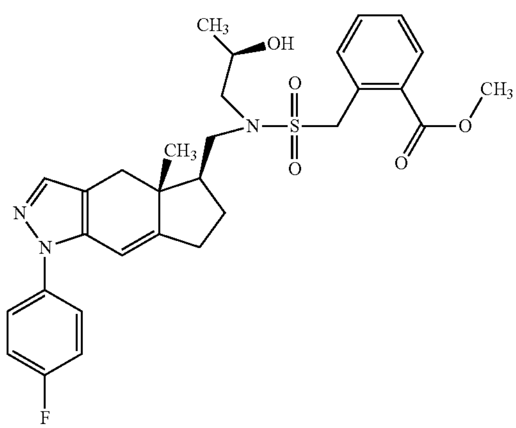 | methyl 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzoate | 568.2322 |
| 181 | 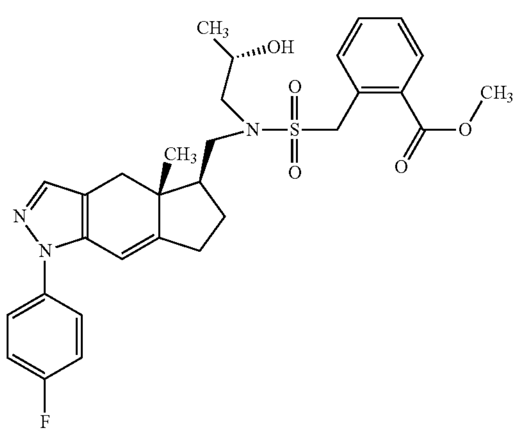 | methyl 2-[({{[(4αR,5S)-1-(4-fluorophenyl)-4α-methyl-1,4,4α,5,6,7-hexahydrocyclopenta[f]indazol-5-yl]methyl}[(2S)-2-hydroxypropyl]amino}sulfonyl)methyl]benzoate | 568.2315 |

| Ex. | STRUCTURE | NAME | M + 1 |
|---|---|---|---|
| 182 | 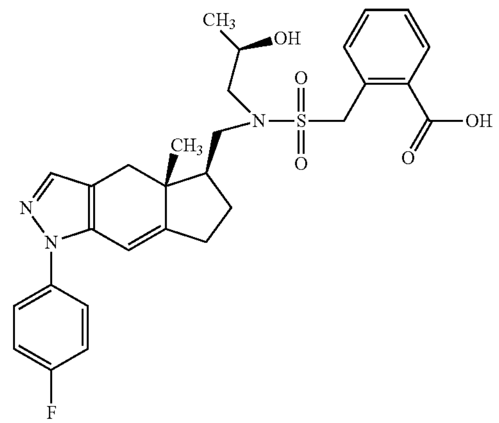 | 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzoic acid | 554.2148 |
| 183 | 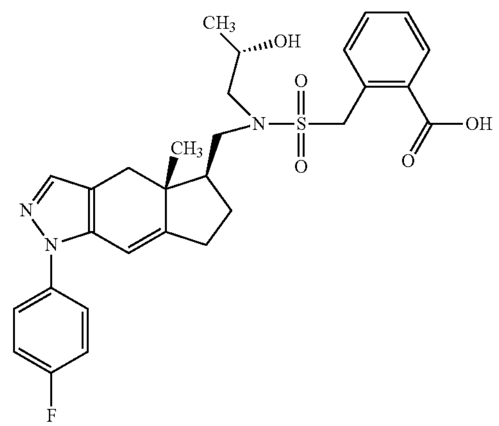 | 2-[({{[(4αR,5S)-1-(4-fluorophenyl)-4α-methyl-1,4,4α,5,6,7-hexahydrocyclopenta[f]indazol-5-yl]methyl}[(2S)-2-hydroxypropyl]amino}sulfonyl)methyl]benzoic acid | 554.2120 |
| 184 | 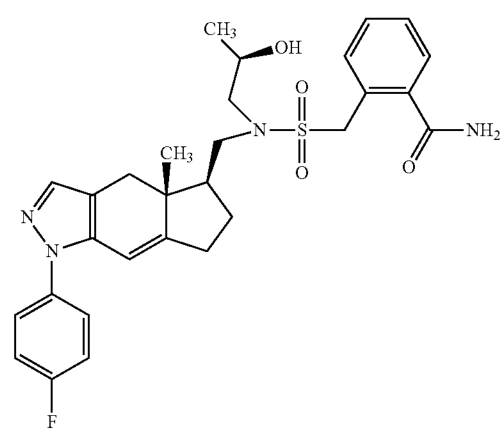 | 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzamide | 553.2321 |

| Ex. | STRUCTURE | NAME | M + 1 |
|---|---|---|---|
| 185 | 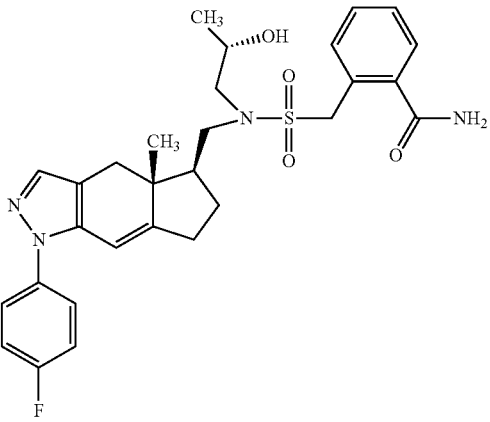 | 2-[({{[(4αR,5S)-1-(4-fluorophenyl)-4α-methyl-1,4,4α,5,6,7-hexahydrocyclopenta[f]indazol-5-yl]methyl}[(2S)-2-hydroxypropyl]amino}sulfonyl)methyl]benzamide | 553.2318 |
| 186 | 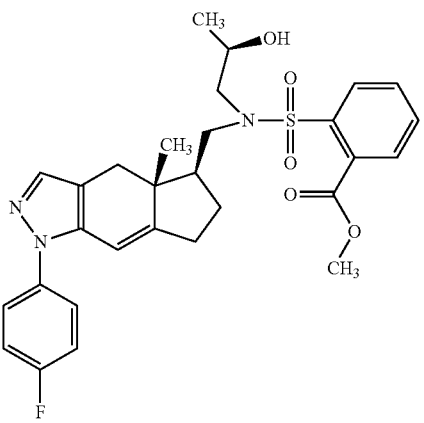 | methyl 2-({{{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)benzoate | 554.2168 |
| 187 | 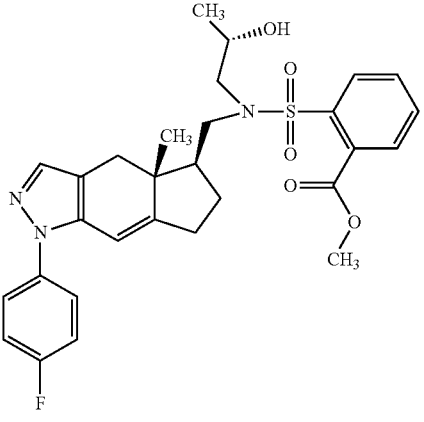 | methyl 2-({{{[(4αR,5S)-1-(4-fluorophenyl)-4α-methyl-1,4,4α,5,6,7-hexahydrocyclopenta[f]indazol-5-yl]methyl}[(2S)-2-hydroxypropyl]amino}sulfonyl)benzoate | 554.2152 |

-continued

| Ex. | STRUCTURE | NAME | M + 1 |
|---|---|---|---|
| 188 | 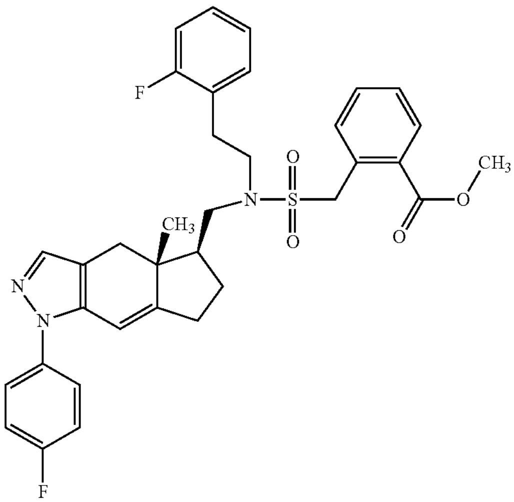 | methyl 2-{[([2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]methyl}benzoate | 632.2420 |
| 189 | 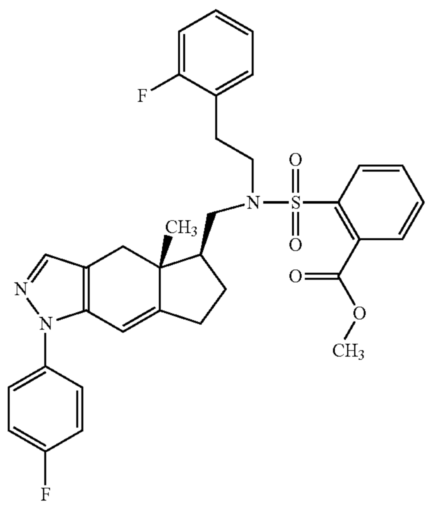 | methyl 2-[([2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]benzoate | 618.2283 |
| 190 | 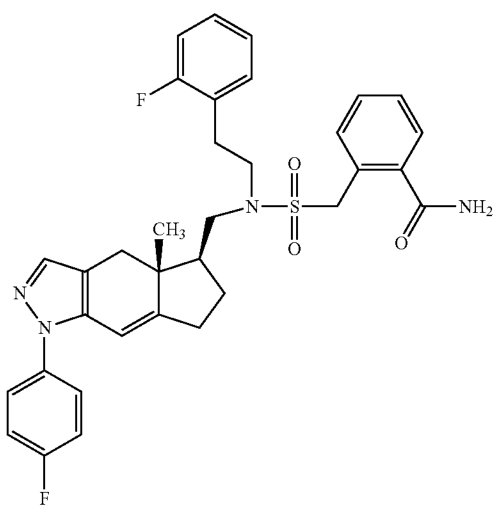 | 2-{[([2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]methyl}benzamide | 617.2442 |

| Ex. | STRUCTURE | NAME | M + 1 |
|---|---|---|---|
| 191 | 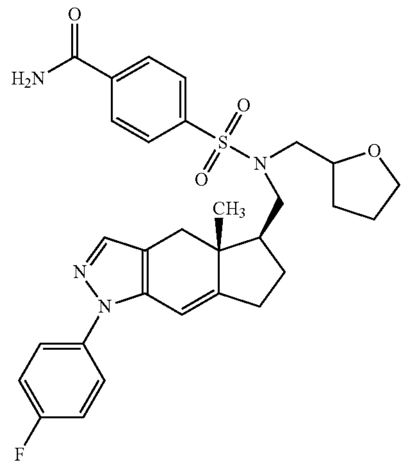 | 4-{[{[(4αR,5S)-1-(4-fluorophenyl)-4α-methyl-1,4,4α,5,6,7-hexahydrocyclopenta[f]indazol-5-yl]methyl}(tetrahydrofuran-2-ylmethyl)amino]sulfonyl}benzamide | 565.2 |
| 192 | 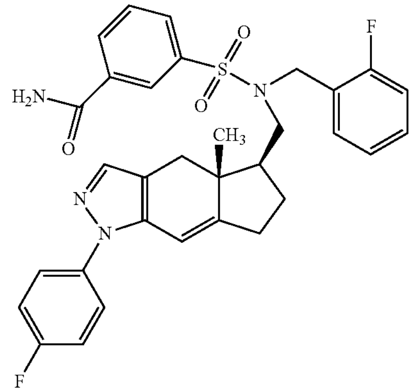 | 3-[((2-fluorobenzyl){[(4αR,5S)-1-(4-fluorophenyl)-4α-methyl-1,4,4α,5,6,7-hexahydrocyclopenta[f]indazol-5-yl]methyl}amino)sulfonyl]benzamide | 589.2 |
| 193 | 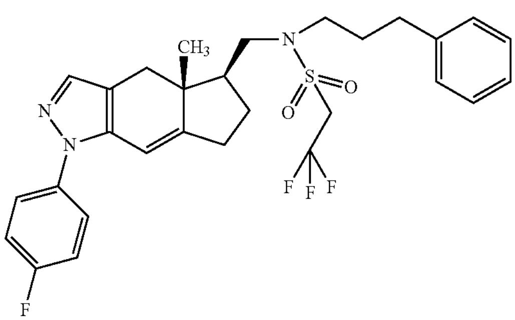 | 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(3-phenylpropyl)ethanesulfonamide | 562.2124 |
| 194 | 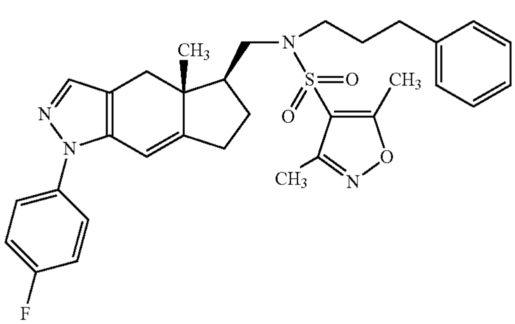 | N-{[(4αR,5S)-1-(4-fluorophenyl)-4α-methyl-1,4,4α,5,6,7-hexahydrocyclopenta[f]indazol-5-yl]methyl}-3,5-dimethyl-N-(3-phenylpropyl)isoxazole-4-sulfonamide | 575.247 |

-continued

| Ex. | STRUCTURE | NAME | M + 1 |
|---|---|---|---|
| 195 | 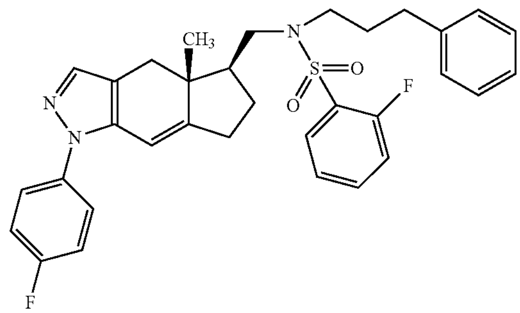 | 2-fluoro-N-{[(4αR,5S)-1-(4-fluorophenyl)-4α-methyl-1,4,4α,5,6,7-hexahydrocyclopenta[f]indazol-5-yl]methyl}-N-(3-phenylpropyl)benzenesulfonamide | 574.2309 |
| 196 | 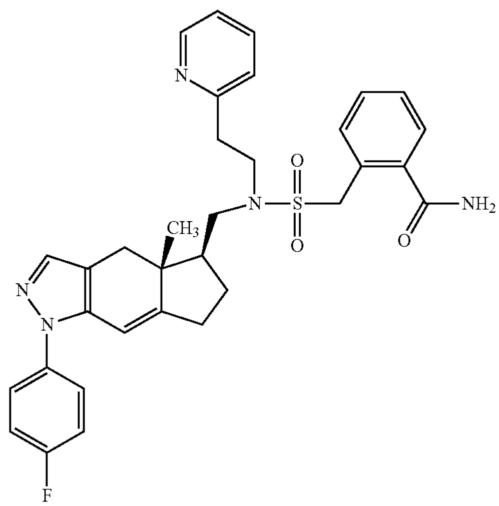 | 2-({[{[(4αR,5S)-1-(4-fluorophenyl)-4α-methyl-1,4,4α,5,6,7-hexahydrocyclopenta[f]indazol-5-yl]methyl}(2-pyridin-2-ylethyl)amino]sulfonyl}methyl)benzamide | 600.2476 |
| 197 | 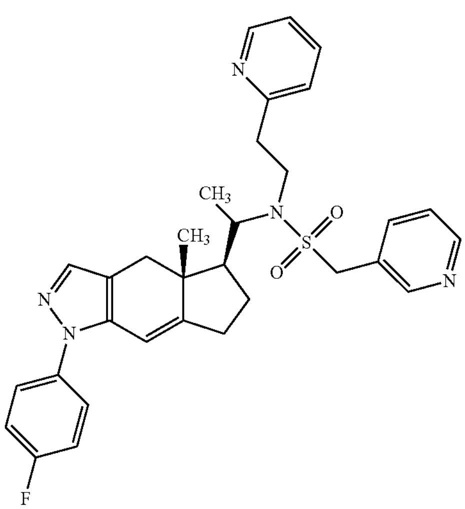 | N-{1-[(4αR)-1-(4-fluorophenyl)-4α-methyl-1,4,4α,5,6,7-hexahydrocyclopenta[f]indazol-5-yl]ethyl}-1-pyridin-3-yl-N-(2-pyridin-2-ylethyl)methanesulfonamide | 572.2 |

| Ex. | STRUCTURE | NAME | M + 1 |
|---|---|---|---|
| 198 | 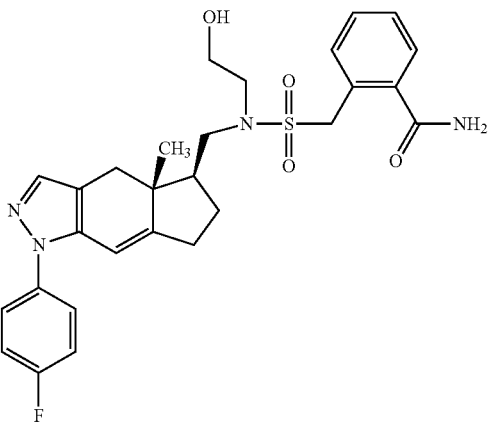 | 2-({[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}methyl)benzamide | 539.2 |
| 199 | 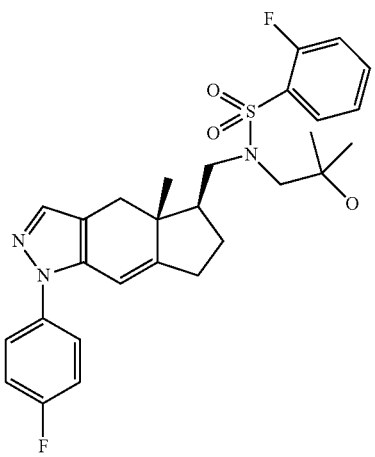 | 2-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-methylpropyl)benzenesulfonamide | 528.6 |

| Ex. | STRUCTURE | NAME | M + 1 |
|---|---|---|---|
| 200 | 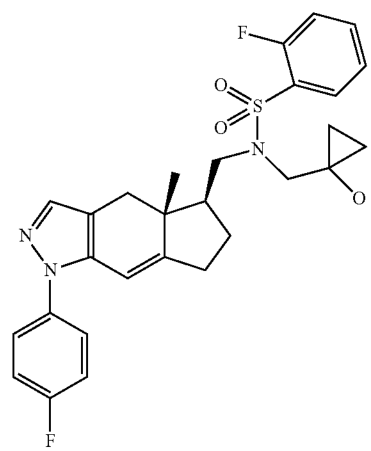 | 2-fluoro-N-{[(4αR,5S)-1-(4-fluorophenyl)-4α-methyl-1,4,4α,5,6,7-hexahydrocyclopenta[f]indazol-5-yl]methyl}-N-[(1-hydroxycyclopropyl)methyl]benzenesulfonamide | 526.6 |
| 201 | 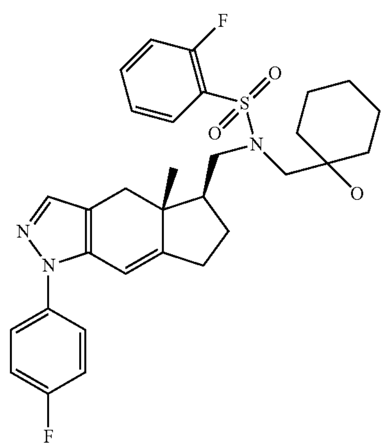 | 2-fluoro-N-{[(4αR,5S)-1-(4-fluorophenyl)-4α-methyl-1,4,4α,5,6,7-hexahydrocyclopenta[f]indazol-5-yl]methyl}-N-[(1-hydroxycyclohexyl)methyl]benzenesulfonamide | 568.6 |
For examples 93, 109 and 197, the following modification to the scheme was made:
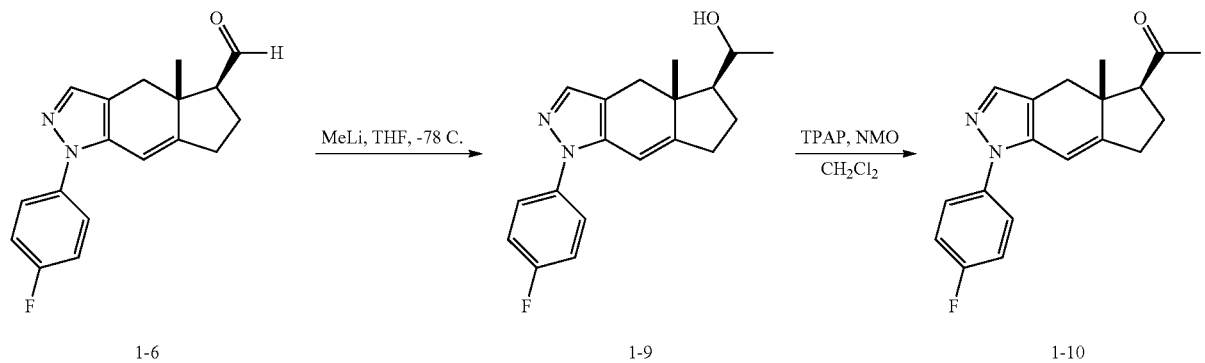
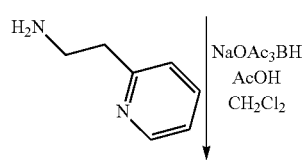

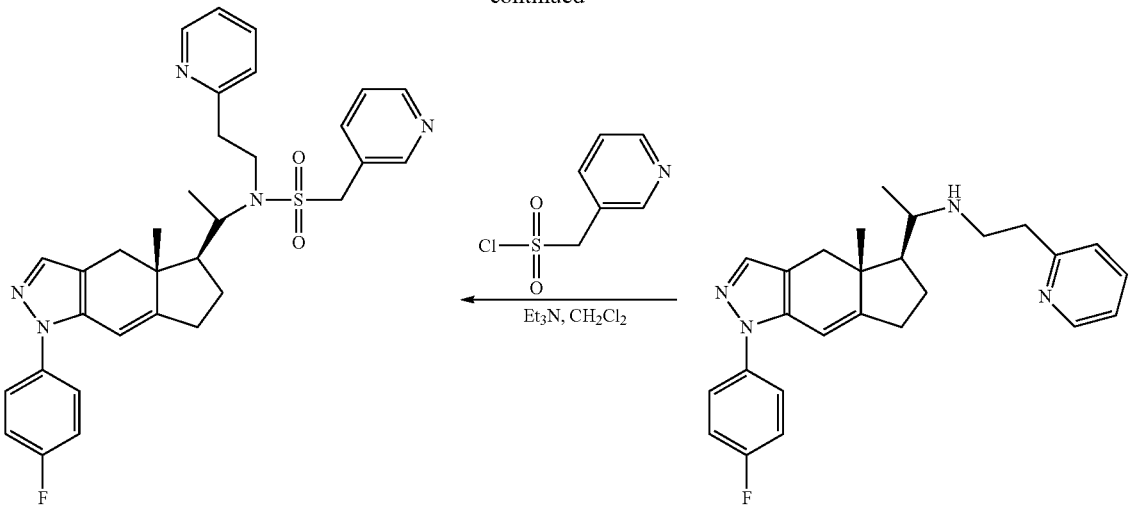

Biological Evaluation
Biological Evaluation (GR BIND)

The compounds exemplified in the present application exhibited activity in one or more of the following assays.

Ligand Binding Assay

Materials:

Binding Buffer: TEGM (10 mM Tris-HCl, 1 mM EDTA, 10% glycerol, 1 mM beta-mecaptoethanol, 10 mM Sodium Molybdate, pH 7.2)

50% HAP Slurry: Calbiochem Hydroxylapatite, Fast Flow, in 10 mM Tris, pH 8.0 and 1 mM EDTA.

Wash Buffer: 40 mM Tris, pH7.5, 100 mM KCl, 1 mM EDTA and 1 mM EGTA. 95% EtOH

Dexmethasone-methyl-$^3$H, (DEX*); (Amersham cat# TRK645)

Dexamethasone(DEX) (Sigma, cat# D1756):

Hydroxylapatite Fast Flow; Calbiochem Cat#391947

Molybdate=Molybdic Acid (Sigma, M1651)

MDA-MB-453 cell culture media:

| RPMI 1640 (Gibco 11835-055) w/23.8 mM NaHCO$_3$, 2 mM L-glutamine | Final conc. |
|---|---|
| in 500 mL of complete media | |
| 10 mL (1M Hepes) | 20 mM |
| 5 mL (200 mM L-glu) | 4 mM |
| 0.5 mL (10 mg/mL human insulin) in 0.01N HCl | 10 μg/mL |
| Calbiochem#407694-S) | |
| 50 mL FBS (Sigma F2442) | 10% |
| 1 mL (10 mg/mL Gentamicin Gibco#15710-072) | 20 μg/mL |

Cell Passaging

Cells (Hall R. E., et al., *European Journal of Cancer*, 30A: 484-490 (1994)) MDA-MB-453 (ATCC) cultured in RPMI 1640 (Gibco 11835-055) containing 20 mM Hepes, 4 mM L-glu, 10 ug/ml of human insulin (Sigma, I-0259), 10% FBS and 20 ug/ml of Gentamicin (Gibco#15710-072) are rinsed twice in PBS. Phenol red-free Trypsin-EDTA is diluted in the same PBS1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added. The cells are counted at this point, then diluted to the appropriate concentration and split into flasks or dishes for further culturing (Usually 1:3 to 1:6 dilution).

Preparation of MDA-MB-453 Cell Lysate

When the cells are 70 to 85% confluent, they are detached as described above, and collected by centrifuging at 1000 g for 10 minutes at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of 10$^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 μL of supernatant, the test compound can be prepared in 50 μL of the TEGM buffer.

Procedure for Multiple Compound Screening

1×TEGM buffer is prepared, and the isotope-containing assay mixture is prepared in the following order: EtOH (2% final concentration in reaction), 3H-DEX (Amersham Biosciences) and 1×TEGM. [e.g. For 100 samples, 200 μL (100× 2) of EtOH+4.25 μL of 1:10 $^3$H—Dex stock+2300 μL (100× 23) 1×TEGM]. The compound is serially diluted, e.g., if starting final conc. is 1 μM, and the compound is in 25 μL of solution, for duplicate samples, 75 μL of 4×1 μM solution is made and 3 μL of 100 μM is added to 72 μL of buffer, and 1:5 serial dilution.

25 μL of $^3$H-DEX (6 nM) trace and 25 μL compound solution are first mixed together, followed by addition of 50 μL receptor solution. The reaction is gently mixed, spun briefly at about 200 rpm and incubated at 4° C. overnight. 100 μL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard).

The washing process transfers HAP pellet containing ligand-bound expressed receptor to Unifilter-96 GF/B filter plate (Packard). The HAP pellet on the filter plate is incubated with 50 μL of MICROSCINT (Packard) scintillint for 30 minutes before being counted on the TopCount microscintillation counter (Packard). $IC_{54}$s are calculated using DEX as a reference.

Examples 1 to 201 were tested in the ligand binding assay and demonstrated IC50s less than 1000 nM.

Trans-Activation Modulation of Glucocorticoid Receptor (GRAMMER)

This assay assesses the ability of test compounds to control transcription from the MMTV-LUC reporter gene in lung adenocarcinoma A549 cells or MDA-MB-453 cells, a human breast cancer cell line that naturally expresses the human GR. The assay measures induction of a modified MMTV LTR/promoter linked to the LUC reporter gene.

The routine transient assay consists of plating 7,000-25,000 cells/well of a white, clear-bottom 96-well plate. Alternatively, 384-well plates can be used at a cell concentration of 10,000/well. The media that the cells are plated in is "exponential growth medium" which consists of phenol red-free RPMI1640 containing 10% FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media. It is then gently mixed with the FuGene6/DNA mix and plated onto the 96 or 384-well plate, all the wells receive 100 uL or 40 uL, respectively, of medium+lipid/DNA complex then incubated 37° C. overnight. The transfection cocktail consists of serum-free OptiMEM, FuGene6 reagent and DNA. The manufacturer's (Roche Biochemical) protocol for cocktail setup is as follows: The lipid to DNA ratio is approximately 2.5:1 and the incubation time is 20 min at room temperature. Sixteen to 24 hours after transfection, the cells are treated with dexamethasone to a final concentration of 10 nM as well as the compound of interest, such that final DMSO (vehicle) concentration is equal to or less than 1%. Each plate also contains samples that are treated with 10 nM dexamethasone alone, which is used as the 100% activity control. The cells are exposed to the compounds for 24 hours. After 24 hours, the cells are lysed by a Promega cell culture lysis buffer for approximately 30 min and then the luciferase activity in the extracts is assayed in the 96-well format luminometer. In 384-well format, Steady-Glo (Promega) or Steady-Lite (PerkinElmer) can be used by adding an equal volume of reagent to the media present in each well. Activity induced by 10 nM dexamethasone alone is set at 100% activity. Antagonist activity is calculated by determining the decrease in dexamethasone-induced activity in response to compound treatment relative to samples that were treated with dexamethasone alone. Results are expressed as % inhibition of 10 nM dexamethasone activity or as fold of 10 nM dexamethasone activity. This transactivation assay can be performed in an agonist and antagonist mode to identify these different activities.

Activity of test compounds is calculated as the $E_{max}$ relative to the activity obtained with 300 nM dexamethasone. Activity of test compounds is calculated as the $E_{max}$ relative to the activity obtained with 300 nM DEX. The exemplified tissue selective glucocorticoid receptor modulators of the present invention display partial agonist activity in this assay of greater than 5%.

The action of compounds is also tested in an antagonist mode (Anti-GRAMMER) in which the cells are treated with medium containing an agonist such as 10 nM DEX and the ability to agents to inhibit the activation by an agonist is measured.

Transrepression Assay (GITAR)

This assay assesses the ability of test compounds to control transcription from the TNFα-β-lactamase reporter gene in U937 cells, a human myelomonocytic leukemia cell line that naturally expresses the human GR. The assay measures compound dependent-repression of the TNFa promoter linked to a reporter gene.

The human U937 cells that had been stably transfected with the TNF-α promoter driving β-lactamase are used for this assay. U937 cells contain an endogenous glucocorticoid receptor (GR). Cells are maintained in RPMI 1640 Growth medium (Gibco Cat#11875-093) containing 25 mM HEPES, 10% FBS, 2 mM L-Glutamine, 1 mM Sodium pyruvate, 25 μg/ml Gentamicin (Gibco Cat#15710-064), 1:1000 2-Mercaptoethanol (Gibco Cat#21985-023) and 0.8 mg/ml G418 (Gibco Cat#10131-027). The density of the cells in the flask needs to be about $1\times10^6$–$3\times10^6$/ml at the time of harvest. Usually, the cells are split to 1.2~$1.4\times10^5$/ml (1:10) 3 days prior to the assay. 50,000 cells/well are plated in 96 well black-walled plates the day of assay. Test compounds are added 10 μL/well, and cells are incubated at 37° C. for 30~45 min. For assaying compounds, first dilute 1:10 in DMSO to make 1 mM, then further dilute 1:100 in medium to make 10× stock prior to adding to the cells. Add 50 ng/mlPMA (Sigma, cat# P8139) 10 μL/well to a final concentration 5 ng/ml, and 1 μg/ml LPS (Sigma, cat# L4130) 10 μL/well to a final concentration 100 ng/ml. Incubate cells at 37° C. overnight for ~18 hr. PMA is stored frozen as 100 μg/ml stock in DMSO. Dilute 1:10 in DMSO for a working stock of 10 μg/ml and store at −20 C. For assaying, dilute the 10 μg/ml working stock 1:200 in medium to make a 10× solution (50 ng/ml). Store frozen LPS at 1 mg/ml in PBS, dilute 1:1000 in medium to make 10× (1 μg/ml) for the assay. Add 6× loading buffer (CCF2-AM) 20 μL/well, and incubate at room temperature for 70~90 min. Read plates on CytoFluor II Plate Reader according to manufacture suggested protocols. The activity repressed by 100 nM dexamethasone alone is set as 100% activity.

Examples 1 to 201 were tested in the transrepression assay and demonstrated maximal activity greater than 5%.

Microarray Analysis

All cell culture reagents were purchased from Invitrogen Life Tech, Carlsbad Calif. A549 cells were grown in phenol red-free DMEM/F12 medium supplemented with 10% FBS. Cells were grown at 37° C. with 5% $CO_2$. Using the RNeasy Kit (Qiagen Corp, Valencia Calif.), total RNA was extracted and purified from A549 cells treated with different GC compounds for 24 hours, at a fully active dose. These cells express large amount of the GR and are very responsive to GC treatment. All samples were compared against cells treated with vehicle. Expression levels of 23000 genes were measured using oligonucleotide microarrays purchased from Agilent Technologies, Inc. Each comparison was done on a pair of microarrays with reversed fluorophores. Raw image intensity data were processed according to the method described in U.S. Pat. No. 6,351,712. The method was used to remove dye bias and to derive a Rosetta probability (p) and fold change value for each gene and each sample pair. Furthermore, for each gene an ANOVA model was constructed across all treatments to derive error estimates. P values for evaluating expression differences were computed using a Bayesian adjusted t-test that was developed by Lonnstedt and Speed (2002) and extended by Smyth (2003). A gene was declared differentially expressed in any particular comparison if it satisfied two critera:

1. The Rosetta p value had to be less than 0.1 and the Rosetta fold change value had to be greater than 1.4 in at least one of the treatments.
2. The ANOVA p value had to be less than 0.01 and the fold change greater than 2 in the comparison under consideration.

In Vivo Inflammation Assay

Intact adult (6 month old) female Sprague-Dawley rats are used in the oxazolone (OX) contactdermatitis model. Rats were sensitized on the ventral abdomen with OX on Day 0. On Days 7 and 9, a randomly-selected ear was challenged (same ear each time) with OX; the other was treated with vehicle. Daily treatment begun on Day 7 and continued for 7d with test compounds at different doses and 1.3 mpk 6-methlyprednisolone or 0.1 mpk DEX as positive controls. The thickness of both ears are measured on Days 11 and 14. Necropsy occurred on Day 14. The rat is first weighed, then anesthetized in a $CO_2$ chamber until near death.

Approximately 5 ml whole blood is obtained by cardiac puncture. The rat is then examined for certain signs of death and completeness. Tissues are dissected in a highly stylized fashion. The following endpoints were evaluated: a) inhibiting ear inflammation induced by oxazalone, b) raising serum insulin, c) reducing serum ACTH, d) reducing spleen weight, e) reducing skin thickness, f) reducing body weight, g) increasing expression of bone-related genes with potential relationship to negative glucocorticoid effects on bone; e) changes in molecular markers that correlate with skin inflammation, skin thinning, muscle atrophy and glucose metabolism in liver. All blood samples were collected between 1330-1530 hours, ~4-5 hrs after the last compound treatment.

Primary data for this assay are left and right ear thickness. Inter-ear thickness difference (etd) is used for the estimating the level of inflammation and effectiveness of the compounds is determined by their ability to reduce the increase the thickness of the inflamed ear. Back of the rat skin thickness, spleen weight, serum insulin as well as the effects of gcs on the expression of molecular markers in skin inflammation, skin atrophy, muscle atrophy and glucose metabolism in liver are measured. Data are analyzed by anova plus fisher plsd post-hoc test to identify intergroup differences.

| Compound number | GR BIND Ki (nM) | Transactivation A549 Cells GRAMMER | | Transrepression U937 Cells GITAR | | GITAR > GRAMM % SEP |
|---|---|---|---|---|---|---|
| | | IP (nM) | Emax (%) | IP (nM) | Emax (%) | |
| 1 | 1.8 | 350.7 | 31.6 | 406.8 | 73.5 | 41.9 |
| 2 | 0.6 | 218.1 | 50.5 | 259.8 | 73.3 | 22.7 |
| 3 | 0.8 | 368.2 | 39.3 | 406.6 | 65.1 | 25.8 |
| 4 | 2.2 | 293.8 | 16.9 | 256.0 | 53.1 | 36.2 |
| 5 | 1.0 | 421.5 | 2.9 | 222.8 | 19.2 | 16.2 |
| 6 | 0.9 | 402.4 | 13.0 | 1010.0 | 49.0 | 36.0 |
| 7 | 0.4 | 351.4 | 36.3 | 388.8 | 56.0 | 19.7 |
| 8 | 1.9 | 37.0 | 4.9 | 424.0 | 17.4 | 12.4 |
| 9 | 2.2 | 1131.0 | 12.7 | 959.5 | 28.1 | 15.4 |
| 10 | 0.7 | 614.8 | 12.3 | 464.7 | 46.6 | 34.4 |
| 11 | 0.7 | 235.0 | 66.0 | 205.8 | 89.1 | 23.1 |
| 12 | 1.8 | 331.4 | 34.4 | 279.8 | 64.2 | 29.8 |
| 13 | 0.6 | 82.9 | 8.3 | 305.4 | 16.1 | 7.8 |
| 14 | 1.6 | 344.3 | 25.2 | 553.5 | 59.3 | 34.1 |
| 15 | 1.8 | 291.7 | 27.6 | 257.9 | 59.0 | 31.4 |
| 16 | 3.0 | 254.5 | 53.0 | 268.5 | 84.5 | 31.4 |
| 17 | 2.1 | 219.7 | 37.3 | 347.5 | 82.1 | 44.8 |
| 18 | 0.8 | 394.2 | 20.0 | 415.2 | 35.3 | 15.3 |
| 19 | 4.0 | 1187.0 | 20.6 | 1721.0 | 69.8 | 49.1 |
| 20 | 2.2 | 909.5 | 68.1 | 372.7 | 69.7 | 1.6 |
| 21 | 3.0 | 518.8 | 33.5 | 365.5 | 58.7 | 25.2 |
| 22 | 3.5 | 453.2 | 27.9 | 395.0 | 71.8 | 43.9 |
| 23 | 4.9 | 8787.0 | 2.7 | 2253.0 | 34.0 | 31.3 |
| 24 | 5.3 | 845.1 | 10.5 | 564.6 | 37.7 | 27.2 |
| 25 | 2.5 | 453.0 | 76.4 | 222.5 | 89.4 | 13.0 |
| 26 | 9.7 | 939.0 | 5.8 | 25.0 | 16.0 | 10.2 |
| 27 | 8.8 | 994.3 | 3.0 | 637.5 | 13.0 | 10.0 |
| 28 | 2.3 | 483.2 | 44.0 | 662.3 | 78.8 | 34.8 |
| 29 | 8.4 | 1712.0 | 4.7 | 838.4 | 30.9 | 26.2 |
| 30 | 7.6 | 1638.0 | 3.5 | 416.9 | 19.9 | 16.4 |
| 31 | 6.1 | 833.5 | 20.7 | 678.7 | 54.8 | 34.0 |
| 32 | 3.9 | 867.6 | 29.4 | 555.4 | 63.1 | 33.7 |
| 33 | 8.8 | 1051.0 | 15.2 | 1205.0 | 59.7 | 44.5 |
| 34 | 1.7 | 748.2 | 37.0 | 1775.0 | 45.9 | 8.9 |
| 35 | 5.1 | 443.3 | 4.9 | 777.4 | 39.5 | 34.6 |
| 36 | 2.5 | 744.5 | 22.7 | 540.0 | 72.2 | 49.5 |
| 37 | 10.7 | 2189.0 | 2.8 | 1354.0 | 33.8 | 30.9 |
| 38 | 6.4 | 5000.0 | 1.3 | 2340.0 | 33.8 | 32.5 |
| 39 | 8.1 | 5000.0 | 1.7 | 34.9 | 17.1 | 15.5 |
| 40 | 10.5 | 82.8 | 3.2 | 35.5 | 19.8 | 16.6 |
| 41 | 5.9 | 124.3 | 60.3 | 361.5 | 91.9 | 31.6 |
| 42 | 5.9 | 228.1 | 4.2 | 391.3 | 19.2 | 15.1 |
| 43 | 2.2 | 469.7 | 36.0 | 1099.0 | 71.8 | 35.8 |
| 44 | 1.6 | 621.8 | 44.8 | 1055.0 | 65.6 | 20.8 |
| 45 | 2.4 | 2887.0 | 11.4 | 1391.0 | 12.8 | 1.3 |
| 46 | 0.7 | 372.6 | 83.3 | 187.5 | 85.5 | 2.1 |
| 47 | 0.7 | 635.4 | 58.3 | 894.9 | 74.0 | 15.7 |
| 48 | 0.9 | 995.0 | 8.8 | 175.3 | 24.5 | 15.7 |
| 49 | 1.8 | 955.4 | 14.1 | 922.2 | 23.0 | 8.9 |
| 50 | 6.5 | 948.6 | 15.1 | 959.5 | 61.3 | 46.2 |
| 51 | 2.5 | 433.1 | 83.3 | 185.8 | 86.8 | 3.5 |
| 52 | 1.9 | 569.7 | 31.9 | 868.8 | 54.4 | 22.5 |
| 53 | 3.7 | 865.9 | 18.1 | 832.3 | 54.0 | 36.0 |
| 54 | 8.5 | 1080.0 | 8.2 | 1101.0 | 31.3 | 23.1 |
| 55 | 2.7 | 549.5 | 47.7 | 337.0 | 83.4 | 35.7 |
| 56 | 4.6 | 804.9 | 50.9 | 642.7 | 86.9 | 36.1 |
| 57 | 3.4 | 864.7 | 2.7 | 1200.0 | 23.8 | 21.0 |
| 58 | 2.3 | 1077.0 | 3.1 | 736.9 | 28.8 | 25.7 |
| 59 | 2.6 | 437.0 | 41.3 | 537.8 | 80.9 | 39.6 |
| 60 | 4.4 | 776.9 | 23.0 | 813.5 | 52.0 | 29.0 |
| 61 | 2.5 | 417.3 | 5.8 | 1554.0 | 31.3 | 25.5 |
| 62 | 3.5 | 404.3 | 26.0 | 855.6 | 68.5 | 42.5 |
| 63 | 9.1 | 1408.0 | 2.1 | 404.2 | 12.0 | 9.9 |
| 64 | 3.0 | 621.5 | 7.9 | 731.0 | 29.0 | 21.1 |
| 65 | 2.7 | 1085.0 | 19.6 | 894.2 | 61.0 | 41.3 |
| 66 | 7.9 | 1176.0 | 5.3 | 929.3 | 24.5 | 19.2 |
| 67 | 13.4 | 450.0 | 6.5 | 2063.0 | 29.3 | 22.8 |
| 68 | 3.6 | 950.6 | 10.0 | 757.0 | 32.9 | 22.9 |
| 69 | 8.7 | 852.2 | 12.6 | 2536.0 | 34.8 | 22.2 |
| 70 | 4.5 | 564.0 | 25.8 | 1008.0 | 40.8 | 15.1 |
| 71 | 5.0 | 256.9 | 63.1 | 302.3 | 82.3 | 19.2 |
| 72 | 1.4 | 474.5 | 35.3 | 486.5 | 60.8 | 25.5 |
| 73 | 3.1 | 363.9 | 25.4 | 363.5 | 81.4 | 56.0 |
| 74 | 3.0 | 1026.0 | 34.1 | 1144.0 | 44.1 | 9.9 |
| 75 | 2.5 | 450.4 | 14.4 | 473.2 | 28.8 | 14.4 |
| 76 | 7.7 | 1963.0 | 3.5 | 2110.0 | 13.0 | 9.5 |
| 77 | 1.8 | 901.0 | 17.9 | 1126.0 | 43.6 | 25.7 |
| 78 | 2.3 | 652.2 | 50.6 | 882.7 | 66.5 | 15.9 |
| 79 | 4.8 | 1318.0 | 7.5 | 1947.0 | 71.8 | 64.3 |
| 80 | 13.7 | 1141.0 | 6.0 | 2584.0 | 70.0 | 64.0 |
| 81 | 7.2 | 460.6 | 17.2 | 959.3 | 76.7 | 59.5 |
| 82 | 3.2 | 287.4 | 61.1 | 220.2 | 90.2 | 29.1 |
| 83 | 3.7 | 567.8 | 6.9 | 1317.0 | 59.5 | 52.6 |
| 84 | 2.6 | 441.9 | 19.7 | 799.2 | 86.0 | 66.3 |
| 85 | 6.9 | 73.7 | 1.6 | 4235.0 | 38.8 | 37.1 |
| 86 | 4.2 | 68.6 | 68.2 | 262.4 | 80.6 | 12.4 |
| 87 | 2.8 | 231.3 | 65.1 | 212.1 | 85.1 | 20.0 |
| 88 | 3.7 | 617.6 | 25.3 | 645.8 | 57.7 | 32.4 |
| 89 | 2.4 | 119.3 | 81.4 | 137.5 | 95.6 | 14.3 |
| 90 | 3.6 | 353.9 | 33.5 | 651.2 | 67.6 | 34.0 |
| 91 | 2.0 | 642.9 | 10.7 | 973.1 | 61.5 | 50.8 |

| Compound number | GR BIND Ki (nM) | Transactivation A549 Cells GRAMMER IP (nM) | Transactivation A549 Cells GRAMMER Emax (%) | Transrepression U937 Cells GITAR IP (nM) | Transrepression U937 Cells GITAR Emax (%) | GITAR > GRAMM % SEP |
|---|---|---|---|---|---|---|
| 92 | 3.0 | 504.4 | 41.6 | 493.2 | 68.5 | 26.9 |
| 93 | 2.7 | 295.7 | 50.9 | 231.2 | 71.8 | 20.8 |
| 94 | 2.9 | 422.8 | 43.9 | 412.4 | 75.5 | 31.6 |
| 95 | 5.2 | 559.5 | 70.4 | 464.1 | 73.1 | 2.7 |
| 96 | 1.1 | 152.4 | 65.7 | 124.2 | 85.0 | 19.3 |
| 97 | 0.3 | 48.9 | 83.8 | 49.0 | 85.9 | 2.2 |
| 98 | 1.5 | 239.5 | 76.7 | 64.3 | 89.9 | 13.2 |
| 99 | 1.4 | 235.7 | 62.1 | 64.4 | 86.8 | 24.6 |
| 100 | 2.1 | 397.2 | 64.9 | 191.6 | 79.1 | 14.2 |
| 101 | 3.4 | 181.7 | 62.8 | 61.1 | 95.4 | 32.6 |
| 102 | 2.6 | 202.9 | 78.3 | 95.1 | 86.5 | 8.2 |
| 103 | 1.7 | 366.8 | 68.8 | 177.2 | 76.5 | 7.7 |
| 104 | 9.8 | 257.7 | 9.2 | 153.3 | 10.2 | 1.0 |
| 105 | 1.7 | 192.6 | 85.5 | 109.2 | 88.8 | 3.3 |
| 106 | 1.7 | 327.6 | 82.8 | 44.1 | 85.3 | 2.5 |
| 107 | 1.8 | 395.0 | 73.0 | 54.1 | 84.4 | 11.4 |
| 108 | 2.3 | 520.7 | 46.0 | 184.7 | 70.5 | 24.6 |
| 109 | 2.1 | 208.6 | 54.1 | 189.8 | 91.1 | 37.0 |
| 110 | 1.4 | 1101.0 | 4.9 | 625.9 | 26.2 | 21.3 |
| 111 | 1.8 | 747.7 | 37.6 | 325.3 | 75.7 | 38.1 |
| 112 | 1.7 | 423.3 | 33.4 | 337.4 | 65.7 | 32.3 |
| 113 | 2.2 | 54.7 | 85.4 | 59.0 | 94.0 | 8.7 |
| 114 | 0.8 | 161.0 | 80.3 | 147.6 | 98.5 | 18.2 |
| 115 | 2.9 | 786.3 | 26.1 | 642.8 | 57.4 | 31.2 |
| 116 | 1.4 | 676.3 | 73.5 | 94.9 | 81.2 | 7.7 |
| 117 | 9.4 | 448.9 | 45.1 | 533.3 | 73.7 | 28.6 |
| 118 | 3.8 | 853.1 | 8.7 | 1050.0 | 34.1 | 25.4 |
| 119 | 2.3 | 202.3 | 6.6 | 605.0 | 15.9 | 9.3 |
| 120 | 1.3 | 109.5 | 73.2 | 77.8 | 91.5 | 18.2 |
| 121 | 5.3 | 241.6 | 15.9 | 156.5 | 33.8 | 17.9 |
| 122 | 2.9 | 502.4 | 8.9 | 417.4 | 39.7 | 30.8 |
| 123 | 0.9 | 194.6 | 65.4 | 127.6 | 90.8 | 25.4 |
| 124 | 0.7 | 217.7 | 99.2 | 250.5 | 100.5 | 1.3 |
| 125 | 1.0 | 508.0 | 21.2 | 574.9 | 55.3 | 34.1 |
| 126 | 0.9 | 227.3 | 78.2 | 232.9 | 90.0 | 11.7 |
| 127 | 1.1 | 231.9 | 67.9 | 202.1 | 83.0 | 15.1 |
| 128 | 0.8 | 251.7 | 69.1 | 324.5 | 88.4 | 19.3 |
| 129 | 1.9 | 948.4 | 67.2 | 622.8 | 79.1 | 11.9 |
| 130 | 1.8 | 369.3 | 66.1 | 229.4 | 79.7 | 13.6 |
| 131 | 1.7 | 570.6 | 37.4 | 437.0 | 60.3 | 22.9 |
| 132 | 5.5 | 421.5 | 23.2 | 791.2 | 74.0 | 50.8 |
| 133 | 0.8 | 67.5 | 73.4 | 82.6 | 95.9 | 22.5 |
| 134 | 1.8 | 216.1 | 89.2 | 243.4 | 93.8 | 4.7 |
| 135 | 2.9 | 126.9 | 68.8 | 258.0 | 87.9 | 19.2 |
| 136 | 2.5 | 278.7 | 58.8 | 440.9 | 100.8 | 42.0 |
| 137 | 0.9 | 142.6 | 73.6 | 324.0 | 87.6 | 14.0 |
| 138 | 1.2 | 203.5 | 78.1 | 433.3 | 83.7 | 5.6 |
| 139 | 1.5 | 262.3 | 70.7 | 798.3 | 72.4 | 1.7 |
| 140 | 4.1 | 704.3 | 21.3 | 1573.0 | 37.0 | 15.6 |
| 141 | 1.1 | 441.3 | 22.6 | 399.7 | 62.2 | 39.7 |
| 142 | 0.9 | 122.8 | 78.1 | 140.2 | 92.5 | 14.4 |
| 143 | 13.3 | 252.2 | 83.5 | 225.1 | 91.2 | 7.7 |
| 144 | 0.9 | 397.4 | 73.6 | 334.1 | 91.6 | 18.1 |
| 145 | 1.0 | 203.9 | 60.2 | 196.1 | 93.5 | 33.3 |
| 146 | 0.8 | 263.0 | 91.5 | 308.0 | 93.3 | 1.8 |
| 147 | 3.2 | 475.5 | 78.1 | 707.6 | 78.4 | 0.3 |
| 148 | 1.6 | 402.5 | 62.6 | 858.3 | 77.6 | 14.9 |
| 149 | 1.8 | 351.0 | 32.4 | 249.7 | 77.1 | 44.7 |
| 150 | 1.5 | 346.0 | 45.6 | 376.1 | 79.3 | 33.7 |
| 151 | 1.3 | 421.2 | 76.0 | 551.1 | 83.3 | 7.2 |
| 152 | 1.6 | 63.9 | 2.0 | 1026.0 | 23.0 | 21.0 |
| 153 | 1.2 | 315.2 | 15.2 | 262.5 | 52.4 | 37.2 |
| 154 | 1.3 | 509.2 | 17.9 | 616.3 | 66.5 | 48.7 |
| 155 | 2.9 | 988.8 | 29.0 | 1094.0 | 61.3 | 32.2 |
| 156 | 2.5 | 193.4 | 4.5 | 228.5 | 19.5 | 15.0 |
| 157 | 0.8 | 124.0 | 63.6 | 29.1 | 93.6 | 30.0 |
| 158 | 4.2 | 746.9 | 36.2 | 564.2 | 77.8 | 41.6 |
| 159 | 1.9 | 366.8 | 28.9 | 551.5 | 34.1 | 5.2 |
| 160 | 3.4 | 546.8 | 4.3 | 508.3 | 15.1 | 10.8 |
| 161 | 4.8 | 418.8 | 18.3 | 930.3 | 45.0 | 26.7 |
| 162 | 0.5 | 322.5 | 87.1 | 202.4 | 90.8 | 3.7 |
| 163 | 1.7 | 241.2 | 48.4 | 341.8 | 86.9 | 38.6 |
| 164 | 3.2 | 1076.0 | 58.3 | 1252.0 | 81.3 | 23.0 |
| 165 | 1.6 | 306.2 | 37.8 | 286.3 | 61.1 | 23.4 |
| 166 | 1.6 | 302.6 | 56.4 | 548.7 | 71.7 | 15.3 |
| 167 | 2.2 | 149.9 | 74.9 | 159.4 | 87.4 | 12.5 |
| 168 | 1.5 | 123.0 | 48.1 | 118.7 | 83.1 | 35.0 |
| 169 | 20.9 | 1663.0 | 12.4 | 3027.0 | 68.5 | 56.1 |
| 170 | 2.6 | 431.7 | 76.0 | 759.0 | 87.7 | 11.8 |
| 171 | 7.0 | 287.4 | 71.3 | 409.7 | 88.0 | 16.7 |
| 172 | 0.6 | 398.5 | 10.7 | 718.0 | 42.4 | 31.8 |
| 173 | 1.3 | 364.1 | 70.4 | 520.4 | 83.0 | 12.6 |
| 174 | 3.4 | 527.1 | 81.1 | 423.4 | 85.3 | 4.2 |
| 175 | 1.0 | 381.3 | 22.7 | 822.2 | 47.5 | 24.8 |
| 176 | 1.3 | 246.3 | 56.9 | 316.1 | 74.5 | 17.6 |
| 177 | 1.6 | 168.6 | 67.3 | 176.6 | 80.2 | 12.9 |
| 178 | 1.2 | 109.9 | 55.0 | 275.6 | 74.5 | 19.5 |
| 179 | 1.2 | 277.2 | 65.4 | 440.2 | 96.5 | 31.2 |
| 180 | 1.8 | 246.9 | 38.1 | 186.8 | 77.7 | 39.5 |
| 181 | 2.8 | 363.7 | 54.6 | 262.6 | 79.2 | 24.7 |
| 182 | 93.9 | 4764.0 | 8.0 | 1895.0 | 16.2 | 8.2 |
| 183 | 64.0 | 4498.0 | 15.0 | 3311.0 | 23.2 | 8.2 |
| 184 | 9.6 | 421.5 | 21.6 | 562.4 | 60.3 | 38.7 |
| 185 | 13.1 | 249.6 | 19.9 | 675.7 | 63.0 | 43.1 |
| 186 | 1.9 | 509.3 | 35.8 | 697.1 | 63.5 | 27.7 |
| 187 | 2.5 | 356.7 | 35.8 | 391.7 | 71.5 | 35.6 |
| 188 | 1.2 | 236.2 | 30.4 | 190.2 | 60.5 | 30.1 |
| 189 | 1.1 | 151.5 | 65.3 | 189.2 | 81.0 | 15.7 |
| 190 | 1.5 | 424.3 | 65.1 | 387.8 | 77.4 | 12.4 |
| 191 | 2.0 | 338.0 | 27.1 | 440.5 | 37.2 | 10.1 |
| 192 | 0.9 | 170.4 | 4.3 | 2907.0 | 27.5 | 23.2 |
| 193 | 1.0 | 303.4 | 55.4 | 170.4 | 74.0 | 18.6 |
| 194 | 1.5 | 516.8 | 41.9 | 291.0 | 56.2 | 14.4 |
| 195 | 0.6 | 542.2 | 12.9 | 485.8 | 30.0 | 17.1 |
| 196 | 2.7 | 552.3 | 36.6 | 386.8 | 40.3 | 3.7 |
| 197 | 4.4 | 769.0 | 43.7 | 1040.0 | 45.5 | 1.8 |
| 198 | 14.3 | 1227.0 | 8.2 | 1148.0 | 15.5 | 7.3 |
| 199 | 2.4 | 96.8 | 58.6 | 506.5 | 80.8 | 22.2 |
| 200 | 1.8 | 47.9 | 57.5 | 307.7 | 85.9 | 28.4 |
| 201 | 2.3 | 88.4 | 47.8 | 485.6 | 69.5 | 21.7 |

The compounds shown in the Table immediately above were tested in the binding, GRAMMER and GITAR assays and demonstrated a superior activity profile. The compounds shown in Table I have potencies in the GRAMMER and GITAR assays (as measured by inflection points, IP) of less than 6000 nM concomitant with maximum activity in the GRAMMER assay less than the maximum activity in the GITAR assay.

Preferred compounds have potencies in the GRAMMER and GITAR assay (as measured by the inflection points, IP) of less than 300 nM concomitant with a maximum activity in the activity in the GRAMMER assay of less than 60% and a maximum activity in the GITAR assay of between 40 and 80%.

What is claimed is:
1. A compound of Formula I

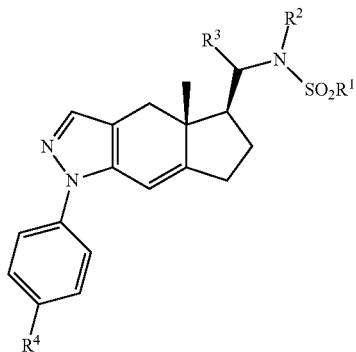

or a pharmaceutically acceptable salt thereof, wherein
R¹ is selected from the group consisting of:
(a) C₁₋₆alkyl, optionally mono-, di- or tri substituted with substituents independently selected from
 (1) halo,
 (2) —CF₃,
 (3) hydroxyl,
 (4) oxo,
 (5) —CN, and
 (6) pyridine,
(b) C₂₋₆alkenyl, optionally mono-, di- or tri substituted with fluoro,
(c) —C₃₋₆cycloalkyl,
(d) —C₁₋₂alkylC₃₋₆cycloalkyl,
(e) heterocycle,
(f) —C₁₋₂alkylheterocycle,
(g) aryl selected from phenyl or naphthyl,
(h) —C₁₋₂alkylaryl,
(i) —C₂₋₄alkenylaryl,
(j) heteroaryl,
(k) —C₁₋₂alkylheteroaryl,
(l) —Oheteroaryl,
(m) —OC₁₋₆alkyl optionally mono-, di- or tri substituted with fluoro,
(n) —C1-4alkyl-O—C1-6alkyl, optionally substituted with hydroxy, or —O—S(O)₂—C₁₋₂alkyl-CF₃,
(o) —OC₃₋₆cycloalkyl, and
(p) —Oaryl,
wherein the heteroaryl, aryl and heterocycle of choices (e), (f), (g), (h), (i), (j), (k), (l), and (p) are optionally substituted with 1, 2 or 3 substituents independently selected from the group consisting of
(1) hydroxyl,
(2) halo,
(3) —CN,
(4) —CF₃,
(5) —C₁₋₄alkyl,
(6) —OC₁₋₄alkyl,
(7) —O—CH₂CF₃,
(8) heteroaryl selected from pyrazole, thiophene, imidazole, and oxazole, optionally substituted with 1, 2 or 3 substitutents independently selected from methyl CF₃ and halo,
(9) —NH—OCH₃,
(10) phenyl,
(11) —O-phenyl,
(12) pyridine,
(13) —O-pyridine,
(14) —NH—C(O)—NH—CH₃,
(15) —NH—C(O)—C₁₋₄alkyl,
(16) —NH—C(O)—C₃₋₆cycloalkyl,
(17) —C₁₋₃alkyl-C(O)—OH,
(18) —C₁₋₃alkyl-C(O)—O—CH₃,
(19) —C(O)—NH₂,
(20) —C(O)—C₁₋₄alkyl-NH₂,
(21) —C(O)—NH—C₃₋₆cycloalkyl,
(22) —C(O)—OH,
(23) —C(O)—O—C₁₋₄alkyl,
(24) —C₁₋₂alkyl-heterocycle,
(25) —C₂₋₄alkenyl-C(O)-phenyl, and
(26) —O—S(O)₂—C₁₋₂alkyl-CF₃;
R² is selected from the group consisting of:
(a) H,
(b) OH,
(c) C₁₋₈alkyl, optionally mono-, di- or tri substituted with substituents independently selected from
 (1) halo,
 (2) hydroxyl,
 (3) oxo,
 (4) —CN,
 (5) CHF2,
 (6) CF3,
 (7) pyridyl,
 (8) —O—S(O)₂—CF₃, and
 (9) —O—S(O)₂—C₁₋₂alkyl-CF₃,
(d) C₂₋₆alkenyl, optionally mono-, di- or tri substituted with fluoro,
(e) —C₁₋₂alkylC₃₋₆cycloalkyl,
(f) heterocycle,
(g) —C₁₋₂alkylheterocycle,
(h) aryl selected from phenyl or naphthyl,
(i) —C₁₋₃alkylaryl,
(j) —C₂₋₄alkenylaryl,
(k) heteroaryl,
(l) —C₁₋₂alkylheteroaryl,
(m) —CH₂pyridyl, and
(o) —C₁₋₄alkyl-O—C₁₋₆alkyl, optionally substituted with hydroxy, or —O—S(O)₂—C₁₋₂alkyl-CF₃,
wherein the cycloalkyl, heteroaryl, aryl and heterocycle of choices (e), (f), (g), (h), (i), (j), (k), (l) and (m) are optionally substituted with 1, 2 or 3 substituents independently selected from the group consisting of
(1) hydroxyl,
(2) halo,
(3) —CN,
(4) —CF₃,
(5) —C₁₋₄alkyl,
(6) —OCH₃,
(7) —O—CH₂CF₃,
(8) heteroaryl selected from pyrazole, thiophene, imidazole, and oxazole, optionally substituted with 1, 2 or 3 substitutents independently selected from methyl, and halo,
(9) —NH—OCH₃,
(10) phenyl,
(11) —O-phenyl,
(12) pyridine,
(13) —O-pyridine,
(14) —NH—C(O)—NH—CH₃,
(15) —NH—C(O)—C₁₋₄alkyl,
(16) —NH—C(O)—C₃₋₆cycloalkyl,
(17) —C₁₋₃alkyl-C(O)—OH,
(18) —C₁₋₃alkyl-C(O)—O—CH₃,
(19) —C(O)—NH₂,
(20) —C(O)—C₁₋₄alkyl-NH₂,

(21) —C(O)—NH—$C_{3-6}$cycloalkyl,
(22) —C(O)—OH,
(23) —C(O)—O—$C_{1-4}$alkyl,
(24) —$C_{1-2}$alkyl-heterocycle,
(25) —$C_{2-4}$alkenyl-C(O)-phenyl, and
(26) —O—S(O)$_2$—$C_{1-2}$alkyl-CF$_3$;
$R^3$ is selected from
  (a) H,
  (b) $C_{1-6}$alkyl,
  (c) $C_{3-6}$cycloalkyl, and
  (d) $C_{1-6}$fluoroalkyl; and
$R^4$ is hydrogen or F.

2. The compound according to claim 1 wherein
$R^1$ is selected from the group consisting of:
  (a) $C_{1-6}$alkyl, optionally mono-, di- or tri substituted with substituents independently selected from
    (1) halo selected from fluoro and chloro,
    (2) —CF$_3$,
    (3) hydroxyl, and
    (4) pyridine,
  (b) $C_{2-6}$alkenyl, optionally mono-, di- or tri substituted with fluoro,
  (c) —$C_{3-6}$cycloalkyl,
  (d) —$C_{1-2}$alkyl$C_{3-6}$cycloalkyl,
  (e) heterocycle,
  (f) —$C_{1-2}$alkylheterocycle,
  (g) aryl selected from phenyl or naphthyl,
  (h) —$C_{1-2}$alkylaryl,
  (i) —$C_{2-4}$alkenylaryl,
  (j) heteroaryl,
  (k) —$C_{1-2}$alkylheteroaryl,
  (l) —Oheteroaryl,
  (m) —OC$_{1-6}$alkyl optionally mono-, di- or tri substituted with fluoro,
  (n) —C1-4alkyl-O—C1-6alkyl, optionally substituted with hydroxy, or —O—S(O)$_2$—$C_{1-2}$alkyl-CF$_3$,
  (O) —OC$_{3-6}$cycloalkyl, and
  (p) —Oatyl,
wherein the heteroaryl, aryl and heterocycle of choices (e), (f), (g), (h), (i), (j), (k), (l), and (p) are optionally substituted with 1, 2 or 3 substituents independently selected from the group consisting of
  (1) hydroxyl,
  (2) halo,
  (3) —CN,
  (4) —CF$_3$,
  (5) —$C_{1-4}$alkyl,
  (6) —OC$_{1-4}$alkyl,
  (7) —O—CH$_2$CF$_3$,
  (8) —NH—OCH$_3$,
  (9) —NH—C(O)—NH—CH$_3$,
  (10) —NH—C(O)—$C_{1-4}$alkyl,
  (11) —NH—C(O)—$C_{3-6}$cycloalkyl,
  (12) —$C_{1-3}$alkyl-C(O)—OH,
  (13) —$C_{1-3}$alkyl-C(O)—O—Ch$_3$,
  (14) —C(O)—NH$_2$,
  (15) —C(O)—$C_{1-4}$alkyl-NH$_2$,
  (16) —C(O)—NH—$C_{3-6}$cycloalkyl,
  (17) —C(O)—OH,
  (18) —C(O)—O—$C_{1-4}$alkyl,
  (19) —$C_{1-2}$alkyl-heterocycle,
  (20) —$C_{2-4}$alkenyl-C(O)-phenyl, and
  (21) —O—S(O)$_2$—$C_{1-2}$alkyl-CF$_3$.

3. The compound according to claim 2 wherein
$R^1$ is selected from the group consisting of:
(a) $C_{1-6}$alkyl, optionally mono-, di- or tri substituted with substituents independently selected from
  (1) halo selected from fluoro and chloro,
  (2) —CF$_3$,
  (3) hydroxyl, and
  (4) pyridine,
(b) —$C_{3-6}$cycloalkyl,
(c) —$C_{1-2}$alkyl$C_{3-6}$cycloalkyl,
(d) heterocycle,
(e) —$C_{1-2}$alkylheterocycle,
(f) aryl selected from phenyl or naphthyl,
(g) —$C_{1-2}$alkylaryl,
(h) heteroaryl,
(i) —$C_{1-2}$alkylheteroaryl,
wherein the heteroaryl, aryl and heterocycle of choices (d), (e), (f), (g), (h) and (i) are optionally substituted with 1, 2 or 3 substituents independently selected from the group consisting of
  (1) halo,
  (2) —CN,
  (3) —CF$_3$,
  (4) —$C_{1-4}$alkyl,
  (5) —OC$_{1-4}$alkyl,
  (6) —O—CH$_2$CF$_3$,
  (7) —C(O)—NH$_2$, and
  (8) —C(O)—O—$C_{1-4}$alkyl.

4. The compound according to claim 3 wherein
$R^1$ is selected from the group consisting of:
(a) $C_{1-6}$alkyl, optionally mono-, di- or tri substituted with substituents independently selected from
  (1) halo selected from fluoro and chloro,
  (2) —CF$_3$,
  (3) hydroxyl, and
  (4) pyridine,
(b) aryl selected from phenyl or naphthyl,
(c) —$C_{1-2}$alkylaryl,
(d) heteroaryl, and
(e) —$C_{1-2}$alkylheteroaryl,
wherein the heteroaryl, aryl and heterocycle of choices (b), (c), (d) and (e) are optionally substituted with 1, 2 or 3 substituents independently selected from the group consisting of
  (1) halo, selected from fluoro and chloro
  (2) —CF$_3$,
  (3) —$C_{1-4}$alkyl,
  (4) —OC$_{1-4}$alkyl,
  (5) —C(O)—NH$_2$, and
  (6) —C(O)—O—$C_{1-4}$alkyl.

5. The compound according to claim 1 wherein
$R^2$ is selected from the group consisting of:
(a) H,
(b) OH,
(c) $C_{1-8}$alkyl, optionally mono-, di- or tri substituted with substituents independently selected from
  (1) halo,
  (2) hydroxyl,
  (3) oxo,
  (4) —CN,
  (5) CHF$_2$,
  (6) CF$_3$,
  (7) pyridyl, and
  (8) —O—S(O)$_2$—$C_{1-2}$alkyl-CF$_3$;
(d) $C_{2-6}$alkenyl, optionally mono-, di- or tri substituted with fluoro,
(e) —$C_{1-2}$alkyl$C_{3-6}$cycloalkyl,
(f) heterocycle,
(g) —$C_{1-2}$alkylheterocycle,
(h) aryl selected from phenyl or naphthyl,
(i) —$C_{1-2}$alkylaryl, (j) —C$_{2-4}$alkenylaryl,
(k) heteroaryl,
(l) —C$_{1-2}$alkylheteroaryl,
(m) —CH$_2$pyridyl,
(O) —C1-4alkyl-O—C1-6alkyl, optionally substituted with hydroxy, or —O—S(O)$_2$—C$_{1-2}$alkyl-CF$_3$,
wherein the cycloalkyl, heteroaryl, aryl and heterocycle of choices (e), (f), (g), (h), (i), (j), (k), (l) and (m) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OCH$_3$,
(7) —O—CH$_2$CF$_3$,
(8) —NH—C(O)—NH—CH$_3$,
(9) —NH—C(O)—C$_{1-4}$alkyl,
(10) —NH—C(O)—C$_{3-6}$cycloalkyl,
(11) —C$_{1-3}$ alkyl-C(O)—OH,
(12) —C$_{1-3}$alkyl-C(O)—O—CH$_3$,
(13) —C(O)—NH$_2$,
(14) —C(O)—C$_{1-4}$alkyl-NH$_2$,
(15) —C(O)—NH—C$_{3-6}$cycloalkyl,
(16) —C(O)—OH,
(17) —C(O)—O—C$_{1-4}$alkyl,
(18) —C$_{1-2}$alkyl-heterocycle,
(19) —C$_{2-4}$alkenyl-C(O)-phenyl, and
(20) —O—S(O)$_2$—C$_{1-2}$alkyl-CF$_3$.

6. The compound according to claim 5 wherein R$^2$ is selected from the group consisting of
(a) H,
(b) OH,
(c) C$_{1-8}$alkyl, optionally mono-, di- or tri substituted with substituents independently selected from
(1) halo,
(2) hydroxyl,
(3) oxo,
(4) —CN,
(5) CHF$_2$,
(6) CF$_3$, and
(7) —O—S(O)$_2$—C$_{1-2}$alkyl-CF$_3$;
(d) —C$_{1-2}$alkylC$_{3-6}$cycloalkyl,
(e) —C$_{1-2}$alkylheterocycle,
(f) aryl selected from phenyl or naphthyl,
(g) —C$_{1-2}$alkylaryl,
(h) heteroaryl,
(i) —C$_{1-2}$alkylheteroaryl,
(j) —C$_{1-4}$alkyl-O—CH$_3$,
wherein the cycloalkyl, heteroaryl, aryl and heterocycle of choices (d), (e), (f), (g), (h) and (i) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OCH$_3$,
(7) —O—CH$_2$CF$_3$,
(8) —NH—C(O)—NH—CH$_3$,
(9) —NH—C(O)—C$_{1-4}$alkyl,
(10) —NH—C(O)—C$_{3-6}$cycloalkyl,
(11) —C$_{1-3}$alkyl-C(O)—OH,
(12) —C$_{1-3}$alkyl-C(O)—O—CH$_3$,
(13) —C(O)—NH$_2$,
(14) —C(O)—C$_{1-4}$alkyl-NH$_2$,
(15) —C(O)—NH—C$_{3-6}$cycloalkyl,
(16) —C(O)—OH,
(17) —C(O)—O—C$_{1-4}$alkyl,
(18) —C$_{1-2}$alkyl-heterocycle,
(19) —C$_{2-4}$alkenyl-C(O)-phenyl, and
(20) —O—S(O)$_2$—C$_{1-2}$alkyl-CF$_3$.

7. The compound according to claim 6 wherein R$^2$ is selected from the group consisting of:
(a) H,
(b) OH,
(c) C$_{1-8}$alkyl, optionally mono-, di- or tri substituted with substituents independently selected from
(1) halo,
(2) hydroxyl,
(3) CHF$_2$,
(4) CF$_3$, and
(5) —O—S(O)$_2$—C$_{1-2}$alkyl-CF$_3$;
(d) —C$_{1-2}$alkylC$_{3-6}$cycloalkyl,
(e) aryl selected from phenyl or naphthyl,
(f) —C$_{1-2}$alkylaryl,
(g) —C$_{1-2}$alkylheteroaryl,
(h) —C$_{1-4}$alkyl-O—CH$_3$,
wherein the cycloalkyl, heteroaryl, aryl and heterocycle of choices (d), (e), (f), (g), (h) and (i) are optionally substituted with 1, 2 or 3 substituents independently selected from the group consisting of
(1) hydroxyl,
(2) halo,
(3) —CN,
(4) —CF$_3$,
(5) —C$_{1-4}$alkyl,
(6) —OCH$_3$,
(7) —O—CH$_2$CF$_3$, and
(8) —O—S(O)$_2$—C$_{1-2}$alkyl-CF$_3$.

8. The compound according to claim 1 wherein R$^3$ is selected from
(a) H, and
(b) C$_{1-6}$alkyl.

9. The compound according to claim 8 wherein R$^3$ is hydrogen.

10. The compound according to claim 1 wherein: R$^4$ is F.

11. The compound of claim 1 of Formula II or a pharmaceutically acceptable salt thereof wherein R$^1$ is selected from the group consisting of:
(a) C$_{1-6}$alkyl, optionally mono-, di- or tri substituted with substituents independently selected from
(1) halo selected from fluoro and chloro,
(2) —CF$_3$, (3) hydroxyl, and
(4) pyridine,
(b) aryl selected from phenyl or naphthyl,
(c) —$C_{1-2}$alkylaryl,
(d) heteroaryl,
(e) —$C_{1-2}$alkylheteroaryl,
wherein the heteroaryl, aryl and heterocycle of choices (b), (c), (d) and (e) are optionally substituted with 1, 2 or 3 substituents independently selected from the group consisting of
(1) halo, selected from Fluoro and Chloro
(2) —$CF_3$,
(3) —$C_{1-4}$alkyl,
(4) —$OC_{1-4}$-alkyl,
(5) —C(O)—$NH_2$, and
(6) —C(O)—O—$C_{1-4}$alkyl; and
$R^2$ is selected from the group consisting of:
(a) H,
(b) OH,
(c) $C_{1-8}$alkyl, optionally mono-, di- or tri substituted with substituents independently selected from
(1) halo,
(2) hydroxyl,
(3) $CHF_2$,
(4) $CF_3$, and
(5) —O—S(O)$_2$—$C_{1-2}$alkyl-$CF_3$;
(d) —$C_{1-2}$alkyl$C_{3-6}$cycloalkyl,
(e) aryl selected from phenyl or naphthyl,
(f) —$C_{1-2}$alkylaryl,
(g) —$C_{1-2}$alkylheteroaryl,
(h) —$C_{1-4}$alkyl-O—$CH_3$,
wherein the cycloalkyl, heteroaryl, aryl and heterocycle of choices (d), (e), (f), (g), (h) and (i) are optionally substituted with 1, 2 or 3 substituents independently selected from the group consisting of
(1) hydroxyl,
(2) halo,
(3) —CN,
(4) —$CF_3$,
(5) —$C_{1-4}$alkyl, and
(6) —$OCH_3$.

12. The compound according to claim 11 wherein
$R^1$ is selected from the group consisting of:
(a) $C_{1-6}$alkyl, optionally mono-, di- or tri substituted with substituents independently selected from
(1) halo selected from fluoro and chloro,
(2) —$CF_3$,
(3) hydroxyl, and
(4) pyridine,
(b) aryl selected from phenyl or naphthyl,
(c) —$C_{1-2}$alkylaryl,
(d) heteroaryl, and
(e) —$C_{1-2}$alkylheteroaryl,
wherein the heteroaryl, aryl and heterocycle of choices (b), (c), (d) and (e) are optionally substituted with 1, 2 or 3 substituents independently selected from the group consisting of
(1) halo, selected from fluoro and chloro
(2) —$CF_3$,
(3) —$C_{1-4}$alkyl,
(4) —$OC_{1-4}$alkyl,
(5) —C(O)—$NH_2$, and
(6) —C(O)—O—$C_{1-4}$alkyl; and
$R^2$ is selected from the group consisting of:
(a) H,
(b) OH,
(c) $C_{1-8}$alkyl, optionally mono-, di- or tri substituted with substituents independently selected from
(1) halo,
(2) hydroxyl,
(3) $CHF_2$,
(4) $CF_3$, and
(5) —O—S(O)$_2$—$C_{1-2}$alkyl-$CF_3$,
(d) —$C_{1-2}$alkyl$C_{3-6}$cycloalkyl,
(e) aryl selected from phenyl or naphthyl,
(f) —$C_{1-2}$alkylaryl,
(g) —$C_{1-2}$alkylheteroaryl,
(h) —$C_{1-4}$alkyl-O—$CH_3$,
wherein the cycloalkyl, heteroaryl, aryl and heterocycle of choices (d), (e), (f), (g), (h) and (i) are optionally substituted with 1, 2 or 3 substituents independently selected from the group consisting of
(1) halo,
(2) —$CF_3$,
(3) —$C_{1-4}$alkyl, and
(4) —$OCH_3$,
or a pharmaceutically acceptable salt thereof.

13. A compound selected from
N-{[(4αR,5S)-1-(4-Fluorophenyl)-4α-methyl-1,4,4α,5,6,7-hexahydrocyclopenta[f]indazol-5-yl]methyl}-1-pyridin-3-yl-N-(2-pyridin-2-ylethyl)methanesulfonamide,
N-(cyclopropylmethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide,
N-allyl-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide,
N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide,
2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-5-(trifluoromethyl)benzenesulfonamide,
N-{4-[((cyclopropylmethyl){[(4αR,5S)-1-(4-fluorophenyl)-4α-methyl-1,4,4α,5,6,7-hexahydrocyclopenta[f]indazol-5-yl]methyl}amino)sulfonyl]phenyl}acetamide,
(5-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-1,3-dimethyl-1H-pyrazole-4-sulfonamide,
N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-4-methyl-3,4-dihydro-2H-1,4-benzoxazine-7-sulfonamide,
N-(cyclopropylmethyl)-N-{[(4αR,5S-1-(4-fluorophenyl)-4α-methyl-1,4,4α,5,6,7-hexahydrocyclopenta[f]indazol-5-yl]methyl}-4-pentylbenzenesulfonamide,
N-(cyclopropylmethyl)-N-{[(4αR,5S)-1-(4-fluorophenyl)-4α-methyl-1,4,4α,5,6,7-hexahydrocyclopenta[f]indazol-5-yl]methyl}biphenyl-4-sulfonamide,
N-(cyolopropylmethyl)-N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide,
2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}benzenesulfonamide, (E)-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-2-phenylethylenesulfonamide, 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}-4-{[(methylamino)carbonyl]amino}benzenesulfonamide, 3-chloro-N-(cyclopropylmethyl)-4-fluoro-N-{[(4αR,5S)-1-(4-fluorophenyl)-4α-methyl-1,4,4α,5,6,7-hexahydrocyclopenta[f]indazol-5-yl]methyl}benzenesulfonamide, N-(2-cyanoethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide, 2-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide, methyl 2-[((cyolopropylmethyl){[(4αR,5S)-1-(4-fluorophenyl)-4α-methyl-1,4,4α,5,6,7-hexahydrocyclopenta[f]indazol-5-yl]methyl}amino)sulfonyl]benzoate, 3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide, 3-chloro-N-(cyanomethyl)-4-fluoro-N-{[(4αR,5S)-1-(4-fluorophenyl)-4α-methyl-1,4,4a,5,6,7-hexahydrocyclopenta[f]indazol-5-yl]methyl}benzenesulfonamide, N-(cyolopropylmethyl)-N-{[(4αR,5S)-1-(4-fluorophenyl)-4α-methyl-1,4,4α,5,6,7-hexahydrocyclopenta[f]indazol-5-yl]methyl}-1-phenylmethanesulfonamide, 2-chloro-N-(cyclopropylmethyl)-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-5-methylisoxazole-4-sulfonamide, 4,5-dichloro-N-(cyanomethyl)-N-{[(4αR,5S)-1-(4-fluorophenyl)-4α-methyl-,4,4α,5,6,7-hexahydrocyclopenta[f]indazol-5-yl]methyl}thiophene-2-sulfonamide, N-(cyanomethyl)-3,4-difluoro-N-{[(4αR,5S)-1-(4-fluorophenyl)-4α-methyl-,1,4,4α,5,6,7-hexahydrocyclopenta[f]indazol-5-yl]methyl}benzenesulfonamide, 2,3-dichloro-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide, 4-chloro-N-(cyanomethyl)-N-{[(4αR,5S)-1-(4-fluorophenyl)-4α-methyl-,1,4,4α,5,6,7-hexahydrocyclopenta[f]indazol-5-yl]methyl}-3-(trifluoromethyl)benzenesulfonamide, 4-cyano-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide, 4-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}-2,5-dimethylbenzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-1-[3-(trifluoromethyl)phenyl]methanesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-5-methylthiophene-2-sulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonamide, (4αR,5S)-5-({(cyanomethyl)[(2,5-dimethyl-3-furyl)sulfonyl]amino}methyl)-1-(4-fluorophenyl)-4α-methyl-1,4,4α,5,6,7-hexahydrocyclopenta[f]indazol-2-ium, methyl 3-[((cyanomethyl){[(4αR,5S)-1-(4-fluorophenyl)-4α-methyl-1,4,4α,5,6,7-hexahydrocyclopenta[f]indazol-5-yl]methyl}amino)sulfonyl]thiophene-2-carboxylate, (N-(cyanomethyl)-N-{[(4αR,5S)-1-(4-fluorophenyl)-4α-methyl-1,4,4α,5,6,7-hexahydrocyclopenta[f]indazol-5-yl]methyl}-5-[1-methyl-3-(trifluoromethyl)-1H-pyrazol-5-yl]thiophene-2-sulfonamide, 3-cyano-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-1-methyl-1H-imidazole-4-sulfonamide, 4-(3-chloro-2-cyanophenoxy)-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-4-methyl-3,4-dihydro-2H-1,4-benzoxazine-7-sulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}naphthalene-1-sulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}-2,5-bis(2,2,2-trifluoroethoxy)benzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}biphenyl-4-sulfonamide, N-(cyanomethyl)-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-3,5-difluoro-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)N-{[(4αR,5S)-1-(4-fluorophenyl)-4α-methyl-,4,4α,5,6,7-hexahydrocyclopenta[f]indazol-5-yl]methyl}-4-(pyridin-2-yloxy)benzenesulfonamide, N-(cyanomethyl)-4-fluoro-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-2,4,5-trifluoro-N-{[(4αR,5S)-1-(4-fluorophenyl)-4α-methyl-,4,4α,5,6,7-hexahydrocyclopenta[f]indazol-5-yl]methyl}benzenesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methly}-1-phenylmethanesulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}2-methylbenzenesulfonamide, 2-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide, N-(cyanomethyl)-2,4-difluoro-N-{[(4αR,5S)-1-(4-fluorophenyl)-4α-methyl-1,4,4α,5,6,7-hexahydrocyclopenta[f]indazol-5-yl]methyl}benzenesulfonamide, 5-chloro-N-(cyanomethyl)-N-{[(4αR,5S)-1-(4-fluorophenyl)-4α-methyl-1,4,4α,5,6,7-hexahydrocyclopenta[f]indazol-5-yl]methyl}-1,3-dimethyl-1H-pyrazole-4-sulfonamide, N-(cyanomethyl)-N-{[(4αR,5S)-1-(4-fluorophenyl)-4α-methyl-1,4,4α,5,6,7-hexahydrocyclopenta[f]indazol-5-yl]methyl}biphenyl-2-sulfonamide,
N-(cyanomethyl)-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide,
2-cyano-N-(cyanomethyl)-N-{[(4αR,5S)-1-(4-fluorophenyl)-4α-methyl-1,4,4α,5,6,7-hexahydrocyclopenta[f]indazol-5-yl]methyl}benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-methylisoxazole-4-sulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5-(1,3-oxazol-5-yl)thiophene-2-sulfonamide,
3,4-diflouro-N-{[(4αR,5S)-1-(4-fluorophenyl)-4α-methyl-,4,4α,5,6,7-hexahydrocyclopenta[f]indazol-5-yl]methyl}-N-(2-hydroxyethyl)benzenesulfonamide,
2-chloro-4-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
2,3-dichloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
4-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-[3-(trifluoromethyl)phenyl]methanesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-5- methylthiophene-2-sulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-methyl-3-(trifluoromethyl-1H-pyrazole-4-sulfonamide,
N-{[(4αR,5S)-1-(4-fluorophenyl)-4α-methyl-,4,4α,5,6,7-hexahydrocyclopenta[f]indazol-5-yl]methyl}-N-(2-hydroxyethyl)-2,5-dimethylfuran-3-sulfonamide,
N-{[(4αR,5S)-1-(4-fluorophenyl)-4α-methyl-,4,4α,5,6,7-hexahydrocyclopenta[f]indazol-5-yl]methyl}-N-(2-hydroxyethyl)-5-[1-methyl-3-(trifluoromethyl)-1H-pyrazol-5-yl]thiophene-2-sulfonamide,
3-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
4-(3-chloro-2-cyanophenoxy)-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-2-(trifluoromethyl)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-3,5-dimethylisoxazole-4-sulfonamide,
3,5-difluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
methyl 2-{[{[(4αR,5S)-1-(4-fluorophenyl)-4α-methyl-,4,4α,5,6,7-hexahydrocyclopenta[f]indazol-5-yl]methyl}(2-hydroxyethyl)amino]sulfonyl}benzoate,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-4-(pyridin-2-yloxy)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1-phenylmethanesulfonamide,
2-chloro-N-{[(4αR,5S)-1-(4-fluorophenyl)-4α-methyl-,4,4α,5,6,7-hexahydrocyclopenta[f]indazol-5-yl]methyl}-N-(2-hydroxyethyl)-4-{[(methylamino)carbonyl]amino}benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-2-methylbenzenesulfonamide,
2-cyano-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-4-phenoxybenzenesulfonamide,
2-chloro-N-{[(4αR,5S)-1-(4-fluorophenyl)-4α-methyl-,4,4α,5,6,7-hexahydrocyclopenta[f]indazol-5-yl]methyl}-N-(2-hydroxyethyl)-5-(trifluoromethyl)benzenesulfonamide,
2-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
2,4-difluoro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)benzenesulfonamide,
5-chloro-N-{[(4αR,5S)-1-(4-fluorophenyl)-4α-methyl-1,4,4α,5,6,7-hexahydrocyclopenta[f]indazol-5-yl]methyl}-N-(2-hydroxyethyl)-1,3-dimethyl-1H-pyrazole-4-sulfonamide,
N-{[(4αR,5S)-1-(4-fluorophenyl)-4α-methyl-1,4,4α,5,6,7-hexahydrocyclopenta[f]indazol-5-yl]methyl}-N-(2-hydroxyethyl)biphenyl-2-sulfonamide,
N-(4-{[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}phenyl)acetamide,
2-fluoro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}benzenesulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}propane-1-sulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-[3-(trifluoromethyl)phenyl]methanesulfonamide,
2,2,2-trifluoro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}ethanesulfonamide,
2-fluoro-N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]benzenesulfonamide,
2-fluoro-N-{[(4αR,5S)-1-(4-fluorophenyl)-4α-methyl-1,4,4α,5,6,7-hexahydrocyclopenta[f]indazol-5-yl]methyl}-N-[2-(4-methylphenyl)ethyl]benzenesulfonamide,
N-[2-(2-chlorophenyl)ethyl]-2-fluoro-N-{[(4αR,5S)-1-(4-fluorophenyl)-4α-methyl-1,4,4α,5,6,7-hexahydrocyclopenta[f]indazol-5-yl]methyl}benzenesulfonamide, 2,2,2-trifluoro-N-[2-(2-fluorophenyl)ethyl]-N-{[(4αR)-1-(4-fluorophenyl)-4α-methyl-1,4,4α,5,6,7-hexahydrocyclopenta[f]indazol-5-yl]methyl}ethanesulfonamide,
2-fluoro-N-{[(4αR,5S)-1-(4-fluorophenyl)-4α-methyl-1,4,4α,5,6,7-hexahydrocyclopenta[f]indazol-5-yl]methyl}-N-(2-methoxyethyl)benzenesulfonamide,
N-{[(4αR,5S)-1-(4-fluorophenyl)-4α-methyl-1,4,4α,5,6,7-hexahydrocyclopenta[f]indazol-5-yl]methyl}-N-(2-methoxyethyl)propane-1-sulfonamide,
N-{[(4αR,5S)-1-(4-fluorophenyl)-4α-methyl-1,4,4α,5,6,7-hexahydrocyclopenta[f]indazol-5-yl]methyl}-N-(2-methoxyethyl)methanesulfonamide,
2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-2-(trifluoromethyl)benzenesulfonamide,
2-chloro-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}benzenesulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}cyclopropanesulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}butane-1-sulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-2-methylpropane-1-sulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}octane-1-sulfonamide,
1-(2,4-dichlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide,
1-(3-chlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide,
1-(2-chlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-[2-(trifluoromethyl)phenyl]methanesulfonamide,
N-(cyclopropylmethyl)-2,2,2-trifluoro-N-{1-[(4αR)-1-(4-fluorophenyl)-4α-methyl-1,4,4α,5,6,7-hexahydrocyclopenta[f]indazol-5-yl]ethyl}ethanesulfonamide,
N-{[(4αR,5S)-1-(4-fluorophenyl)-4α-methyl-1,4,4α,5,6,7-hexahydrocyclopenta[f]indazol-5-yl]methyl}-N-(tetrahydrofuran-2-ylmethyl)-1-[3-(trifluoromethyl)phenyl]methanesulfonamide,
1-(3,4-dichlorophenyl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}methanesulfonamide,
3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-[(2S)-2-hydroxypropyl]benzenesulfonamide,
2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[(2S)-2-hydroxypropyl]ethanesulfonamide,
(1S)-2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}-1-methylethyl 2,2,2-trifluoroethanesulfonate,
3-chloro-4-fluoro-N-{[(4αR,5S)-1-(4-fluorophenyl)-4α-methyl-1,4,4α,5,6,7-hexahydrocyclopenta[f]indazol-5-yl]methyl}-N-[(2R)-2-hydroxypropyl]benzenesulfonamide,
2-fluoro-N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]benzenesulfonamde,
2-{[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}benzamide,
2-(1,3-dioxo-1,3-dihydro-2H-isoindol-2-yl)-N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide,
N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]-1-[3-(trifluoromethyl)phenyl]methanesulfonamide,
2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(2-methoxyhenyl)ethyl]ethanesulfonamide,
2-(1,3-dioxo-1,3-dihydro-2H-isoindol-2-yl)-N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}ethanesulfonamide,
N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-1-[3-(trifluoromethyl)phenyl]methanesulfonamide,
N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-3,5-dimethylisoxazole-4-sulfonamide,
N-[2-(2-fluorophenyl)ethyl]-N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide,
N-{[(4αR,5S)-1-(4-fluorophenyl)-4α-methyl-1,4,4α,5,6,7-hexahydrocyclopenta[f]indazol-5-yl]methyl}-N-[2-(2-methoxyphenyl)ethyl]-1-pyridin-3-ylmethanesulfonamide,
2,2,2-trifluoro-N-{[(4αR,5S)-1-4-fluorophenyl)-4α-methyl-1,4,4α,5,6,7-hexahydrocyclopenta[f]indazol-5-yl]methyl}-N-[2-(3-methoxyphenyl)ethyl]ethanesulfonamide,
2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(4-methoxyphenyl)ethyl]ethanesulfonamide,
2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)ethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-4-ylethyl)ethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[2-(4-hydroxyphenyl)ethyl]ethanesulfonamide, N-{[(4αR,5S)-1-(4-fluorophenyl)-4α-methyl-1,4,4α,5,6,7-hexahydrocyclopenta[f]indazol-5-yl]methyl}-N-[2-(2-hydroxyphenyl)ethyl]-1-pyridin-3-ylmethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(pyridazin-3-ylmethyl)ethanesulfonamide, N-(3,3-difluoro-2-hydroxypropyl)-2,2,2-trifluoro-N-{[(4αR,5S)-1-(4-fluorophenyl)-4α-methyl-1,4,4α,5,6,7-hexahydrocyclopenta[f]indazol-5-yl]methyl}ethanesulfonamide, 2,2-difluoro-1-({{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}methyl)ethyl 2,2,2-trifluoroethanesulfonate, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-[(1-hydroxycyclopropyl)methyl]ethanesulfonamide, 1-({{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}methyl)cyclopropyl 2,2,2-trifluoroethanesulfonate, 2,2,2-trifluoro-N-[2-(2-fluorophenyl)ethyl]-N-{[(4αR,5S)-4α-methyl-1-phenyl-1,4,4α,5,6,7-hexahydrocyclopenta[f]indazol-5-yl]methyl}ethanesulfonamide, 2,2,2-trifluoro-N-{[(4αR,5S)-4α-methyl-1-phenyl-1,4,4α,5,6,7-hexahydrocyclopenta[f]indazol-5-yl]methyl}-N-(2-pyridin-2-ylethyl)ethanesulfonamide, 2,2,2-trifluoro-N-[2-(2-methoxyphenyl)ethyl]-N-{[(4αR,5S)-4α-methyl-1phenyl-1,4,4α,5,6,7-hexahydrocyclopenta[f]indazol-5-yl]methyl}ethanesulfonamide, N-{[(4αR,5S)-4α-methyl-1-phenyl-1,4,4α,5,6,7-hexahydrocyclopenta[f]indazol-5-yl]methyl}-1-pyridin-3-yl-N-(2-pyridin-2-ylethyl)methanesulfonamide, N-[2-(2-hydroxyphenyl)ethyl]-N-{[(4αR,5S)-4α-methyl-1-phenyl-1,4,4α,5,6,7-hexahydrocyclopenta[f]indazol-5-yl]methyl}-1-pyridin-3-ylmethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-2-ylethyl)ethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-3-ylethyl)ethanesulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-4-ylethyl)ethanesulfonamide, 2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}-1-pyridin-2-ylethyl 2,2,2-trifluoroethanesulfonate, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(2-pyridin-3-ylpropyl)ethanesulfonamide, N-(3-amino-4,4,4-trifluorobutyl)-2,2,2-trifluoro-N-{[(4αR,5S)-1-(4-fluorophenyl)-4α-methyl-,4,4α,5,6,7-hexahydrocyclopenta[f]indazol-5-yl]methyl}ethanesulfonamide, N-{[(4αR,5S)-1-(4-fluorophenyl)-4α-methyl-1,4,4α,5,6,7-hexahydrocyclopenta[f]indazol-5-yl]methyl}-N-(3,3,3-trifluoro-2-hydroxypropyl)propane-1-sulfonamide, N-{[(4αR,5S)-1-(4-fluorophenyl)-4α-methyl-1,4,4α,5,6,7-hexahydrocyclopenta[f]indazol-5-yl]methyl}-1-pyridin-3-yl-N-(3,3,3-trifluoro-2-hydroxypropyl)methanesulfonamide, N-{[(4αR,5S)-1-(4-fluorophenyl)-4α-methyl-1,4,4α,5,6,7-hexahydrocyclopenta[f]indazol-5-yl]methyl}-1-methyl-N-(2-pyridin-2-ylethyl)-3-(trifluoromethyl)-1H-pyrazole-4-sulfonamide, N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)propane-1-sulfonamide, 2-(1,3-dioxo-1,3-dihydro-2H-isoindol-2-yl)-N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)ethanesulfonamide, N-{[(4αR,5S)-1-(4-fluorophenyl)-4α-methyl-1,4,4α,5,6,7-hexahydrocyclopenta[f]indazol-5-yl]methyl}-N-(2-pyridin-2-ylethyl)-1-[2-(trifluoromethyl)phenyl]methanesulfonamide, N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide, N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}propane-1-sulfonamide, N-(3,3-difluoro-2-hydroxypropyl)-N-{[(4αR,5S)-1-(4-fluorophenyl)-4α-methyl-1,4,4α,5,6,7-hexahydrocyclopenta[f]indazol-5-yl]methyl}-1-methyl-3-(trifluoromethyl)-1H-pyrazole-4-sulfonaimde, N-{[(4αR,5S)-1-(4-fluorophenyl)-4α-methyl-1,4,4α,5,6,7-hexahydrocyclopenta[f]indazol-5-yl]methyl}-N-(2-hydroxy-2-pyridin-2-ylethyl)-1-methyl-3-(trifluoromethyl)-1H-pyrazole-4-sulfonamide, 2-fluoro-N-{[(4αR,5S)-1-(4-fluorophenyl)-4α-methyl-1,4,4α,5,6,7-hexahydrocyclopenta[f]indazol-5-yl]methyl}-N-(2-oxoethyl)benzenesulfonamide, methyl 2-(2-{{[(4αR,5S)-1-(4-fluorophenyl)-4α-methyl-1-,4,4α,5,6,7-hexahydrocyclopenta[f]indazol-5-yl]methyl}[(2,2,2-trifluoroethyl)sulfonyl]amino}ethyl)benzoate, methyl 5-chloro-2-(2-{{[(4αR,5S)-1-(4-fluorophenyl)-4α-methyl-1,4,4α,5,6,7-hexahydrocyclopenta[f]indazol-5-yl]methyl}[(2,2,2-trifluoroethyl)sulfonyl]amino}ethyl)benzoate, N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide, methyl 2-{[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzoate, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-{2-[2-(hydroxymethyl)phenyl]ethyl}ethanesulfonamide, 2-({[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzoic acid, N-{[(4αR,5S)-1-(4-fluorophenyl)-4α-methyl-1,4,4α,5,6,7-hexahydrocyclopenta[f]indazol-5-yl]methyl}-1-pyridin-2-yl-N-(2-pyridin-2-ylethyl)methanesulfonaimde, N-{[(4αR,5S)-1-(4-fluorophenyl)-4α-methyl-1,4,4α,5,6,7-hexahydrocyclopenta[f]indazol-5-yl]methly}-1-pyridin-4-yl-N-(2-pyridin-2-ylethyl)methanesulfonamide, 2-({[{[(4αR,5S)-1-(4-fluorophenyl)-4α-methyl-1,4,4α,4,5,6,7-hexahydrocyclopenta[f]1indazol-5-yl]methyl}(3,3,3-trifluoro-2-hydroxypropyl)amino]sulfonyl}methyl)benzamide, N-{[(4αR,5S)-1-(4-fluorophenyl)-4α-methyl-1,4,4α,5,6,7-hexahydrocyclopenta[f]indazol-5-yl]methyl}-N-[(2R)-2-hydroxypropyl]-3,5-dimethylisoxazole-4-sulfonamide, N-{[(4αR,5S)-1-(4-fluorophenyl)-4α-methyl-1,4,4α,5,6,7-hexahydrocyclopenta[f]indazol-5-yl]methyl}-1-pyridin-3-ylmethanesulfonamide, N-{[(4αR,5S)-1-(4-fluorophenyl)-4α-methyl-1,4,4α,5,6,7-hexahydrocyclopenta[f]indazol-5-yl]methyl}-3,5-dimethyl-N-(tetrahydrofuran-2-ylmethyl)isoxazole-4-sulfoanmide, N-{[(4αR,5S)-1-(4-fluorophenyl)-4α-methyl-1,4,4α,5,6,7-hexahydrocyclopenta[f]indazol-5-yl]methyl}-N-(2-methoxyethyl)ethanesulfonamide, N-{[(4αR,5S)-1-(4-fluorophenyl)-4α-methyl-1,4,4α,5,6,7-hexahydrocyclopenta[f]indazol-5-yl]methyl}-N-(2-methoxyethyl)-1-methyl-3-(trifluoromethyl)-1H-pyrazole-4-sulfonamide, N-{[(4αR,5S)-1-(4-fluorophenyl)-4α-methyl-1,4,4α,5,6,7-hexahydrocyclopenta[f]indazol-5-yl]methyl}-N-(2-methoxyethyl)-3,5-dimethylisoxazole-4-sulfonamide, N-{[(4αR,5S)-1-(4-fluorophenyl)-4α-methyl-1,4,4α,5,6,7-hexahydrocyclopenta[f]indazol-5-yl]methyl}-N-(tetrahydrofuran-2-ylmethyl)ethanesulfonamide, N-{[(4αR,5S)-1-(4-fluorophenyl)-4α-methyl-1,4,4α,5,6,7-hexahydrocyclopenta[f]indazol-5-yl]methyl}-1-methyl-N-(tetrahydrofuran-2-ylmethyl)-3-(trifluoromethyl)-1H-pyrazole-4-sulfonamide, N-{[(4αR,5S)-1-(4-fluorophenyl)-4α-methyl-1,4,4α,5,6,7-hexahydrocyclopenta[f]indazol-5-yl]methyl}-N,3,5-trimethylisoxazole-4-sulfonamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-methylethanesulfonamide, N-ethyl-N-{[(4αR,5S)-1-(4-fluorophenyl)-4α-methyl-1,4,4α,5,6,7-hexahydrocyclopenta[f]indazol-5-yl]methyl}-3,5-dimethylisoxazole-4-sulfonamide, N-ethyl-2,2,2-trifluoro-N-{[(4αR,5S)-1-(4-fluorophenyl)-4α-methyl-1,4,4α,5,6,7-hexahydrocyclopenta[f]indazol-5-yl]methyl}ethansulfonamide, methyl 2-[({[[(4αR,5S)-1-(4-fluorophenyl)-4α-methyl,1,4,4α,5,6,7-hexahydrocyclopenta[f]indazol-5-yl]methyl}[(2R)-2-hydroxypropyl]amino}sulfonyl)methyl]benzoate, methyl 2-[({[[(4αR,5S)-1-(4-fluorophenyl)-4α-methyl,1,4,4α,5,6,7-hexahydrocyclopenta[f]indazol-5-yl]methyl}[(2S)-2-hydroxypropyl]amino}sulfonyl)methyl]benzoate, methyl 2-({[{[(4αR,5S)-1-(4-fluorophenyl)-4α-methyl-1,4,4α,5,6,7-hexahydrocyclopenta[f]indazol-5-yl]methyl}(3,3,3-trifluoro-2-hydroxypropyl)amino]sulfonyl}methyl)benzoate, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-{2-[2-(hydroxymethyl)phenyl]ethyl}ethanesulfonamide, 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzoic acid, 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzoic acid, 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzamide, 2-[({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)methyl]benzamide, methyl 2-({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)benzoate, methyl 2-({{[(4αR,5S)-1-(4-fluorophenyl)-4α-methyl-1,4,4α,5,6,7-hexahydrocyclopenta[f]indazol-5-yl]methyl}[(2R)-2-hydroxypropyl]amino}sulfonyl)benzoate, methyl 2-{[((2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]methyl}benzoate, methyl 2-[([2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]benzoate, 2-{[([2-(2-fluorophenyl)ethyl]{[(4αR,5S)-1-(4-fluorophenyl)-4α-methyl-1,4,4α,5,6,7-hexahydrocyclopenta[f]indazol-5-yl]methyl}amino)sulfonyl]methyl}benzamide, 4-{[[{[(4αR,5S)-1-(4-fluorophenyl)-4α-methyl-1,4,4α,5,6,7-hexahydrocyclopenta[f]indazol-5-yl]methyl}(tetrahydrofuran-2-ylmethyl)amino]sulfonyl}benzamide, 3-[((2-fluorobenzyl){[(4αR,5S)-1-(4-fluorophenyl)-4α-methyl-1,4,4α,5,6,7-hexahydrocyclopenta[f]indazol-5-yl]methyl}amino)sulfonyl]benzamide, 2,2,2-trifluoro-N-{[(4αR,5S)-1-(4-fluorophenyl)-4α-methyl-1,4,4α,5,6,7-hexahydrocyclopenta[f]indazol-5-yl]methyl}-N-(3-phenylpropyl)ethanesulfonamide, N-{[(4αR,5S)-1-(4-fluorophenyl)-4α-methyl-1,4,4α,5,6,7-hexahydrocyclopenta[f]indazol-5-yl]methyl}-3,5-dimethyl-N-(3-phenylpropyl)isoxazole-4-sulfonamide, 2-fluoro-N-{[(4αR,5S)-1-(4-fluorophenyl)-4α-methyl-1,4,4α,5,6,7-hexahydrocyclopenta[f]indazol-5-yl]methyl}-N-(3-phenylpropyl)benzenesulfonamide, 2-({[{[(4αR,5S)-1-(4-fluorophenyl)-4α-methyl-1,4,4α,5,6,7-hexahydrocyclopenta[f]indazol-5-yl]methyl}(2-pyridin-2-ylethyl)amino]sulfonyl}methyl)benzamide, N-{1-[(4αR)-1-(4-fluorophenyl)-4α-methyl-1,4,4α,5,6,7-hexahydrocyclopenta[f]indazol-5-yl]ethyl}-1-pyridin-3-yl-N-(2-pyridin-2-ylethyl)methanesulfonamide, 2-({[{[(4αR,5S)-1-(4-fluorophenyl)-4α-methyl-1,4,4α,5,6,7-hexahydrocyclopenta[f]indazol-5-yl]methyl}(2-hydroxyethyl)amino]sulfonyl}methyl)benzamide, 2-fluoro-N-{[(4αR,5S)-1-(4-fluorophenyl)-4α-methyl-1,4,4α,5,6,7-hexahydrocyclopenta[f]indazol-5-yl]methyl}-N-(2-hydroxy-2-methylpropyl)benzenesulfonamide, and 2-fluoro-N-{[(4αR,5S)-1-(4-fluorophenyl)-4α-methyl-1,4,4α,5,6,7-hexahydrocyclopenta[f]indazol-5-yl]methyl}-N-[(1-hydroxycyclopropyl)methyl]benzenesulfonamide, or a pharmaceutically acceptable salt thereof.

14. A pharmaceutical composition comprising a compound according to claim 1 in combination with a pharmaceutically acceptable carrier.

* * * * *